(12) United States Patent
TenBrink

(10) Patent No.: US 6,514,968 B1
(45) Date of Patent: Feb. 4, 2003

(54) AMINOALKOXY CARBAZOLES FOR THE TREATMENT OF CNS DISEASES

(75) Inventor: Ruth Elizabeth TenBrink, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/652,768

(22) Filed: Aug. 31, 2000

Related U.S. Application Data

(60) Provisional application No. 60/152,638, filed on Sep. 7, 1999, and provisional application No. 60/203,771, filed on May 12, 2000.

(51) Int. Cl.$^7$ .................. A61K 31/5377; C07D 209/88; C07D 413/12
(52) U.S. Cl. .................. 514/232.8; 514/254.09; 514/323; 514/365; 514/394; 514/411; 544/142; 544/372; 546/200; 548/205; 548/305.1; 548/444
(58) Field of Search ............. 514/411, 232.8, 514/323, 365, 394, 254.09; 548/444, 205, 305.1; 546/200

(56) References Cited

U.S. PATENT DOCUMENTS

| 3,759,948 A | 9/1973 | Shen et al. .................. 260/315 |
| 3,896,145 A | 7/1975 | Berger et al. ................ 260/315 |
| 3,932,424 A | 1/1976 | Albrecht et al. ....... 260/293.61 |
| 4,503,067 A | 3/1985 | Wiedemann et al. ........ 514/411 |
| 4,938,949 A | 7/1990 | Borch et al. ................... 424/10 |
| 5,541,333 A * | 7/1996 | Fino ............................. 548/113 |
| 5,668,167 A | 9/1997 | Tidwell et al. ............... 514/411 |

FOREIGN PATENT DOCUMENTS

| DE | 4330175 | 3/1995 | ......... C07D/471/04 |
| EP | 0839806 | 5/1998 | ......... C07D/209/88 |
| WO | WO 95/03296 | 2/1995 | ......... C07D/333/74 |
| WO | WO 95/16684 | 6/1995 | ......... C07D/403/12 |
| WO | WO 96/26936 | 9/1996 | ......... C07D/401/04 |

OTHER PUBLICATIONS

Boess, et al., Mol. Pharmacol. 1998, 54, 577–583.
Bourson, et al., Brit. J. Pharm. 1998, 125, 1562–1566.
Cheng, V.C. et al., Biochem. Pharmacol., 22, 3099–3108, 1973.
D. Hoyer, et al., Pharmacological Reviews. 1994, 46, 157–203.
Glennon, et al., Neuroscience and Behavioral Reviews, 1990, 14, 35.
Hughes, DL; Progress in the Fischer Indole Reaction: A Review. Org. Prep. Proceed. Int. 1993, 25, 609–632.
Matsumoto, M.; Ishida, Y.; Watanabe, N. Heterocycles 1985, 23, 165–170.
MD Gershon, et al., The Peripheral Actions of 5–Hydroxytryptamine, 246 (1989).
Monsma, et al., Molecular Pharmacol. 1993, 43, 320–327.
PR Saxena, et al., Journal of Cardiovascular Pharmacology, 15:Supp. 7 (1990).
Roth, et al., J. Pharm. Exp. Therapeut. 1994, 268, 1403–1410.
Ruat, M. et al., Biochem. Biophys. Res. Com. 1993, 193, 269–276.
RW Fuller, Biology of Serotonergic Transmission, 221 (1982).
Sandler, SR; Karo, W. Organic Functional Group Preparations; Academic Press : NY, 1983; vol. I, $2^{nd}$ Ed., pp. 434–465.
Sibley, D.R., Journal of Neurochemistry, 66, 47–56, 1996, Kohen.
Sleight, et al., Brit. J. Pharmacol. 1998, 124, 556–562.
Sleight, et al., Exp. Opin. Ther. Patents 1998, 8, 1217–1224.
Yoshioka et al., Life Sciences, 1998, 17/18, 1473–1477.
Abstract of International Publication No. WO 97/47601, 1997.
Abstract of Japanese Patent No. 06228095, 1994.
Abstract of French Patent No. 2516512, 1983.

* cited by examiner

Primary Examiner—Joseph K. McKane
Assistant Examiner—Sonya N. Wright
(74) Attorney, Agent, or Firm—John H. Engelmann

(57) ABSTRACT

The present invention provides aminoalkoxy carbazole derivatives, and more specifically, provides compounds of formula (I)

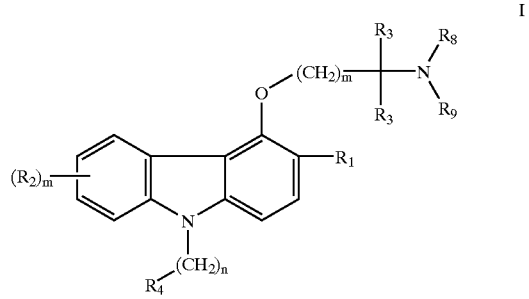

wherein $R_1$, $R_2$, $R_3$, $R_4$, $R_8$ and $R_9$ are described herein. These compounds are 5-HT ligands, and are useful for treating diseases wherein modulation of 5-HT activity is desired.

42 Claims, No Drawings

AMINOALKOXY CARBAZOLES FOR THE TREATMENT OF CNS DISEASES

CROSS REFERENCE

This application claims the benefit of the following provisional applications: U.S. Serial No.: 60/152,638, filed Sep., 7, 1999; U.S. Ser. No: 60/203,771, filed May 12, 2000, under 35 USC 119(e)(i).

FIELD OF THE INVENTION

The present invention provides aminoalkoxy carbazole derivatives, and more specifically, provides compounds of formula (I) described herein below. These compounds are 5-HT ligands, and are useful for treating diseases wherein modulation of 5-HT activity is desired.

BACKGROUND OF THE INVENTION

Many diseases of the central nervous system are influenced by the adrenergic, the dopaminergic, and the serotonergic neurotransmitter systems. For example, serotonin has been implicated in a number of diseases and conditions which originate in the central nervous system. These include diseases and conditions related to sleeping, eating, perceiving pain, controlling body temperature, controlling blood pressure, depression, anxiety, schizophrenia, and other bodily states. R. W. Fuller, Biology of Serotonergic Transmission, 221 (1982); D. J. Boullin, Serotonin in Mental Abnormalities 1:316 (1978); J. Barchas, et al., Serotonin and Behavior, (1973). Serotonin also plays an important role in peripheral systems, such as the gastrointestinal system, where it has been found to mediate a variety of contractile, secretory, and electrophysiologic effects.

As a result of the broad distribution of serotonin within the body, there is a tremendous interest in drugs that affect serotonergic systems. In particular, receptor-specific agonists and antagonists are of interest for the treatment of a wide range of disorders, including anxiety, depression, hypertension, migraine, obesity, compulsive disorders, schizophrenia, autism, neurodegenerative disorders (e.g. Alzheimer's disease, Parkinsonism, and Huntington's chorea), and chemotherapy-induced vomiting. M. D. Gershon, et al., The Peripheral Actions of 5-Hydroxytryptamine, 246 (1989); P. R. Saxena, et al., Journal of Cardiovascular Pharmacology, 15:Supplement 7 (1990).

The major classes of serotonin receptors ($5\text{-HT}_{1\text{-}7}$) contain fourteen to eighteen separate receptors that have been formally classified. See Glennon, et al., *Neuroscience and Behavioral Reviews,* 1990, 14, 35; and D. Hoyer, et al. *Pharmacol. Rev.* 1994, 46, 157–203. Recently discovered information regarding subtype identity, distribution, structure, and function suggests that it is possible to identify novel, subtype specific agents having improved therapeutic profiles (e.g. fewer side effects).

For example, the $5\text{-HT}_6$ receptor was identified in 1993 (Monsma et al. Mol. Pharmacol. 1993, 43, 320–327 and Ruat, M. et al. Biochem. *Biophys. Res. Com.* 1993, 193, 269–276). Several antidepressants and atypical antipsychotics bind to the $5\text{-HT}_6$ receptor with high affinity and this binding may be a factor in their profile of activities (Roth et al. *J. Pharm. Exp. Therapeut.* 1994, 268, 1403–1410; Sleight et al. *Exp. Opin. Ther. Patents* 1998, 8, 1217–1224; Bourson et al. *Brit. J. Pharm.* 1998, 125, 1562–1566; Boess et al. *Mol. Pharmacol.* 1998, 54, 577–583; Sleight et al. *Brit. J. Pharmacol.* 1998, 124, 556–562). In addition, the 5-HT6 receptor has been linked to generalized stress and anxiety states (Yoshioka et al. *Life Sciences* 1998, 17/18, 1473–1477). Together these studies and observations suggest that compounds that antagonize the 5-HT receptor will be useful in treating disorders of the central nervous system.

Compounds of the present invention are 5-HT ligands (e.g. receptor-specific agonists or antagonists). Thus they are useful for treating diseases wherein modulation of 5-HT activity is desired. Specifically, the compounds of this invention are useful in the treatment of psychosis, paraphrenia, psychotic depression, mania, schizophrenia, schizophreniform disorders, schizoaffective disorder, delusional disorder, panic disorder, a phobia, obsessive compulsive disorder, post-traumatic-stress syndrome, immune system depression, a stress induced problem with the urinary, a stress related disease such as anxiety, migraine headache, drug addiction, convulsive disorders, personality disorders, post-traumatic stress syndrome, alcoholism, panic attacks, obsessive-compulsive disorders, sleep disorders, disorders of the gastrointestinal or cardiovascular system (e.g., stress incontinence), neurodegenerative disorders, autism, chemotherapy-induced vomiting, hypertension, cluster headaches, sexual dysfunction in a mammal (e.g. a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition (e.g., dementia, mental retardation or delirium)), bipolar disorder, bulimia nervosa, chronic fatigue syndrome, conduct disorder, cyclothymic disorder, dysthymic disorder, fibromyalgia and other somatoform disorders, an inhalation disorder, an intoxication disorder, movement disorder (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders, psychotic disorder due to medical condition, psychotic disorder NOS), mood disorder (major depressive or bipolar disorder with psychotic features) seasonal affective disorder, a specific developmental disorder, agitation disorder, selective serotonin reuptake inhibition (SSRI) "poop out" syndrome or a Tic disorder (e.g., Tourette's syndrome). More specifically, the compounds of this invention are useful to treat psychotic, affective, vegetative, and psychomotor symptoms of schizophrenia or the extrapyramidal motor side effects of an antipsychotic drug. This last action will allow higher doses of antipsychotics to be used and thus greater antipsychotic efficacy to be obtained as a result of a reduction in side effects. The compounds of this invention are also useful in the modulation of eating behavior and thus are useful in treating excess weight and associated morbidity and mortality.

INFORMATION DISCLOSURE

International Publication No. WO95/03296 discloses carbazole and dibenzofuran hapten compounds.

Abstract of International Publication No. WO/9747601 discloses new heterocyclic compounds useful for treating schizophrenia.

European Patent Application EP 839806 discloses tricyclic compounds useful for inhibiting sPLA2 mediated release of fatty acids for conditions such as septic shock.

U.S. Pat. No. 5,668,167 discloses carbazole derivatives useful for treating microbial infections.

U.S. Pat. No. 4,503,067 discloses carbazolyl-(4)-oxypropanolamine compounds useful for treating cardiac diseases.

U.S. Pat. No. 3,932,424 discloses carbazoles useful as antiviral agents.

U.S. Pat. No. 3,896,145 discloses carbazoles useful as antiinflammatory, analgesic, and anti-rheumatic agents.

U.S. Pat. No. 3,759,948 discloses tricyclic carboxylic acid and ester derivatives useful as anti-inflammatory, anti-pyretic and analgesic agents.

DE 4330175 discloses beta carbolines useful for treating Parkinson's disease, Alzheimer's disease, senile dementia, epilepsy, schizophrenia, migraine etc.

Abstract of Japanese Patent No. 06228095 discloses carbazole derivatives useful for treating ischaemic encephalopathy.

Abstract of French Patent No. 2516512 discloses pyrido-indole derivatives useful for treating cardiac rhythm diseases.

SUMMARY OF THE INVENTION

The present invention provides a compound of formula I

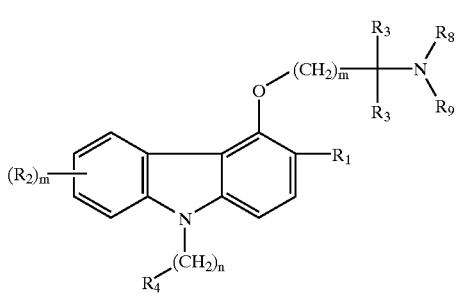

wherein $R_1$ is
(a) H,
(b) halo, or
(c) $C_{1-6}$ alkyl;

$R_2$ is
(a) H,
(b) halo,
(c) —OH,
(d) —CN,
(e) —$CF_3$,
(f) —O($C_{1-6}$)alkyl,
(g) $C_{1-6}$ alkyl,
(h) $C_{3-6}$ cycloalkyl,
(i) —$NR_5R_6$,
(j) —$CONR_5R_6$,
(k) —$SO_2NR_5R_6$,
(l) —$COOR_7$,
(m) —$OCF_3$, or
(n) phenyl, optionally substituted with halo, OH, O($C_{1-4}$) alkyl, or $C_{1-6}$ alkyl; each $R_3$ is independently
(a) H,
(b) $C_{1-6}$ alkyl, or
(c) $C_{3-6}$ cycloalkyl;

$R_4$ is
(a) aryl, or
(b) heteroaryl;

$R_5$ and $R_6$ are independently
(a) H,
(b) $C_{1-6}$ alkyl, or
(c) $C_{3-6}$ cycloalkyl;

$R_7$ is
(a) H,
(b) $C_{1-6}$ alkyl, or
(c) ($C_{1-3}$ alkyl)-phenyl wherein phenyl may be substituted with $R_3$;

$R_8$ and $R_9$ are independently
(a) H,
(b) $C_{1-6}$ alkyl, optionally substituted with aryl, hetroaryl, or $C_{3-6}$ cycloalkyl,
(c) $C_{2-6}$ alkenyl,
(d) $C_{3-6}$ cycloalkyl,
(e) $C_{2-6}$ alkyl substituted with $R_{10}$,
(f) —CHO, provided that only one of the $R_8$ and $R_9$ is CHO, the other one is H,
(g) aryl,
(h) heterocyclic, which is bonded via carbon atom to the nitrogen to which it is attached, or
(i) $R_8$ and $R_9$ taken together with the nitrogen to which they are attached form a heterocyclic ring wherein the heterocyclic ring may have one to two additional heteroatoms selected from the group consisting of oxygen, sulfur and N(Y) and wherein the carbon atoms of the heterocyclic ring is optionally substituted with one or two $R_{14}$;

$R_{10}$ is
(a) —OH,
(b) —O($C_{1-4}$ alkyl), optionally alkyl is substituted with OH,
(c) —O($C_{1-4}$ alkyl)-$NR_{11}R_{12}$,
(d) heterocyclic, or
(e) —$CO_2R_5$, $R_{11}$ and $R_{12}$ are independently,
(a) H, or
(b) $C_{1-4}$ alkyl;

aryl is phenyl or naphthyl, optionally substituted with one or more $R_{13}$; heteroaryl is a radical of a five- or six-membered monocyclic aromatic ring having one or two heteroatoms each selected from the group consisting of oxygen, sulfur, and N(X), or a radical of a nine- or ten-membered ortho-fused bicyclic aromatic ring having one, two or three heteroatoms each selected from the group consisting of oxygen, sulfur, and N(X); wherein carbon atoms of heteroaryl may be substituted with $R_{13}$;

heterocyclic is a radical of a five-, six-, or seven-membered partially-saturated or unsaturated heterocyclic ring having one, two or three heteroatoms selected from the group consisting of oxygen, sulfur and N(Y) wherein the carbon atoms of the heterocyclic ring may be substituted with $R_{14}$;

X is absent, H or $C_{1-4}$ alkyl;

Y is
(a) H,
(b) $C_{1-6}$ alkyl, optionally substituted with aryl or hetroaryl,
(c) $C_{3-6}$ cycloalkyl, or
(d) $C_{2-6}$ alkyl substituted with —OH, —O($C_{1-4}$ alkyl), —O($C_{1-4}$ alkyl)-$NR_{11}R_{12}$, —$CO_2R_5$, or NHCHO, or
(e) —OH;

$R_{13}$ is
(a) halo,
(b) —OH,
(c) —CN,
(d) —$CF_3$, (e) —O($C_{1-6}$)alkyl,
(f) $C_{1-6}$ alkyl,
(g) $C_{3-6}$ cycloalkyl,
(h) —$NR_5R_6$,
(i) —$CONR_5R_6$,
(j) —$SO_2NR_5R_6$,
(k) —$COOR_7$,
(l) —$OCF_3$, or
(m) phenyl, optionally substituted with halo, OH, O($C_{1-4}$) alkyl, or $C_{1-6}$ alkyl;

$R_{14}$ is
(a) $C_{1-6}$ alkyl,
(b) $C_{3-6}$ cycloalkyl,
(c) $C_{2-6}$ alkyl substituted with —OH, —O($C_{1-4}$ alkyl), —O($C_{1-4}$ alkyl)-$NR_{11}R_{12}$, or —$CO_2R_5$,
(d) —OH, or
(e) oxo (=O);

m is 1, 2, 3 or 4;

n is 1, 2, 3, or 4;

$C_{3-6}$ cycloalkyl in each of the above definitions, may be each and independently substituted with —OH, $C_{1-4}$ alkyl, or oxo (=O), and with the following provisos:
(a) when $R_4$ is 4-fluorophenyl, n is 1, m is 1, each $R_3$ is independently hydrogen, $R_8$ and $R_9$ is independently —$CH_2CH_3$, then $R_2$ cannot be fluoro or chloro at the C-6 position of formula I;
(b) when n is 1, m is 1, $R_2$, $R_3$, $R_8$ or $R_9$ is hydrogen, $R_4$ is 4-thiazolyl, then said 4-thiazolyl cannot be substituted with 4-chlorophenyl;
(c) when n is 1, m is 1, $R_2$, $R_3$, $R_8$ or $R_9$ is hydrogen, then $R_4$ is not 4-pyridyl;
(d) when n is 1, m is 1, $R_2$, $R_3$, $R_8$ or $R_9$ is hydrogen, then $R_4$ is not 2-bromophenyl or 4-bromophenyl.

In another aspect, the present invention also provides:

a pharmaceutical composition comprising a compound of formula I, or a pharmaceutically acceptable salt thereof, and a pharmaceutically acceptable excipient (the composition preferably comprises a therapeutically effective amount of the compound or salt), a method for treating a disease or condition in a mammal (e.g. a human) wherein a 5-HT receptor is implicated and modulation of a 5-HT function is desired comprising administering a therapeutically effective amount of a compound of formula I, or a pharmaceutically acceptable salt thereof to the mammal, a method for treating or preventing anxiety, obesity, depression, schizophrenia, a stress related disease (e.g. general anxiety disorder), panic disorder, a phobia, obsessive compulsive disorder, post-traumatic-stress syndrome, immune system depression, a stress induced problem with the gastrointestinal or cardiovascular system, eating disorders or sexual dysfunction in a mammal (e.g. a human) comprising administering a therapeutically effective amount of a compound of formula I, or a pharmaceutically acceptable salt thereof to the mammal, a method of treating or preventing diseases or disorders of the central nervous system such as: psychosis, paraphrenia, psychotic depression, mania, schizophrenia, schizophreniform disorders, schizoaffective disorder, delusional disorder, panic disorder, a phobia, obsessive compulsive disorder, post-traumatic-stress syndrome, immune system depression, a stress induced problem with the urinary, a stress related disease such as anxiety, migraine headache, drug addiction, convulsive disorders, personality disorders, post-traumatic stress syndrome, alcoholism, panic attacks, obsessive-compulsive disorders, sleep disorders, disorders of the gastrointestinal or cardiovascular system (e.g., stress incontinence), neurodegenerative disorders, autism, chemotherapy-induced vomiting, hypertension, cluster headaches, sexual dysfunction in a mammal (e.g. a human), addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance (including agitation in conditions associated with diminished cognition (e.g., dementia, mental retardation or delirium)), bipolar disorder, bulimia nervosa, chronic fatigue syndrome, conduct disorder, cyclothymic disorder, dysthymic disorder, fibromyalgia and other somatoform disorders, an inhalation disorder, an intoxication disorder, movement disorder (e.g., Huntington's disease or Tardive Dyskinesia), oppositional defiant disorder, peripheral neuropathy, post-traumatic stress disorder, premenstrual dysphoric disorder, a psychotic disorder (brief and long duration disorders, psychotic disorder due to medical condition, psychotic features), seasonal affective disorder, a specific developmental disorder, agitation disorder, selective serotonin reuptake inhibition (SSRI) "poop out" syndrome or a Tic disorder (e.g., Tourette's syndrome), comprising administering to a mammal (e.g. a human) in need of such treatment, a therapeutically effective amount of a compound of formula (I) or a pharmaceutically acceptable salt thereof, a compound of formula (I) or a pharmaceutically acceptable salt thereof for use in medical diagnosis or therapy (e.g. the treatment or prevention of 5-HT related central nervous system diseases or disorders), the use of a compound of formula (I) or a pharmaceutically acceptable salt thereof to prepare a medicament for treating or preventing 5-HT related central nervous system diseases or disorders such as anxiety, obesity, depression, schizophrenia, a stress related disease (e.g. general anxiety disorder), panic disorder, a phobia, obsessive compulsive disorder, post-traumatic-stress syndrome, immune system depression, a stress induced problem with the gastrointestinal or cardiovascular system, or sexual dysfunction in a mammal (e.g. a human), and a method for modulating 5-HT (e.g. 5-$HT_6$) receptor function, comprising contacting (in vitro or in vivo) the receptor with an effective inhibitory amount of a compound of formula I, or a pharmaceutically acceptable salt thereof.

The invention also provides novel intermediates and processes disclosed herein that are useful for preparing compounds of formula I.

DETAILED DESCRIPTION OF THE INVENTION

The compounds of the present invention are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

The carbon atom content of various hydrocarbon-containing moieties is indicated by a prefix designating the minimum and maximum number of carbon atoms in the moiety, i.e., the prefix $C_{i-j}$ indicates a moiety of the integer "i" to the integer "j" carbon atoms, inclusive. Thus, for example, $C_{1-7}$alkyl refers to alkyl of one to seven carbon atoms, inclusive.

Specific and preferred values listed below for radicals, substituents, and ranges, are for illustration only; they do not exclude other defined values or other values within defined ranges for the radicals and substituents.

The following definitions are used, unless otherwise described.

Halo is fluoro, chloro, bromo, or iodo.

Alkyl denotes both straight and branched groups; but reference to an individual radical such as "propyl" embraces only the straight chain radical, a branched chain isomer such as "isopropyl" being specifically referred to. Specifically, $C_{1-7}$ alkyl can be methyl, ethyl, propyl, isopropyl, butyl, iso-butyl, sec-butyl, pentyl, 3-pentyl, or hexyl.

Alkenyl denotes both straight and branched groups have at least one double bond.

$C_{3-6}$ cycloalkyl denotes a cycloalkyl having three to six carbon atoms. Specifically, $C_{3-6}$ cycloalkyl can be cyclopropyl, cyclobutyl, cyclopentyl, or cyclohexyl.

Aryl denotes a phenyl or a naphthyl radical. Optionally, aryl is substituted with one or more halo, OH, CN, $CF_3$, $O(C_{1-6})$alkyl, $C_{1-6}$ alkyl, $C_{3-6}$ cycloalkyl, $NR_5R_6$, $CONR_5R_6$, $SO_2NR_5R_6$, $COOR_7$, $OCF_3$, or phenyl which in turn may be substituted with halo, OH, $O(C_{1-4})$ alkyl, or $C_{1-6}$ alkyl. $R_5$ and $R_6$ are the same as summarized above.

Heteroaryl denotes a radical of a five- or six-membered monocyclic aromatic ring having one or two heteroatoms each selected from the group consisting of oxygen, sulfur, and N(X), or a radical of a nine- or ten-membered ortho-fused bicyclic aromatic ring having one, two or three heteroatoms each selected from the group consisting of oxygen, sulfur, and N(X); wherein X is absent, H or $C_{1-4}$ alkyl; wherein carbon atoms of heteroaryl may be substituted with one or more halo, OH, CN, $CF_3$, $O(C_{1-6})$alkyl, $C_{1-6}$ alkyl, $C_{3-6}$ cycloalkyl, $NR_5R_6$, $CONR_5R_6$, $SO_2NR_5R_6$, $COOR_7$, $OCF_3$, or phenyl which in turn may be substituted with halo, OH, $O(C_{1-4})$ alkyl, or $C_{1-6}$ alkyl. $R_5$, $R_6$ and $R_7$ are the same as summarized above. Examples of heteroaryl are pyridyl, thiophene, benzothiophene, benzofuran, benzimidazole, imidazole or thiazole.

Heterocyclic is a radical of a five-, six-, or seven-membered partially-saturated or unsaturated heterocyclic ring having one, two or three heteroatoms selected from the group consisting of oxygen, sulfur and N(Y) wherein the carbon atoms of the heterocyclic ring are optionally substituted with $R_{14}$. Y and $R_{14}$ are the same as summarized above. Examples of heterocyclic is azetidyl, pyrrolidinyl, piperidinyl, piperazinyl, morpholinyl, thiomorpholinyl, 1-benzyl-piperidinyl, 1-methyl-piperidinyl, dioxolane, imidazolidine, oxazolidinyl, oxathiolane, 4-hydroxyl-1-piperidinyl, 4-ethanol-1-piperazinyl-, 4-ethylformamide-1-piperazinyl-, or 4-methyl-1-piperazinyl.

Pharmaceutically acceptable salts denotes acid addition salts useful for administering the compounds of this invention and include hydrochloride, hydrobromide, hydroiodide, sulfate, phosphate, acetate, propionate, lactate, mesylate, maleate, malate, succinate, tartrate, citric acid, 2-hydroxyethyl sulfonate, fumarate, methanesulfonic acid salt and etc. Specifically, pharmaceutically acceptable salts can be maleate, methanesulfonic acid salt and etc.

Mammal denotes human and animals.

A specific value for $R_1$ is H, halo, or $C_{1-6}$ alkyl.

A specific value for $R_1$ is H.

A specific value for $R_2$ is H, halo, —OH, —CN, —$CF_3$, —$O(C_{1-6})$alkyl, $C_{1-6}$ alkyl, $C_{3-6}$ cycloalkyl, —$NR_5R_6$, —$CONR_5R_6$, —$SO_2NR_5R_6$, —$COOR_7$, or phenyl which may be substituted with halo, —OH, —$O(C_{1-4})$ alkyl, or $C_{1-6}$ alkyl; wherein $R_5$ and $R_6$ is H, $C_{1-6}$ alkyl, or $C_{3-6}$ cycloalkyl; wherein $R_7$ is $C_{1-6}$ alkyl, or $(C_{1-3}$ alkyl)-phenyl wherein phenyl may be substituted with $R_2$.

A specific value for $R_2$ is H, halo, or $C_{1-6}$ alkyl.

A specific value for $R_2$ is H, chloro, fluoro, or methyl.

A specific value for $R_2$ is H.

A specific value for $R_2$ is fluoro or methyl.

A specific value for each $R_3$ is independently H, $C_{1-6}$ alkyl, or $C_{3-6}$ cycloalkyl.

A specific value for each $R_3$ is independently H.

A specific value is wherein $R_8$ and $R_9$ are independently H, $C_{1-6}$ alkyl (optionally substituted with aryl, heteroaryl or $C_{3-6}$ cycloalkyl), $C_{2-6}$ alkenyl, $C_{3-6}$ cycloalkyl, $C_{2-6}$ alkyl substitute with $R_{10}$, —CHO (provided that only one of the $R_8$ and $R_9$ is —CHO, the other one is hydrogen), aryl, heterocyclic wherein heterocyclic is bonded via carbon atom to the nitrogen to which it is attached, or $R_8$ and $R_9$ taken together with the nitrogen to which they are attached form a heterocyclic ring wherein the heterocyclic ring may have one to two additional heteroatoms selected from the group consisting of oxygen, sulfur and N(Y) and wherein the carbon atoms of the heterocyclic ring are optionally substituted with one or two $R_{13}$; wherein $R_{10}$, and Y are as defined above, wherein each $C_{3-6}$ cycloalkyl is optionally substituted with —OH, $C_{1-4}$ alkyl, or oxo.

A specific value is wherein $R_8$ is H, and $R_9$ is H, $C_{1-6}$ alkyl, $C_{2-4}$ alkenyl, $C_{1-6}$ alkyl substituted with phenyl, wherein phenyl is optionally substituted with fluoro or chloro.

A specific value is wherein $R_8$ is H, and $R_9$ is $C_{1-6}$ alkyl substituted with $C_{3-6}$ cycloalkyl, wherein cycloalkyl is optionally substituted with —H, $C_{1-4}$ alkyl or oxo.

A specific value is wherein $R_8$ is H, and $R_9$ is $C_{2-6}$ alkyl substituted with —OH, —$O(C_{1-4}$ alkyl), —$O(C_{1-4}$ alkyl-OH) or —$CO_2C_{1-4}$ alkyl.

A specific value is wherein $R_8$ is H, and $R_9$ is cyclopropyl, cyclobutyl, cyclopentyl, or cyclohexyl, all of which may be substituted with —OH, $C_{1-4}$ alkyl, oxo, or —CHO.

A specific value is wherein $R_8$ is H, and $R_9$ is $C_{1-6}$ alkyl substituted with phenyl, pyridyl, thiophene, benzothiophene, benzofuran, benzimidazole, imidazole or thiazole.

A specific value is wherein $R_8$ is H, and $R_9$ is heterocyclic wherein heterocyclic is bonded via carbon atom to the nitrogen to which it is attached.

A specific value is wherein $R_8$ is H, and $R_9$ is pyridyl methyl, benzimidazole methyl, or 1-benzyl-piperidinyl.

A specific value is wherein $R_8$ is H; and $R_9$ is $C_{2-6}$ alkyl substituted with azetidyl, pyrrolidinyl, piperidinyl, piperazinyl, morpholinyl, thiomorpholinyl, 1-benzyl-piperidinyl, 1-methyl-piperidinyl, dioxolane, imidazolidine, oxazolidinyl, oxathiolane, 4-hydroxyl-1-piperidinyl, 4-ethanol-1-piperazinyl-, 4-ethylformamide-1-piperazinyl-, or 4-methyl-1-piperazinyl.

A specific value is wherein $R_8$ and $R_9$ taken together with the nitrogen to which they are attached form a heterocyclic ring wherein the heterocyclic ring may have one to two additional heteroatoms selected from the group consisting of oxygen, sulfur and N(Y), wherein Y is the same as defined in claim 1.

A specific value is wherein $R_8$ and $R_9$ taken together with the nitrogen to which they are attached form 4-morpholinyl, 1-pyrrolidinyl, 1-piperidinyl, 1-piperazinyl, 4-hydroxyl-1-piperidinyl, 4-ethanol-1-piperazinyl-, 4-ethylformamide-1-piperazinyl-, or 4-methyl-1-piperazinyl.

A specific value for $R_8$ and $R_9$ are independently H, methyl, ethyl, propyl, 1-propanol, 2-propenyl, 1-pentanol, 2-methyl-1-propanol, 2-butanol, 1-ethanol, ethoxyl-1- ethanol, —CH₂CH₂CO₂ethyl, 2-methoxyethyl, 4-chlorophenethyl, or 4-fluorophenethyl.

A specific value is wherein $R_8$ and $R_9$ are both hydrogen atoms.

A specific value is wherein $R_8$ is H; and $R_9$ is methyl.

A specific value is wherein $R_8$ and $R_9$ taken together with the nitrogen to which they are attached form 4-methyl-1-piperazinyl.

A specific value for $R_4$ is aryl, or heteroaryl; wherein aryl or heteroaryl are as defined as herein above.

A specific value for $R_4$ is phenyl.

A specific value for $R_4$ is pyridyl, thiophene, benzothiophene, benzofuran, benzimidazole, imidazole, thiazole pyridyl, thiophene, benzothiophene, benzofuran, benzimidazole, imidazole or thiazole.

A specific value for $R_4$ is 2-methyl-1,3-thiazol-4-yl, or 5-chloro-1-benzothiophn-3-yl.

A specific value for m is one.

Examples of the present invention includes:

a) N-{2-[(9-benzyl-9H-carbazol-4-yl)oxy]ethyl}-N,N-diethylamine,
b) N-{2-[(9-benzyl-8-chloro-9H-carbazol-4-yl)oxy]ethyl}-N,N-diethylamine,
c) N-(2-{[8-chloro-9-(4-fluorobenzyl)-9H-carbazol-4-yl]oxy}ethyl)-N,N-diethylamine,
d) N-{2-[(9-benzyl-8-methyl-9H-carbazol-4-yl)oxy]ethyl}-N,N-diethylamine,
e) N,N-diethyl-N-(2-{[9-(4-fluorobenzyl)-8-methyl-9H-carbazol-4-yl]oxy}ethyl)amine,
f) N-{2-[(9-benzyl-9H-carbazol-4-yl)oxy]ethyl}-N-(2-pyridinylmethyl)amine,
g) N-{2-[(9-benzyl-8-fluoro-9H-carbazol-4-yl)oxy]ethyl}-N,N-diethylamine,
h) 9-benzyl-4-[2-(4-morpholinyl)ethoxy]-9H-carbazole,
i) 2-(4-{2-[(9-benzyl-9H-carbazol-4-yl)oxy]ethyl}-1-piperazinyl)-1-ethanol,
j) 3-({2-[(9-benzyl-9H-carbazol-4-yl)oxy]ethyl}amino)-1-propanol,
k) N-{2-[(9-benzyl-9H-carbazol-4-yl)oxy]ethyl}-2-propen-1-amine
l) N-{2-[(9-benzyl-9H-carbazol-4-yl)oxy]ethyl}-3-(4-morpholinyl)-1-propanamine,
m) 5-({2-[(9-benzyl-9H-carbazol-4-yl)oxy]ethyl}amino)-1-pentanol,
n) N-{2-[(9-benzyl-9H-carbazol-4-yl)oxy]ethyl}-1-propanamine,
o) N-{2-[(9-benzyl-9H-carbazol-4-yl)oxy]ethyl}-N-propyl-1-propanamine,
p) 1-benzyl-N-{2-[(9-benzyl-9H-carbazol-4-yl)oxy]ethyl}-4-piperidinamine,
q) 2-({2-[(9-benzyl-9H-carbazol-4-yl)oxy]ethyl}amino)-2-methyl-1-propanol,
r) 2-[(9-benzyl-9H-carbazol-4-yl)oxy]-N-(4-chlorophenethyl)-1-ethanamine,
s) 2-[(9-benzyl-9H-carbazol-4-yl)oxy]-N-(cyclohexylmethyl)-1-ethanamine,
t) 2-[(9-benzyl-9H-carbazol-4-yl)oxy]-N-[2-(4-morpholinyl)ethyl]-1-ethanamine,
u) 1-({2-[(9-benzyl-9H-carbazol-4-yl)oxy]ethyl}amino)-2-butanol,
v) 2-[(9-benzyl-9H-carbazol-4-yl)oxy]-N-(4-fluorophenethyl)-1-ethanamine,
w) 2-[2-({2-[(9-benzyl-9H-carbazol-4-yl)oxy]ethyl}amino)ethoxy]-1-ethanol,
x) (1S,2S)-2-({2-[(9-benzyl-9H-carbazol-4-yl)oxy]ethyl}amino)cyclohexanol,
y) ethyl 3-({2-[(9-benzyl-9H-carbazol4-yl)oxy]ethyl}amino)propanoate,
z) N-{2-[(9-benzyl-9H-carbazol-4-yl)oxy]ethyl}cyclobutanamine,
aa) 2-(4-{2-[(9-benzyl-9H-carbazol-4-yl)oxy]ethyl}-1-piperazinyl)ethylformamide,
bb) N-(1H-benzimidazol-2-ylmethyl)-2-[(9-benzyl-9H-carbazol-4-yl)oxy]-1-ethanamine,
cc) 1-{2-[(9-benzyl-9H-carbazol-4-yl)oxy]ethyl}-4-piperidinol,
dd) 9-benzyl-4-[2-(4-methyl-1-piperazinyl)ethoxy]-9H-carbazole,
ee) N-{2-[(9-benzyl-9H-carbazol-4-yl)oxy]ethyl}-N-cyclopropylamine,
ff) N-{2-[(9-benzyl-9H-carbazol-4-yl)oxy]ethyl}-N,N-dimethylamine,
gg) N-{2-[(9-benzyl-9H-carbazol -4-yl)oxy]ethyl}formamide,
hh) N-{2-[(9-benzyl-9H-carbazol-4-yl)oxy]ethyl}-N-methylamine, or its maleic acid salt,
ii) 2-[(9-benzyl-9H-carbazol-4-yl)oxy]ethylamine,
jj) N-{2-[(9-benzyl-9H-carbazol-4-yl)oxy]ethyl}-N-(2-methoxyethyl)aamine,
kk) N-ethyl-N-{[(1-phenyl-1,2-dihydro[1,4]oxazino[2,3,4-jk]carbazol-7-yl)oxy]ethyl}amine, or its maleic acid salt,
ll) 9-benzyl-4-[2-(1-pyrrolidinyl)ethoxy]-9H-carbazole,
mm) 9-benzyl-4-[2-(1-piperidinyl)ethoxy]-9H-carbazole,
nn) 9-benzyl-4-[2-(1-piperazinyl)ethoxy]-9H-carbazole,
oo) 2-[(9-benzyl-8-fluoro-9H-carbazol-4-yl)oxy]ethylamine,
pp) N,N-diethyl-N-(2-{[8-fluoro-9-(4-fluorobenzyl)-9H-carbazol-4-yl]oxy}ethyl)amine,
qq) N-{2-[(9-benzyl-6-chloro-9H-carbazol-4-yl)oxy]ethyl}-N,N-diethylamine,
rr) N-{2-[(9-benzyl-6-fluoro-9H-carbazol-4-yl)oxy]ethyl}-N,N-diethylamine,
ss) N-{2-[(9-benzyl-6-methyl-9H-carbazol-4-yl)oxy]ethyl}-N,N-diethylamine,
tt) 2-[(9-benzyl-6-methyl-9H-carbazol-4-yl)oxy]ethylamine,
uu) N-{2-[(9-benzyl-6-methyl-9H-carbazol-4-yl)oxy]ethyl}-N-methylamine,
vv) N,N-diethyl-N-(2-{[9-(4-fluorobenzyl)-6-methyl-9H-carbazol-4-yl]oxy}ethyl)amine,
ww) 2-({2-[(9-benzyl-9H-carbazol-4-yl)oxy]ethyl}amino)-1-ethanol or its maleic acid salt,
xx) 2-({9-[(5-Chloro-1-benzothiophen-3-yl)methyl]-9H-carbazol-4-yl}oxy)ethylamime or its methane sulfonate salt,
yy) 2-({9-[(2-Methyl-1,3-thiazol-4-yl)methyl]-9H-carbazol-4-yl}oxy)ethylamine or its methane sulfonate salt,
zz) 2-[(9-benzyl-3-chloro-9H-carbazol-4-yl)oxy]ethylamine, methanesulfonate salt,
aaa) 2-{[9-(3-bromobenzyl)-9H-carbazol-4-yl]oxy}ethylamine, maleic acid salt,
bbb) 2-{[9-(3-fluorobenzyl)-9H-carbazol-4-yl]oxy}ethylamine, maleic acid salt,
ccc) 2-{[9-(4-methylbenzyl)-9H-carbazol-4-yl]oxy}ethylamine, maleic acid salt,
ddd) 2-{[9-(2-fluorobenzyl)-9H-carbazol-4-yl]oxy}ethylamine, maleic acid salt,
eee) 2-{[9-(3-methoxybenzyl)-9H-carbazol-4-yl]oxy}ethylamine, maleic acid salt,
fff) 2-{[9-(3,5-dimethoxybenzyl)-9H-carbazol-4-yl]oxy}ethylamine, maleic acid salt,
ggg) 2-{[9-(3-methylbenzyl)-9H-carbazol-4-yl]oxy}ethylamine, maleic acid salt, hhh) 2-{[9-(2-methylbenzyl)-9H-carbazol-4-yl]oxy}ethylamine, maleic acid salt,
iii) 2-[(9-benzyl-6-methoxy-9H-carbazol-4-yl)oxy]ethylamine, or
jjj) 2-[(9-benzyl-7-methoxy-9H-carbazol-4-yl)oxy]ethylamine.

It will be appreciated by those skilled in the art that compounds of the invention may contain a chiral center, therefore, they may be isolated in optically active or racemic forms. Some compounds may exhibit polymorphism. It is to be understood that the present invention encompasses any racemic, optically active, polymorphic, tautomeric, or stereoisomeric form, or mixture thereof, of a compound of the invention, which possesses the useful properties described herein. It is well known in the art to prepare optically active forms (for example, by resolution of the racemic form by recrystallization techniques, by synthesis from optically-active starting materials, by chiral synthesis, or by chromatographic separation (using a chiral stationary phase, for example)) and to determine 5-HT$_6$ activity using the standard tests described herein, or using other similar tests which are well known in the art.

The following Schemes describe the preparation of compounds of the present invention. All of the starting materials are commercially available or prepared by procedures described in these schemes or by procedures that would be well known to one of ordinary skill in organic chemistry. The variables used in the Schemes are as defined above or as in the claims.

As shown in Chart A, hydrazines 3 can be prepared from commercially available anilines 1. Aniline 1 is stirred in an acidic medium such as TFA, acetic acid, or aq. sulfuric acid. A nitrite such as sodium nitrite, isoamylnitrite, or n-butylnitrite is added to give nitroso aniline 2. Nitroso aniline 2 is reduced with lithium aluminum hydride in ether or THF to give hydrazine 3. For a discussion of additional methods of preparing 3, see Sandler, S. R.; Karo, W. *Organic Functional Group Preparations;* Academic Press: New York, 1983; Vol. I, 2nd Ed., pp. 434–465. Hydrazone 4 is prepared from hydrazine 3 and cyclohexane-1,3-dione in solvents such as water, alcohols, or dichloromethane. Hydrazone 4 is then treated under the conditions of the Fischer indole synthesis using an acid and a solvent such as acetic acid, toluene, ethanol, or others, to give tetrahydrocarbazole 5. Alternatively, hydrazine 3 and cyclohexane-1,3-dione may be reacted under Fischer indole conditions to directly give tetrahydrocarbazole 5. Many additional methods for the Fischer indole synthesis are given in Sundberg, R. J.; *Indoles,* Academic Press: London; 1996, and in Hughes, D. L. Progress in the Fischer Indole Reaction: A Review. *Org. Prep. Proceed. Int.* 1993, 25, 609–632. The nitrogen of tetrahydrocarbazole 5 is alkylated by methods well known to those versed in the art. For example, treatment of tetrahydrocarbazole 5 with a base such as sodium hydride, followed by an alkyl halide such as benzyl chloride or benzyl bromide, gives benzyl tetrahydrocarbazole 6.

Treatment of compound 6 in a single step using Raney nickel on Pd/carbon in solvents such as cumene, mesitylene, 1,2,3-trimethylbenzene, 1,2,4-trimethylbenzene, decalin, carbitol, or diphenyl ether at temperatures between 130–270° C. provides phenol 9 directly. Alternatively, benzyl tetrahydrocarbazole 6 is first treated with a copper (n) halide, preferably CuCl$_2$ or CuBr$_2$, in solvents such as DMF, acetonitrile, EtOAc, chloroform, acetic acid, or acetic acid/water at temperatures between 50 and 120° C. to give halo tetrahydrocarbazoles 7 and 8. For a reference to this reaction, see Matsumoto, M.; Ishida, Y.; Watanabe, N. *Heterocycles* 1985, 23, 165–170. A third useful method is treatment of benzyl tetrahydrocarbazole 6 with pyridinium bromide perbromide or phenyltrimethylammonium tribromide in solvents such as DMF, acetonitrile, or THF to give halo tetrahydrocarbazoles 7 and 8. Halo tetrahydrocarbazoles 7 and 8 may be separated and carried on individually in the next steps, or they may be carried forward as a mixture to phenols 9 and 10 and separated at that time. Halo tetrahydrocarbazoles 7 and 8 (separately or together) are then treated with lithium chloride or lithium bromide (anhydrous LiCl or LiBr is preferred, but hydrated forms also may be used) in the presence of lithium carbonate in a solvent such as DMF at 110–130° C. to give phenols 9 and 10.

Charts B and D disclose some of the ways phenols 9 and 10 may be alkylated with various alkylating agents; and Chart C discloses further transformations of carbazole amine 13 to give alkyl amines 15, 16, and 17 directly or after several steps. Which method is used will depend on the type of amine that is desired and on the availability of alkylating agents. For clarity, only 13 is depicted in Chart C, but the reaction scheme applies equally well to 14. In chart D, only phenol 9 is depicted, but the reaction scheme applies equally well to phenol 10.

In Chart B, X refers to a halogen atom. Phenols 9 and 10 are alkylated with chloro or bromoethyl amine in the presence of bases such as sodium hydride, potassium carbonate, cesium carbonate, or sodium carbonate in solvents such as DMF, acetonitrile, or acetone at room temperature to 120° C. to give carbazole amines 13 and 14 directly. Alternatively, phenols 9 and 10 are alkylated with chloro- or bromoacetonitrile in the presence of bases such as sodium hydride, potassium carbonate, cesium carbonate, or sodium carbonate in solvents such as DMF, acetonitrile, or acetone at room temperature to 120° C. to give nitrites 11 and 12. Reduction of nitrites 11 and 12 with borane in THF or borane-methyl sulfide complex in THF at room temperature to 80° C. gives carbazole amines 13 and 14 (R8 and R9 are hydrogen atoms). Other methods for the reduction of the nitrite group to an amine may be found in March, *J. Advanced Organic Chemistry,* 3rd ed., John Wiley and Sons: New York: 1985.

Chart C discloses further functionalization of carbazole amine 14 by several methods. In Chart C, Q refers to hydrogen, alkyl, or aryl. Z refers to hydrogen or alkyl. One method is acylation with acylating agents such as ethyl formate, acetic anhydride, and the like to give acyl carbazole 15. The carbonyl function of acyl carbazole 15 is reduced to an alkyl group using reagents such as borane in THF or borane-methyl sulfide complex in THF at room temperature to 80° C. to give monoalkylamino carbazole 16; or using lithium aluminum hydride in ethereal solvents to effect the reduction to monoalkylamino carbazole 16. A second method is reductive amination of 14 with an equivalent amount of an aldehyde or ketone in the presence of reducing agents such as sodium cyanoborohydride or sodium triacetoxyborohydride in solvents such as dichloromethane, dichloroethane, and THF at 0 to 80° C., or Pd/C under a hydrogen atmosphere in solvents such as methanol, ethanol, or ethyl acetate to give monoalkylamino carbazole 16. A third method is alkylation of carbazole amine 14 with alkyl halides or mesylates or tosylates in the presence of base in solvents such as THF, acetonitrile, dichloromethane, DMF and the like using methods well known to those versed in the art to give monoalkylamino carbazole 16.

When dialkylamino carbazole 17 is desired, a second equivalent of the same or a different aldehyde, ketone, or alkylating agent, depending on the method used, is added to monoalkylamino carbazole 16 using the conditons described above. Alternatively, dialkylaminocarbazole 17 may be prepared directly from 14 using two equivalents of the aldehyde, ketone, or alkylating agent.

Chart D describes another method of preparing mono- or dialkylamino carbazole 21, wherein phenol 9 is alkylated by methods well-known to those versed in the art to give carbazole halide 18 or carbazole alcohol 19. In Chart D, L refers to a leaving group such as halo atom or a sulfonate group. The alcohol group of carbazole alcohol 19 is converted to a leaving group with methane sulfonyl halide or toluene sulfonyl halide to give carbazole sulfonate 20. The mesyl or tosyl group of carbazole sulfonate 20 or carbazole halide 18 is then displaced by amines to give amino carbazole 21.

Pharmaceutically acceptable salts may be obtained using standard procedures well known in the art, for example by mixing a compound of the present invention with a suitable acid.

Compounds of the present invention can conveniently be administered in a pharmaceutical composition containing the compound in combination with a suitable excipient. Such pharmaceutical compositions can be prepared by methods and contain excipients which are well known in the art. A generally recognized compendium of such methods and ingredients is Remington's Pharmaceutical Sciences by E. W. Martin (Mark Publ. Co., 15th Ed., 1975). The compounds and compositions of the present invention can be administered parenterally (for example, by intravenous, intraperitoneal or intramuscular injection), topically, orally, or rectally.

For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The compounds or compositions can also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

Pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions can be prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The compound is conveniently administered in unit dosage form; for example, containing about 0.05 mg to about 500 mg, conveniently about 0.1 mg to about 250 mg, most conveniently, about 1 mg to about 150 mg of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compositions can conveniently be administered orally, sublingually, transdermally, or parenterally at dose levels of about 0.01 to about 150 mg/kg, preferably about 0.1 to about 50 mg/kg, and more preferably about 0.1 to about 30 mg/kg of mammal body weight.

For parenteral administration the compounds are presented in aqueous solution in a concentration of from about 0.1 to about 10%, more preferably about 0.1 to about 7%. The solution may contain other ingredients, such as emulsifiers, antioxidants or buffers.

The exact regimen for administration of the compounds and compositions disclosed herein will necessarily be dependent upon the needs of the individual subject being treated, the type of treatment and, of course, the judgment of the attending practitioner.

Generally, compounds of the invention are 5-HT ligands. The ability of a compound of the invention to bind or act at a 5-HT receptor, or to bind or act selectively at a specific 5-HT receptor subtype can be determined using in vitro and in vivo assays that are known in the art. As used herein, the term "bind selectively" means a compound binds at least 2 times, preferably at least 10 times, and more preferably at least 50 times more readily to a given 5-HT subtype than to one or more other subtypes. Preferred compounds of the invention bind selectively to one or more 5-HT receptor subtypes.

The ability of a compound of the invention to act as a 5-HT receptor agonist or antagonist can also be determined using in vitro and in vivo assays that are known in the art. The invention provides compounds of formula I that act as either agonists or as antagonists of one or more 5-HT receptor subtypes.

5-HT$_6$ Receptor Binding Assay

Growth of Cells and Membrane Preparation

Hela cells containing the cloned human 5-HT$_6$ receptor were acquired from Dr. David R. Sibley's laboratory in National Institute of Health (see Sibley, D. R., *J. Neurochemistry*, 66, 47–56, 1996). Cells were grown in high glucose Dulbecco's modified Eagle's medium, supplemented with L-glutamine, 0.5% sodium pyruvate, 0.3% penicillin-streptomycin, 0.025% G-418 and 5% Gibco fetal bovine serum and then were harvested, when confluent, in cold phosphate-buffered saline.

Harvested intact cells were washed once in cold phosphate-buffered saline. The cells were pelleted and resuspended in 100 ml of cold 50 mM Tris, 5 mM EDTA and 5 mM EGTA, pH 7.4. Homogenization was with a Vir Tishear generator, 4 cycles for 30 seconds each at setting 50. The homogenized cells were centrifuged at 700 RPM (1000×g) for 10 minutes and the supernatant was removed. The pellet was resuspended in 100 ml of the above buffer and rehomogenized for 2 cycles. The rehomogenized cells were then centrifuged at 700 RPM (1000×g) for 10 minutes and the supernatant was removed. The combined supernatant (200ml) was centrifuged at 23,000 RPM (80,000×g) for 1 hour in a Beckman Rotor (42.1 Ti). The membrane pellet was resupended in 50–8-ml of assay buffer containing HEPES 20 mM, MgCl$_2$ 10 mM, NaCl 150 mM, EDTA 1 mM, pH 7.4 and stored frozen in aliqouts at −70° C.

5-HT$_6$ Receptor Binding Assay

The radioligand binding assay used [$^3$H]-lysergic acid diethylamide (LSD). The assay was carried out in Wallac 96-well sample plates by the addition of 11 μl of the test sample at the appropriate dilution (the assay employed 11 serial concentrations of samples run in duplicate), 11 μl of radioligand, and 178 μl of a washed mixture of WGA-coated SPA beads and membranes in binding buffer. The plates were shaken for about 5 minutes and then incubated at room temperature for 1 hour. The plates were then loaded into counting cassettes and counted in a Wallac MicroBeta Trilux scintillation counter.

Binding Constant (Ki) Determination

Eleven serial dilutions of test compounds were distributed to assay plates using the PE/Cetus Pro/Pette pipetter. These dilutions were, followed by radioligand and the bead-membrane mixture prepared as described above. The specifically bound cpm obtained were fit to a one-site binding model using GraphPad Prism ver. 2.0. Estimated IC$_{50}$ values were converted to Ki values using the Cheng-Prusoff equation (Cheng, Y. C. et al., *Biochem. Pharmacol.*, 22, 3099–108, 1973). The Ki values obtained from the assay are shown in Table 1.

TABLE 1

5-HT$_6$ receptor Binding Assay Data

| EXAMPLE NO. | Ki (nM) |
|---|---|
| 1 | 24 |
| 2 | 6 |
| 3 | 22 |
| 4 | 18 |
| 5 | 38 |
| 6 | 69 |
| 7 | 2.6 |
| 8 | 398 |
| 9 | 62 |
| 10 | 20 |
| 11 | 23 |
| 12 | 184 |
| 13 | 43 |
| 14 | 40 |
| 15 | 394 |
| 16 | 148 |
| 17 | 164 |
| 18 | 356 |
| 19 | 311 |
| 20 | 37 |
| 21 | 72 |
| 22 | 81 |
| 23 | 32 |
| 24 | 85 |
| 25 | 40 |
| 26 | 47 |
| 27 | 138 |
| 28 | 72 |
| 29 | 11 |
| 30 | 12 |
| 31 | 21 |
| 32 | — |
| 33 | 211 |
| 34 | 5.7 |
| 35 | 23 |
| 36 | 16 |
| 37 | 11 |
| 38 | 6.9 |
| 39 | 12 |
| 40 | 88 |

TABLE 1-continued

5-HT$_6$ receptor Binding Assay Data

| EXAMPLE NO. | Ki (nM) |
| --- | --- |
| 41 | 2.4 |
| 42 | 20 |
| 43 | 182 |
| 44 | 180 |
| 45 | 6.6 |
| 46 | 6.1 |
| 47 | 2.2 |
| 48 | 123 |
| 49 | 4.5 |
| 50 | 138 |
| 51 | 113 |
| 52 | 24 |
| 53 | 127 |
| 54 | 101 |
| 55 | 482 |
| 56 | 119 |
| 57 | 110 |
| 58 | — |
| 59 | 20 |
| 60 | |
| 61 | 27 |
| 62 | 60 |

The compounds and their preparations of the present invention will be better understood in connection with the following examples, which are intended as an illustration of and not a limitation upon the scope of the invention.

EXAMPLES OF PREFERRED EMBODIMENTS

Preparation 1 1,2,3,9-Tetrahydro-4H-carbazol-4-one

To a solution of 1,3-cyclohexane dione (1.99 g, 17.7 mmol) in water (55 mL) is added phenylhydrazine (1.92 g, 17.7 mmol) in 10 mL of water. A gummy solid quickly formed, which after completion of the addition is scrapped with a spatula to give a solid. The solid is collected, washed with water, and dried in a vacuum oven to give 3.0 g of a tan solid. After drying, the tan solid is stirred at reflux in TFA (25 mL) overnight. Upon cooling, TFA is removed in vacuo and water is added to the residue. The resulting solid is collected, washed with water, and dried to give 1.82 g (55%) of the title compound; mp 218–220° C.; IR (drift) 3150, 3130, 3104, 3093, 3056, 2976, 2954, 2944, 1607, 1577, 1466, 1413, 1251, 1178, 755 cm$^{-1}$; $^1$H NMR (CDCl$_3$) δ2.26, 2.64, 3.00, 7.26, 7.35, 8.21, 8.74. Anal. Calcd for C$_{12}$H$_{11}$NO: C, 77.81; H, 5.99; N, 7.56. Found: C, 77.82; H, 6.15; N, 7.54.

Preparation 2 9-Benzyl-1,2,3,9-tetrahydro-4H-carbazol-4-one

Sodium hydride (60% in oil; 0.207 g, 5.18 mmol) is washed three times with hexane. DMF (3 mL) is added, followed by 36B added in portions. A moderate exotherm ensued; THF (3 mL) is added. After ten minutes benzyl bromide (1.047 g, 6.12 mmol) is added. After stirring for 4 h, an additional 0.1 g of benzyl bromide is added. The mixture is stirred overnight and then the solvents are removed; the residue is partitioned between CH$_2$C$_2$ and aq. sodium bicarbonate. The organic layers are dried over sodium sulfate. Chromatography on silica gel (150 mL) using CH$_3$OH—CH$_2$Cl$_2$ (1/99) as eluent, followed by re-chromatography of mixed fractions using EtOAc-hexane (30/70), gave 1.023 g (79%) of the title compound; mp 157.0–157.5° C.; IR (drift) 2940, 1636, 1610, 1530, 1484, 1464, 1445, 1399, 1357, 1187, 1133, 749, 742, 731, 698 cm$^{-1}$; $^1$H NMR (CDCl$_3$) δ2.23, 2.60, 2.88, 5.34, 7.03, 7.2–7.3, 8.30. Anal. Calcd for C$_{19}$H$_{17}$NO: C, 82.88; H, 6.22; N, 5.09. Found: C, 82.51; H, 6.21; N, 5.13.

Preparation 3 9-Benzyl-9H-carbazol-4-ol

To a mixture of 9-Benzyl-1,2,3,9-tetrahydro-4H-carbazol-4-one (3.89 g, 14.13 mmol), THF (20 mL) in THF (20 mL) and DMF (15 mL) is added pyridinium hydrobromide perbromide (5.42 g, 16.96 mmol) as a solution in DMF (5 mL). After stirring for 5 h at room temperature, TLC (EtOAc-hexane, 20/80) showed little or no reaction had occurred, so the mixture is stirred at 70° C. for 4 h and then allowed to cool (and stir the remainder of the night). The solvents then are removed and the residue is partitioned between Et$_2$O and brine, dil. Na$_2$S$_2$O$_3$, and brine. The aqueous layer is removed and CH$_2$Cl$_2$ is added to the organic layer (from which solids had begun to precipitate). The organic layers are dried over MgSO$_4$ and taken to dryness. Without further purification, the crude product is stirred with LiBr (2.67 g, 31 mmol) and Li$_2$CO$_3$ (2.07 g, 28 mmol) in DMF (50 mL) at 100° C. for 45 min, and then at reflux for 3 h. After cooling, the solvent is removed and the residue is partitioned between CH$_2$Cl$_2$ and water. The organic layers are dried over sodium sulfate and concentrated to dryness. The residue is chromatographed on silica gel (250 mL) using EtOAc-heptane (15/85)/CH$_2$Cl$_2$ (6:1) as eluent to give 2.78 g of solid; mp 119–121.5° C.; IR (drift) 3353, 1602, 1485, 1458, 1337, 1328, 1279, 1230, 1138, 1104, 780, 748, 735, 714, 700 cm$^{-1}$; $^1$H NMR (CDCl$_3$) δ5.32, 5.50, 6.60, 6.97, 7.14, 7.26, 7.3–7.4, 8.33. Anal. Calcd for C$_{19}$H$_{15}$NO: C, 83.49; H, 5.53; N, 5.12. Found: C, 82.35; H, 5.51; N, 5.06.

Example 1

N-{2-[(9-Benzyl-9H-carbazol-4-yl)oxy]ethyl}-N,N-diethylamine

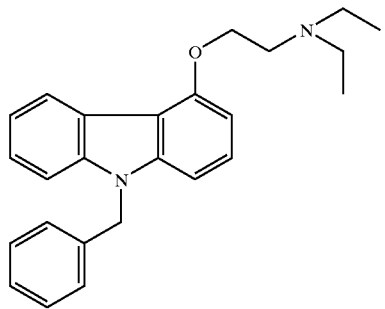

A mixture of 9-benzyl-9H-Carbazol-4-ol (0.0305 g, 0.1116 mmol), potassium carbonate (0.0308 g, 0.2232 mmol), and DMF (1.0 mL) is stirred at 100° C. Diethylaminoethyl chloride hydrochloride (0.0230 g, 0.1339 mmol) is added in aliquots over 40 min. After 2.3 h, an additional 0.032 g of potassium carbonate and 0.023 g of diethylaminoethyl chloride hydrochloride are added. The mixture is stirred overnight and then the solvent is removed and the residue partitioned between CH$_2$Cl$_2$ and aq. sodium bicarbonate. The organic layers are dried over sodium sulfate. Chromatography on silica gel (15 mL) using acetone-hexane (20/80) gave 0.0382 g of the title compound as a solid; mp 79–80.5° C.; IR (drift) 2965, 1581, 1457, 1439, 1356, 1342, 1333, 1268, 1147, 1112, 1053, 782, 750, 729, 713 cm$^{-1}$; $^1$H NMR (CDCl$_3$) δ1.14, 2.75, 3.13, 4.36, 5.50, 6.71, 6.98, 7.12, 7.2–7.4, 8.38. Anal. Calcd for $C_{25}H_{28}N_2O$: C, 80.61; H, 7.58; N, 7.52. Found: C, 79.90; H, 7.52; N, 7.43.

Preparation 4 8-Chloro-1,2,3,9-tetrahydro-4H-carbazol-4-one

2-Chlorophenylhydrazine hydrochloride (1.6885 g, 0.0094 mol) is added portion-wise to a solution of 1,3-cyclohexanedione (1.0316 g, 0.0092 mol) in water (17.4 mL). The mixture is allowed to stir for three days at room temperature. The solids are collected by filtration, washed with water and vacuum dried at 50° C. for 30 min and then overnight at room temperature to give the hydrazone. The hydrazone is then heated at reflux in trifluoroacetic acid (9 mL). After stirring overnight, the mixture is cooled and then partitioned between ice water and dichloromethane. The organic layer is washed with aq. sodium bicarbonate and the aqueous layer is backwashed with dichloromethane. The combined organic layers are then dried over sodium sulfate and concentrated to a foam. Product is precipitated from the foam by adding dichloromethane, methanol and acetone. After filtering the solids, the filtrate is concentrated to a foam and again more product is precipitated using acetone/dichloromethane (2/98). The solids are collected by filtration and the filtrate is chromatographed on silica gel (150 mL) using acetone/dichloromethane (2/98 and 4/96) to give product. All of the solids are combined and recrystallized from dichloromethane/methanol/hexane to give 0.3724 g (18%) of a first crop and 0.1092 g (5%) of a second crop of the title compound; mp >247° C.; MS (ESI−) for $C_{12}H_{10}ClNO$ m/z 217.9 (M−H)$^-$; IR (drift) 3155, 3142, 3105, 3080, 2943, 1633, 1613, 1473, 1174, 1139, 1071, 1015, 858, 791, 744 cm$^{-1}$; $^1$H NMR (CDCl$_3$) δ2.28, 2.61, 3.03, 7.22, 8.11, 8.60. Anal. Calcd for $C_{12}H_{10}ClNO$: C, 65.61; H, 4.59; N, 6.38. Found: C, 65.48; H, 4.62; N, 6.38.

Preparation 5 9-Benzyl-8-chloro-1,2,3,9-tetrahydro-4H-carbazol-4-one

8-Chloro-1,2,3,9-tetrahydro-4H-carbazol-4-one (0.2019 g, 0.92 mmol) is added to a slurry of pentane-washed NaH (0.0275 g, 0.68 mmol) in DMF (1 mL) and after stirring 22 min benzyl bromide (0.13 mL, 0.0011 mol) is added. Starting material remained after 30 min, so additional NaH (0.0140 g, 0.35 mmol) and DMF (1 mL) are added and the mixture is allowed to stir overnight. The mixture is then partitioned between aq. sodium bicarbonate and ethyl acetate and the organic layer is dried over sodium sulfate and concentrated to dryness. The resulting solids are recrystallized from 30% ethyl acetate/hexane and dichloromethane to give 0.1942 g (68%) of the title compound; mp 161–162° C.; MS (ESI+) for $C_{19}H_{16}ClNO$ m/z 310.1 (M+H)$^+$; IR (drift) 1644, 1605, 1538, 1484, 1462, 1447, 1425, 1357, 1188, 1106, 793, 784, 737, 725, 699 cm$^{-1}$; $^1$H NMR (CDCl$_3$) δ2.22, 2.59, 2.85, 5.82, 6.95, 7.18, 7.28, 8.28. Anal. Calcd for $C_{19}H_{16}ClNO$: C, 73.66; H, 5.20; N, 4.52. Found: C, 73.41; H, 5.17; N, 4.57.

Preparation 6 9-Benzyl-8-chloro-9H-carbazol-4-ol

Pyridinium bromide perbromide (0.1856 g, 0.58 mmol) is added to a solution of 9-benzyl-8-chloro-1,2,3,9-tetrahydro-4H-carbazol-4-one in THF (0.7 mL) and DMF (0.5 mL) and the mixture is heated to 75° C. After stirring for 5.5 h, THF is removed under reduced pressure and the residue is partitioned between dichloromethane and brine. The combined organic layers are washed with dilute sodium sulfate/brine and the aqueous layer is backwashed with dichloromethane. The combined organic layers are dried over magnesium sulfate and concentrated under reduced pressure to give a residue. A mixture of the resulting residue, lithium bromide (0.0940 g, 0.0011 mol), lithium carbonate (0.0772 g, 0.0010 mol) and DMF (2 mL) is heated at 120° C. for two hours. The DMF is then removed under high vacuum and the residue is partitioned between dichloromethane and water. The combined organic layers are dried over sodium sulfate and concentrated to an oil. The oil is chromatographed on silica gel (80 mL) using 15% ethyl acetate in heptane/dichloromethane (6:1) to give 0.1060 g (72%) of the title compound: mp 163–165.5° C.; MS (ESI−) for $C_{19}H_{14}ClNO$ m/z 306.1 (M−H)$^-$; IR (drift) 3537, 1632, 1587, 1452, 1417, 1351, 1339, 1311, 1268, 1208, 1112, 1073, 789, 734, 729 cm$^{-1}$; $^1$H NMR (CDCl$_3$) δ5.42, 5.98, 6.59, 6.93, 7.09, 7.15–7.28, 7.36, 8.29. Anal. Calcd for $C_{19}H_{14}ClNO$: C, 74.15; H, 4.59; N, 4.55. Found: C, 73.22; H, 4.53; N, 4.62.

Example 2

N-{2-[(9-Benzyl-8-chloro-9H-carbazol-4-yl)oxy]ethyl}-N,N-diethylamine

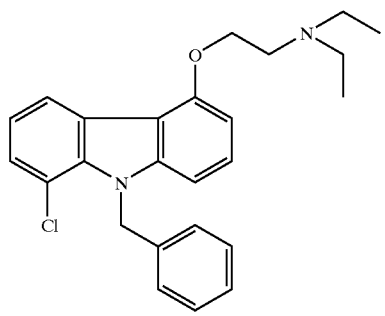

9-Benzyl-8-chloro-9H-carbazol-4-ol (0.0826 g, 0.27mmol), 2-diethylaminoethylchloride hydrochloride (0.0719 g, 0.42 mmol), potassium carbonate (0.1157 g, 0.84 mmol), sodium iodide (0.0031 g, 0.021 mmol) and DMF (1 mL) are heated at 85° C. for 4 h. After the mixture had cooled, it is partitioned between water and ether. The combined organic layers are dried over magnesium sulfate and concentrated to an oil. The oil is chromatographed on silica gel (30 mL) using methanol/dichloromethane (1/99 to 2/98 to 4/96) to give 0.0675 g (62%) of the title compound: mp 73.5–75° C.; MS (ESI+) for $C_{25}H_{27}ClN_2O$ m/z 407.3 (M+H)$^+$; IR (drift) 2966, 1588, 1499, 1454, 1413, 1355, 1337, 1266, 1124, 1027, 789, 732, 727, 717, 697 cm$^{-1}$; $^1$H NMR (CDCl$_3$) δ1.13, 2.72, 3.10, 4.33, 5.99, 6.71, 6.96, 7.10, 7.15–7.26, 7.33, 8.33. Anal. Calcd for $C_{25}H_{27}ClN_2O$: C, 73.79; H, 6.69; N, 6.88. Found: C, 73.47; H, 6.81; N, 6.76.

Preparation 7 8-Chloro-9-(4-fluorobenzyl)-1,2,3,9-tetrahydro-4H-carbazol-4-one

8-Chloro-1,2,3,9-tetrahydro-4H-carbazol-4-one (0.1973 g, 0.90 mmol) is added to a slurry of pentane-washed NaH (0.0286 g, 0.72 mmol) in DMF (1 mL) and, after stirring for 22 min, p-fluorobenzyl bromide (0.14 mL, 0.0011 mol) is added. Starting material remained after 30 min, so additional NaH (0.0166 g, 0.42 mmol) and DMF (1.8 mL) are added. The mixture is stirred for 1 h, at which time the mixture is partitioned between aq. sodium bicarbonate and ethyl acetate. The organic layer is dried over sodium sulfate and concentrated to dryness. The resulting solids are recrystallized from 30% ethyl acetate/hexane and dichloromethane to give 0.2088 g (71%) of the title compound; mp 166–166.5°

C.; MS (ESI+) for C$_{19}$H$_{15}$ClFNO m/z 328.1 (M+H)$^+$; IR (drift) 1639, 1607, 1510, 1485, 1449, 1426, 1413, 1226, 1189, 1157, 1108, 1095, 830, 790, 734 cm$^{-1}$; $^1$H NMR (CDCl$_3$) δ2.22, 2.59, 2.84, 5.78, 6.97, 7.19, 8.27. Anal. Calcd for C$_{19}$H$_{15}$ClFNO: C, 69.62; H, 4.61; N, 4.27. Found: C, 69.44; H, 4.55; N, 4.34.

Preparation 8 8-Chloro-9-(4-fluorobenzyl)-9H-carbazol-4-ol

Pyridinium bromide perbromide (0.1988 g, 0.62 mmol) is added to a solution of 8-chloro-9-(4-fluorobenzyl)-1,2,3,9-tetrahydro-4H-carbazol-4-one in THF (0.7 mL) and DMF (0.5 mL) and the mixture is heated to 75° C. After stirring for 5.5 h, THF is removed under reduced pressure and the residue is partitioned between dichloromethane and brine. The combined organic layers are washed with dilute sodium sulfate/brine and the aqueous layer is backwashed with dichloromethane. The combined organic layers are dried over magnesium sulfate and concentrated under reduced pressure to give a residue. A mixture of the resulting residue, lithium bromide (0.0976 g, 0.0011 mol), lithium carbonate (0.0762 g, 0.0010 mol) and DMF (2 mL) is heated at 120° C. for two hours. The DMF is then removed under high vacuum and the residue is partitioned between dichloromethane and water. The combined organic layers are dried over sodium sulfate and concentrated to an oil. The oil is chromatographed on silica gel (80 mL) using 15% ethyl acetate in heptane/dichloromethane (6:1) to give 0.1199 g (72%) of the title compound; mp 142–145° C.; MS (ESI–) for C$_{19}$H$_{13}$ClFNO m/z 324.1 (M–H)$^-$; IR (drift) 3521, 1591, 1508, 1457, 1416, 1351, 1337, 1311, 1269, 1226, 1218, 1110, 852, 791, 736 cm$^{-1}$; $^1$H NMR (CDCl$_3$) δ5.38, 5.94, 6.60, 6.93, 7.06, 7.18, 7.26, 7.36, 8.29. Anal. Calcd for C$_{19}$H$_{13}$ClFNO: C, 70.05; H, 4.02; N, 4.30. Found: C, 69.26; H, 4.05; N, 4.20.

Example 3

N-(2-{[8-Chloro-9-(4-fluorobenzyl)-9H-carbazol-4-yl]oxy}ethyl)-N,N-diethylamine

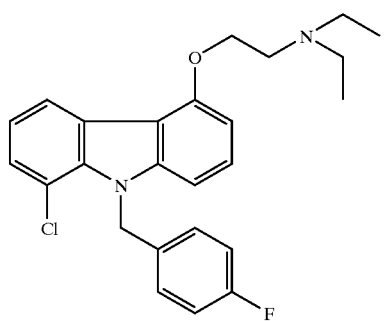

8-Chloro-9-(4-fluorobenzyl)-9H-carbazol-4-ol (0.1038 g, 0.32mmol), 2-diethylaminoethylchloride hydrochloride (0.0831 g, 0.48 mmol), potassium carbonate (0.1248 g, 0.90 mmol), sodium iodide (0.0037 g, 0.025 mmol) and DMF (1 mL) are heated at 85° C. for 5.5 h. After the mixture had cooled, it is partitioned between water and ether. The combined organic layers are dried over magnesium sulfate and concentrated to an oil. The oil is chromatographed on silica gel (50 mL) using methanol/dichloromethane (1/99, 2/98 and 4/96) to give 0.0741 g (55%) of the title compound; mp 104.5–105.5° C.; MS (ESI+) for C$_{25}$H$_{26}$ClFN$_2$O m/z 425.1 (M+H)$^+$; IR (drift) 2966, 2932, 1590, 1506, 1455, 1414, 1354, 1334, 1270, 1221, 1157, 1124, 822, 791, 734 cm$^{-1}$; $^1$H NMR (CDCl$_3$) δ1.19, 2.82, 3.20, 4.43, 5.95, 6.73, 6.94, 7.04, 7.16, 7.36, 8.30. Anal. Calcd for C$_{25}$H$_{26}$ClFN$_2$O: C, 70.66; H, 6.17; N, 6.59; Cl, 8.34. Found: C, 70.30; H, 6.13; N, 6.54.

Preparation 9 8-Methyl-1,2,3,9-tetrahydro-4H-carbazol-4-one

O-Tolylhydrazine hydrochloride (1.3957 g, 0.0091 mol) is added in portions to a solution of 1,3-cyclohexanedione (1.0113 g, 0.0090 mol) in water (17.5 mL). The mixture is allowed to stir overnight at room temperature. The resulting slurry is filtered, washed with water and vacuum dried at 50° C. for 30 min and then overnight at room temperature to give the hydrazone. The hydrazone is then heated at reflux in trifluoroacetic acid (9 mL). After stirring for 3 h, the mixture is cooled and then partitioned between ice water and dichloromethane. The organic layer is washed with aq. sodium bicarbonate and the aqueous layer is backwashed with dichloromethane. The combined organic layers are then dried over sodium sulfate and concentrated to a foam. Product is precipitated from the foam by adding methanol/dichloromethane (2/98). After collecting the solids by filtration, the filtrate is concentrated and again more product is precipitated using methanol/dichloromethane (2/98). These solids are collected by filtration and the filtrate is chromatographed on silica gel (150 mL) using acetone/dichloromethane (2/98, 4/96 and 8/92) to give product. All of the solids are combined and recrystallized from dichloromethane, methanol and hexane to give 0.3550 g, (20%) for a first crop and 0.1261 g (7%) for a second crop of the title compound; mp >247° C.; MS (ESI–) for C$_{13}$H$_{134}$NO m/z 198.0 (M–H)$^-$; IR (drift) 3187, 3159, 3088, 2940, 1612, 1475, 1454, 1410, 1216, 1183, 1140, 1068, 1013, 791, 756 cm$^{-1}$; $^1$H NMR (CDCl$_3$) δ2.26, 2.50, 2.60, 3.00, 7.04, 7.17, 8.06, 8.39. Anal. Calcd for C$_{13}$H$_{13}$NO: C, 78.36; H, 6.58; N, 7.03. Found: C, 78.05; H, 6.61; N, 7.05.

Preparation 10 9-Benzyl-8-methyl-1,2,3,9-tetrahydro-4H-carbazol-4-one

8-Methyl-1,2,3,9-tetrahydro-4H-carbazol-4-one (0.1967 g, 0.99 mmol) is added to a slurry of pentane-washed NaH (0.0485 g, 0.0012 mol) in DMF (2 mL) and after stirring for 30 min, benzyl bromide (0.14 mL, 0.0012 mol) is added. After 3 h starting material still remained, so additional benzyl bromide (0.015 mL, 0.013 mmol) is added and the mixture is stirred overnight at room temperature. The mixture is then partitioned between aq. sodium bicarbonate and ethyl acetate and the organic layer is dried over sodium sulfate and concentrated to dryness. The resulting solids are recrystallized from ethyl acetate/hexane/dichloromethane to give 0.2076 g (73%) of the title compound; mp 165–166° C.; MS (ESI+) for C$_{20}$H$_{19}$NO m/z 290.2 (M+H)$^+$; IR (drift) 2940, 1637, 1599, 1538, 1494, 1462, 1447, 1416, 1357, 1322, 1121, 787, 752, 727, 697 cm$^{-1}$; $^1$H NMR (CDCl$_3$) δ2.21, 2.51, 2.59, 2.82, 5.58, 6.89, 6.95, 7.16, 7.29, 8.23. Anal. Calcd for C$_{20}$H$_{19}$NO: C, 83.01; H, 6.62; N, 4.84. Found: C, 82.53; H, 6.62; N, 4.86.

Preparation 11 9-Benzyl-8-methyl-9H-carbazol-4-ol

Pyridinium bromide perbromide (0.2032 g, 0.64 mmol) is added to a mixture of 9-benzyl-8-methyl-1,2,3,9-tetrahydro-4H-carbazol-4-one in THF (0.7 mL) and DMF (0.5 mL) and the mixture is heated to 75° C. After stirring for 8 h, THF is removed under reduced pressure and the residue is partitioned between dichloromethane and brine. The combined organic layers are washed with dilute sodium thiosulfate/ brine and the aqueous layer is backwashed with dichloromethane. The combined organic layers are dried over magnesium sulfate and concentrated under reduced pressure to give a residue. A mixture of the resulting residue, lithium bromide (0.1005 g, 0.0012 mol), lithium carbonate (0.0768 g, 0.0010 mol) and DMF (2 mL) is heated at 120° C. for two hours. The DMF is removed under high vacuum and the residue is partitioned between dichloromethane and water. The combined organic layers are dried over sodium sulfate and concentrated to an oil. The oil is chromatographed on silica gel (75 mL) using ethyl acetate/heptane (10/90) to give 0.0888 g (59%) of the title compound. The product is then recrystallized from ethyl acetate/hexane; MS (ESI+) for $C_{20}H_{17}NO$ m/z 288.1 (M+H)$^+$; IR (drift) 3537, 1587, 1492, 1451, 1351, 1338, 1315, 1271, 1236, 1205, 963, 792, 745, 729, 720 cm$^{-1}$; $^1$H NMR (CDCl$_3$) δ2.64, 5.32, 5.76, 6.58, 6.88, 7.02, 7.15–7.26, 8.24. Anal. Calcd for $C_{20}H_{17}NO$: C, 83.59; H, 5.96; N, 4.87. Found: C, 80.86; H, 5.73; N, 4.72.

Example 4

N-{2-[(9-Benzyl-8-methyl-9H-carbazol-4-yl)oxy]ethyl}-N,N-diethylamine

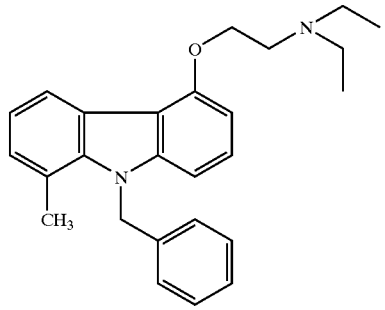

9-Benzyl-8-methyl-9H-carbazol-4-ol (0.0566 g, 0.20 mmol), 2-diethylaminoethylchloride hydrochloride (0.0505 g, 0.29 mmol), potassium carbonate (0.0922 g, 0.67 mmol), sodium iodide (0.0029 g, 0.019 mmol) and DMF (1 mL) are heated at 85° C. for 4 h. After the mixture had cooled, it is partitioned between water and ether. The combined organic layers are dried over magnesium sulfate and concentrated to an oil. The oil is chromatographed on silica gel (15 mL) using methanol/dichloromethane (1/99 to 2/98 to 4/96) to give 0.0248 g (32%) of the title compound; MS (ESI+) for $C_{26}H_{30}N_2O$ m/z 387.2 (M+H)$^+$; IR (drift) 2966, 1585, 1497, 1449, 1353, 1336, 1268, 1251, 1140, 1106, 1069, 791, 743, 725, 715 cm$^{-1}$; $^1$H NMR (CDCl$_3$) δ1.18, 2.64, 2.81, 3.20, 4.41, 5.77, 6.69, 6.91, 6.99, 7.13, 7.22–7.33, 8.28. Anal. Calcd for $C_{26}H_{30}N_2O$: C, 80.79; H, 7.82; N, 7.25. Found: C, 79.00; H, 7.76; N, 7.10.

Preparation 12 9-(4-Fluorobenzyl)-8-methyl-1,2,3,9-tetrahydro-4H-carbazol-4-one

8-Methyl-1,2,3,9-tetrahydro-4H-carbazol-4-one (0.1967 g, 0.99 mmol) is added to a slurry of pentane-washed NaH (0.0449 g, 0.0011 mol) in DMF (2 mL). After stirring for 30 min, p-fluorobenzyl bromide (0.15 mL, 0.0012 mol) is added. Starting material is still present after 3 h, so additional p-fluorobenzyl bromide (0.015 mL, 0.12 mmol) is added and the mixture is stirred overnight. The mixture is then partitioned between aq. sodium bicarbonate and ethyl acetate and the organic layer is dried over sodium sulfate and concentrated to dryness. The resulting solids are chromatographed on silica gel (75 mL) using methanol/dichloromethane (2/98). The impure fractions are rechromatographed on silica gel (60 mL) using methanol/dichloromethane (2/98). The pure fractions are combined and recrystallized from ethyl acetate/hexane/dichloromethane to give 0.1021 g (34%) of the title compound; mp 154–155° C.; MS (ESI+) for $C_{20}H_{18}FNO$ m/z 308.2 (M+H)$^+$; IR (drift) 1635, 1602, 1539, 1510, 1462, 1449, 1414, 1226, 1159, 835, 826, 801, 786, 756, 747 cm$^{-1}$; $^1$H NMR (CDCl$_3$) δ2.21, 2.51, 2.59, 2.81, 5.55, 6.87, 6.98, 7.17, 8.23. Anal. Calcd for $C_{20}H_{18}FNO$: C, 78.15; H, 5.90; N, 4.56. Found: C, 77.72; H, 5.95; N, 4.64.

Preparation 13 9-(4-Fluorobenzyl)-8-methyl-9H-carbazol-4-ol

Pyridinium bromide perbromide (0.0800 g, 0.25 mmol) is added to a solution of 9-(4-fluorobenzyl)-8-methyl-1,2,3,9-tetrahydro-4H-carbazol-4-one in THF (0.4 mL) and DMF (0.3 mL) and the mixture is heated to 75° C. After stirring for 8 h, THF is removed under reduced pressure and the residue is partitioned between dichloromethane and brine. The combined organic layers are washed with dilute sodium sulfate/brine and the aqueous layer is backwashed with dichloromethane. The combined organic layers are dried over magnesium sulfate and concentrated under reduced pressure to give a residue. A mixture of the resulting residue, lithium bromide (0.0391 g, 0.45 mmol), lithium carbonate (0.0358 g, 0.48 mmol) and DMF (1.2 mL) is heated at 120° C. for two hours. The DMF is then removed under high vacuum and the residue is partitioned between dichloromethane and water. The combined organic layers are dried over sodium sulfate and concentrated to an oil. The oil is chromatographed on silica gel (30 mL) using ethyl acetate/heptane (10/90) to give 0.0321 g (52%) of the title compound; MS (ESI+) for $C_{20}H_{16}FNO$ m/z 306.1 (M+H)$^+$; IR (drift) 3545, 1588, 1508, 1453, 1408, 1336, 1316, 1269, 1234, 1227, 1203, 819, 791, 743, 720 cm$^{-1}$; $^1$H NMR (CDCl$_3$) δ2.63, 5.36, 5.72, 6.58, 6.85, 6.96, 7.15–7.22, 8.25. Anal. Calcd for $C_{20}H_{16}FNO$: C, 78.67; H, 5.28; N, 4.59. Found: C, 74.98; H, 5.05; N, 4.37.

Example 5

N,N-Diethyl-N-(2-{[9-(4-fluorobenzyl)-8-methyl-9H-carbazol-4-yl]oxy}ethyl)amine

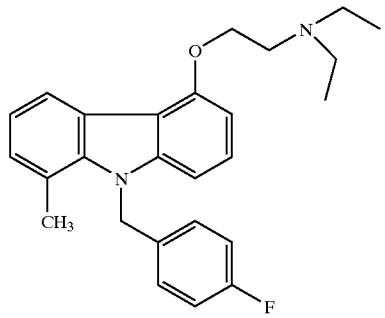

9-(4-Fluorobenzyl)-8-methyl-9H-carbazol-4-ol (0.0176 g, 0.058mmol), 2-diethylaminoethylchloride hydrochloride (0.0144 g, 0.084 mmol), potassium carbonate (0.0332 g, 0.24 mmol), sodium iodide (0.0008 g, 0.0053 mmol) and DMF (1 mL) are heated at 85° C. for 4 h. After the mixture had cooled, it is partitioned between water and ethyl acetate. The aqueous layer is also washed with dichloromethane. The combined organic layers are dried over magnesium sulfate and concentrated to an oil. The oil is chromatographed on silica gel (10 mL) using methanol/dichloromethane (1/99 and 2/98) to give 0.0148 g (55%) of the title compound; MS (ESI+) for $C_{26}H_{29}FN_2O$ m/z 405.2 (M+H)$^+$; $^1$H NMR (CDCl$_3$) δ1.23, 2.65, 2.88, 3.26, 4.47, 5.75, 6.73, 6.95, 7.15, 7.33, 8.29. Anal. Calcd for $C_{26}H_{29}FN_2O$: C, 77.20; H, 7.22; N, 6.93. Found: C, 73.47; H, 7.06; N, 6.53.

Preparation 14 9-Benzyl-4-(2-bromoethoxy)-9H-carbazole

To a mixture of 9-benzyl-9H-Carbazol-4-ol (2.46 g, 9.00 mmol), potassium carbonate (5.11 g, 27.0 mmol), and DMF (10 mL) is added dibromoethane (3.90 mL, 45.0 mmol). The mixture is stirred at 80° C. for 4.5 h and then allowed to cool and stir the remainder of the night. The mixture is then stirred at 85° C.; after about 2 h an additional 1.0 mL of dibromoethane is added. After 5.5 h the mixture is cooled and the solvent and excess dibromoethane are removed in vacuo. The residue is partitioned between Et$_2$O, water, and brine. The organic layers are dried over MgSO$_4$ and taken to dryness. Chromatography on silica gel (250 mL) using EtOAc-heptane (10/90 to 20/80) to give 1.80 g (53%) after crystallization from CH$_2$Cl$_2$-hexane; IR (drift) 1583, 1458, 1446, 1342, 1333, 1281, 1270, 1245, 1154, 1147, 1114, 783, 753, 734, 719 cm$^{-1}$; $^1$H NMR (CDCl$_3$) δ3.87, 4.58, 5.51, 6.66, 7.02, 7.12, 7.2–7.4, 8.43. Anal. Calcd for $C_{21}H_{18}BrNO$: C, 66.33; H, 4.77; N, 3.68; Br, 21.01. Found: C, 66.30; H, 4.76; N, 3.62.

Example 6

N-{2-[(9-Benzyl-9H-carbazol-4-yl)oxy]ethyl}-N-(2-pyridinylmethyl)amine

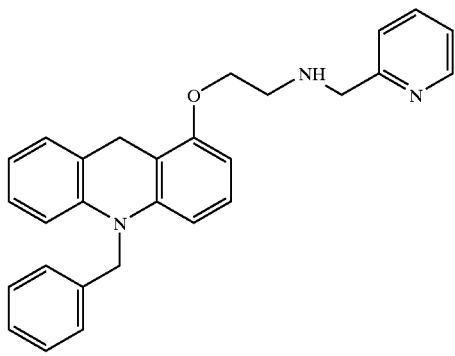

A mixture of 9-benzyl-4-(2-bromoethoxy)-9H-carbazole (0.0622 g, 0.1635 mmol), diisopropylethylamine (0.0211 g, 0.1635 mmol), 2-(2-aminomethylpyridine (0.0531 g, 0.4907 mmol), and DMF (0.5 mL) is stirred at 100° C. for 30 min. After cooling, the solvent is removed and the residue partitioned between CH$_2$Cl$_2$ and aq. sodium bicarbonate. The organic layers are dried over sodium sulfate; chromatography on silica gel (40 mL) using CH$_3$OH—CH$_2$Cl$_2$ (2/98) gave 0.0539 g (81%) of the title compound; IR (drift) 1586, 1457, 1342, 1269, 1237, 1153, 1145, 1118, 1047, 782, 776, 753, 745, 718, 710 cm$^{-1}$; $^1$H NMR (CDCl$_{CH3}$) δ3.32, 4.13, 4.44, 5.51, 6.70, 6.99, 7.12, 7.2–7.4, 7.66, 8.39, 8.60. Anal. Calcd for $C_{27}H_{25}N_3O$: C, 79.58; H, 6.18; N, 10.31. Found: C, 79.66; H, 6.41; N, 10.28.

Preparation 15 8-Fluoro-1,2,3,9-tetrahydro-4H-carbazol-4-one

2-Fluorophenylhydrazine hydrochloride (4.74 g, 0.0291 mol) is added in portions to a solution of 1,3-cyclohexanedione (3.20 g, 0.0285 mol) in water (60 mL). The mixture is allowed to stir overnight at room temperature. The resulting solids are collected by filtration, washed with water followed by a small hexane wash and vacuum dried at 50° C. for 40 min and then overnight at room temperature, to give the hydrazone. The hydrazone, p-toluene sulfonic acid monohydrate (5.8557 g, 0,031 mol) and trimethylbenzene (43 mL) are heated at 160° C. for 52 min. After cooling, the mixture is partitioned between water and dichloromethane. The aqueous layer is also washed once with chloroform. The combined organic layers are washed with aq. sodium bicarbonate, dried over sodium sulfate and concentrated to a residue. The resulting residue is chromatographed on silica gel (400 mL) using ethyl acetate/hexane (20/80, 40/60 and 60/40 to give 0.8221 g (15%) of the title compound; mp 225–226° C.; MS (ESI−) for $C_{12}H_{10}FNO$ 202.0 (M−H)$^-$; IR (drift) 3117, 3078, 3049, 3015, 2952, 2867, 1615, 1475, 1235, 1219, 1184, 1143, 864, 786, 735 cm$^{-1}$; $^1$H NMR (CDCl$_3$) δ2.27, 2.61, 3.02, 6.95, 7.16, 7.97, 8.82. Anal. Calcd for $C_{12}H_{10}FNO$: C, 70.93; H, 4.96; N, 6.89. Found: C, 71.40; H, 5.00; N, 6.92.

Preparation 16 9-Benzyl-8-fluoro-1,2,3,9-tetrahydro-4H-carbazol-4-one

8-Fluoro-1,2,3,9-tetrahydro-4H-carbazol-4-one (2.23 g, 0.011 mol) is added to a slurry of pentane-washed NaH (0.59 g, 0.015 mol) in DMF (18 mL) and after stirring for 20 min, benzyl bromide (1.7 mL, 0.014 mol) is added. The mixture is stirred for 1 h at which time the mixture is partitioned between water and ethyl acetate. The combined organic layers are dried over sodium sulfate and concentrated to dryness. The resulting residue is chromatographed on silica gel (200 mL) using methanol/dichloromethane (1/99). The solids are then recrstallized from ethyl acetate/dichloromethane/hexane to give 2.25 g (70%) of the title compound; mp 183–184° C.; MS (ESI−) for $C_{19}H_{16}FNO$ m/z 292.1 (M−H)$^-$; IR (drift) 1639, 1631, 1495, 1459, 1434, 1359, 1246, 1219, 1193, 1125, 798, 789, 736, 730, 698 cm$^{-1}$; $^1$H NMR (CDCl3) δ2.23, 2.58, 2.87, 5.51, 6.92, 7.03, 7.16, 7.29, 8.07. Anal. Calcd for $C_{19}H_{16}FNO$: C, 77.80; H, 5.50; N, 4.78. Found: C, 77.58; H, 5.59; N, 4.79.

Preparation 17 9-Benzyl-8-fluoro-9H-carbazol-4-ol

Pyridinium bromide perbromide (2.9945 g, 0.0094 mol) is added to a mixture of 9-benzyl-8-fluoro-1,2,3,9-tetrahydro-4H-carbazol-4-one (2.1145 g, 0.0072 mol) in THF (22 mL) and DMF (16 mL) and the mixture is heated to 75° C. After stirring for 5.5 h, THF is removed under reduced pressure and the residue is partitioned between ethyl acetate and brine. The combined organic layers are washed with dilute sodium thiosulfate/brine and the aqueous layer is back-washed with ethyl acetate. The combined organic layers are dried over magnesium sulfate and concentrated under reduced pressure to give a residue. The residue is recrystallized from ethyl acetate/heptane and the resulting solids are combined with lithium bromide (1.1338 g, 0.013 mol), lithium carbonate (0.8831 g, 0.012 mol), and DMF (24 mL)

and heated to 120° C. After 1.5 h, the mixture is partitioned between ethyl acetate and brine. The combined organic layers are washed with dilute brine and then dried over sodium sulfate and concentrated to an oil. The oil is chromatographed on silica gel (150 mL) using dichloromethane (100) to give 1.0857 g (52%) of the title compound; mp 155–156° C.; MS (ESI−) for $C_{19}H_{14}FNO$ m/z 290.1 (M−H)−; IR (drift) 3524, 1581, 1498, 1456, 1432, 1343, 1318, 1272, 1239, 1134, 966, 790, 731, 714, 698 cm$^{-1}$; $^1$H NMR (CDCl3) δ5.33, 5.69, 6.59, 6.98, 7.14, 7.25, 8.10. Anal. Calcd for $C_{19}H_{14}FNO$: C, 78.33; H, 4.84; N, 4.81. Found: C, 77.67; H, 4.90; N, 4.71.

Example 7

N-{2-[(9-Benzyl-8-fluoro-9H-carbazol-4-yl)oxy]ethyl}-N,N-diethylamine

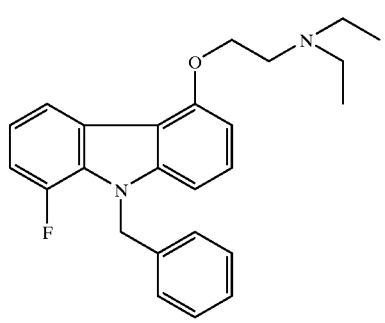

9-Benzyl-8-fluoro-9H-carbazol-4-ol (0.0273 g, 0.0940 mmol), 2-diethylaminoethylchloride hydrochloride (0.0237 g, 0.14 mmol), potassium carbonate (0.0396 g, 0.29 mmol), sodium iodide (0.0013 g, 0.0087 mmol) and DMF (1 mL) are heated at 80° C. for 3 h. After the mixture had cooled, it is partitioned between water and ethyl acetate. The organic layer is dried over magnesium sulfate and concentrated to an oil. The oil is chromatographed on silica gel (20 mL) using methanol/dichloromethane (1/99 to 2/98 to 3/97) to give 0.0206 g (56%) of the title compound; mp 60–60.5° C.; MS (ESI+) for $C_{25}H_{27}FN_2O$ m/z 391.3 (M+H)+; $^1$H NMR (CDCl$_3$) δ1.17, 2.79, 3.17, 4.39, 5.53, 6.73, 7.02, 7.13, 7.25, 7.38, 8.15. Anal. Calcd for $C_{25}H_{27}FN_2O$: C, 76.89; H, 6.97; N, 7.17. Found: C, 76.33; H, 7.18; N, 7.13.

Preparation 18 2-[(9-Benzyl-8-fluoro-9H-carbazol-4-yl)oxy]acetonitrile

A mixture of 9-benzyl-8-fluoro-9H-carbazol-4-ol (1.0775 g, 0.0037 mol), potassium carbonate (0.6284 g, 0.0046 mol), bromoacetonitrile (0.6 mL, 0.0086 mol) and DMF (12 mL) is stirred at room temperature for 4 h. The mixture is then partitioned between water and dichloromethane. The aqueous layer is also washed with ethyl acetate. The combined organic layers are dried over sodium sulfate and concentrated to a residue, which is then partitioned between water and ethyl acetate. The combined organic layers are dried over magnesium sulfate and concentrated to a residue. The resulting residue is chromatographed on silica gel (100 mL) using ethyl acetate/hexane (20/80) followed by dichloromethane (100 %). The solids are recrystallized from ethyl acetate/heptane to give 0.8869 g (73%) of the title compound; mp 134–134.25° C.; MS (ESI+) for $C_{21}H_{15}FN_2O$ m/z 353.1 (M+Na)+; IR(drift) 1578, 1500, 1458, 1439, 1369, 1344, 1335, 1323, 1278, 1235, 1144, 1080, 793, 739, 695 cm$^{-1}$; $^1$H NMR (CDCl$_3$) δ5.05, 5.71, 6.75, 7.16, 7.24, 7.41, 8.07. Anal. Calcd for $C_{21}H_{15}FN_2O$: C, 76.35; H, 4.58; N, 8.48. Found: C, 76.15; H, 4.63; N, 8.35.

Examples 8–32

A mixture of 9-benzyl-4-(2-bromoethoxy)-9H-carbazole (0.020 g, 0.0526 mmol), an appropriate amine (0.0631 mmol), diisopropylethylamine (0.0631 mmol), and DMF (0.2 or 0.4 mL) is stirred in 7 mL capped glass vials (at room temperature for volatile amines and at 70° C. for the remainder). When TLC showed most of the starting material had been consumed (3–4 days for room temperature reactions and overnight for heated reactions), the vials (minus caps) are placed in a vacuum oven for removal of solvent. The residues are chromatographed on silica gel (using disposable glass Pasteur pipettes as columns), eluting with $CH_3OH$—$CH_2Cl_2$ (2/98 to 8/92, depending on the polarity of the product. Product fractions are combined and the eluent is allowed to evaporate.

Example 8

9-benzyl-4-[2-(4-morpholinyl)ethoxy]-9H-carbazole ms (m+H) at 387

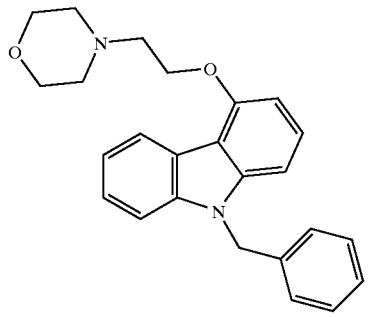

Example 9

2-(4-{2-[(9-benzyl-9H-carbazol-4-yl)oxy]ethyl}-1-piperazinyl)-1-ethanol ms (m+H) at 430

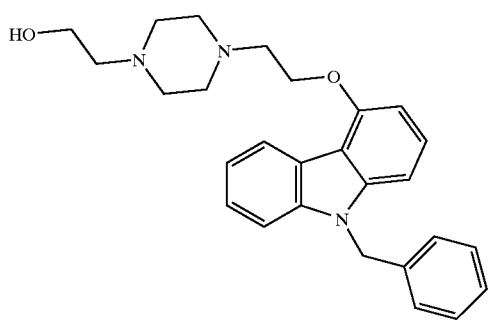

Example 10

3-({2-[(9-benzyl-9H-carbazol-4-yl)oxy]ethyl}amino)-1-propanol ms (m+H) at 375

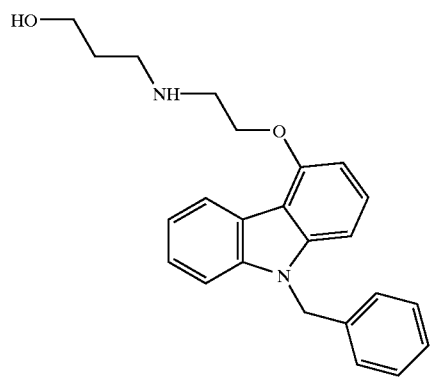

Example 11

N-{2-[(9-benzyl-9H-carbazol-4-yl)oxy]ethyl}-2-propen-1-amine ms (m+H) at 357

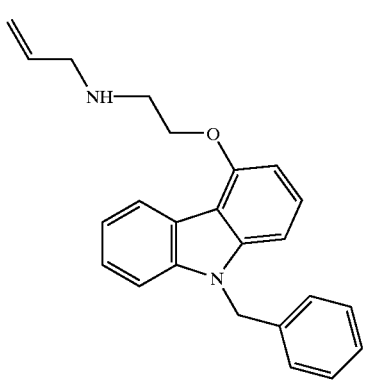

Example 12

N-{2-[(9-benzyl-9H-carbazol-4-yl)oxy]ethyl)}-3-(4-morpholinyl)-1-propanamine ms (m+H) at 444

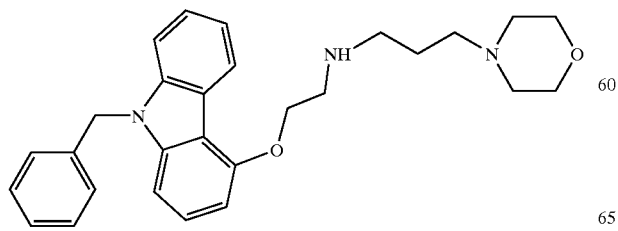

Example 13

5-({2-[(9-benzyl-9H-carbazol-4-yl)oxy]ethyl}amino)-1-pentanol ms (m+H) at 403

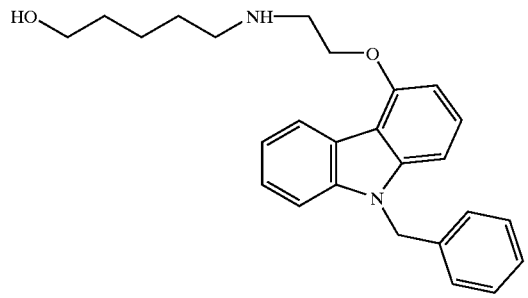

Example 14

N-{2-[(9-benzyl-9H-carbazol-4-yl)oxy]ethyl}-1-propanamine ms (m+H) at 359

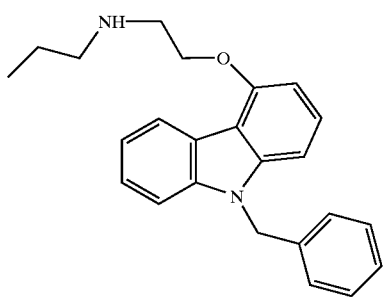

Example 15

N-{2-[(9-benzyl-9H-carbazol-4-yl)oxy]ethyl}-N-propyl-1-propanamine ms (m+H) at 401

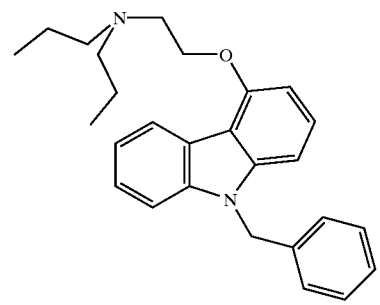

Example 16

1-benzyl-N-{2-[(9-benzyl-9H-carbazol-4-yl)oxy]ethyl}-4-piperidinamine ms (m+H) at 490

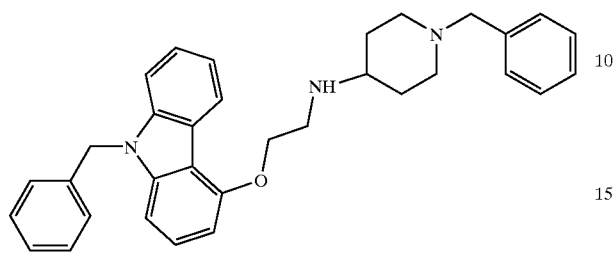

Example 17

2-({2-[(9-benzyl-9H-carbazol-4-yl)oxy]ethyl}amino)-2-methyl-1-propanol ms (m+H) at 389

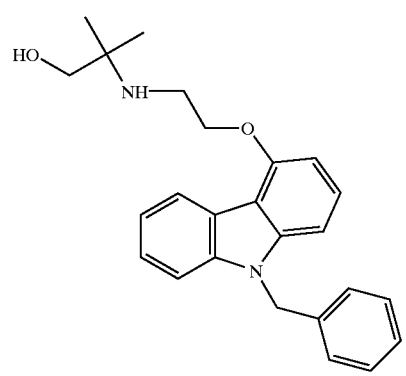

Example 18

2-[(9-benzyl-9H-carbazol-4-yl)oxy]-N-(4-chlorophenethyl)-1-ethanamine ms (m+H) at 455

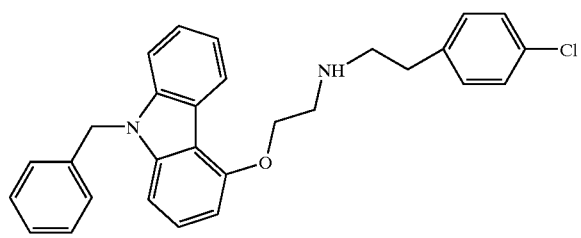

Example 19

2-[(9-benzyl-9H-carbazol-4-yl)oxy]-N-(cyclohexylmethyl)-1-ethanamine ms (m+H) at 413

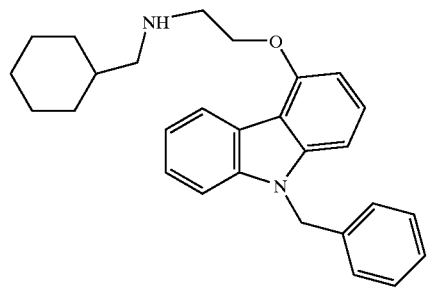

Example 20

2-[(9-benzyl-9H-carbazol-4-yl)oxy]-N-[2-(4-morpholinyl)ethyl]-1-ethanamine ms (m+H) at 430

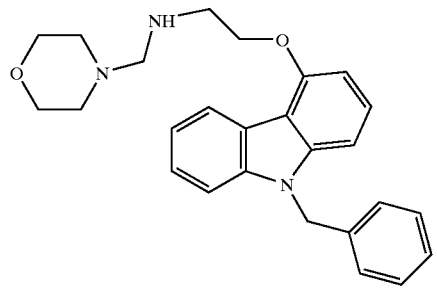

Example 21

1-({2-[(9-benzyl-9H-carbazol-4-yl)oxy]ethyl}amino)-2-butanol ms (m+H) at 389

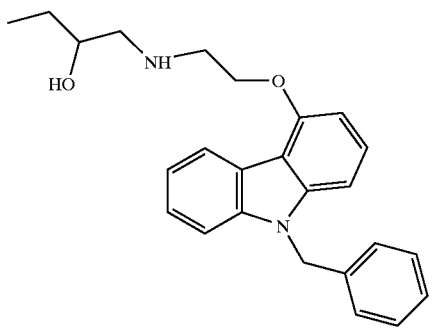

Example 22

2-[(9-benzyl-9H-carbazol-4-yl)oxy]-N-(4-fluorophenethyl)-1-ethanamine ms (m+H) at 439

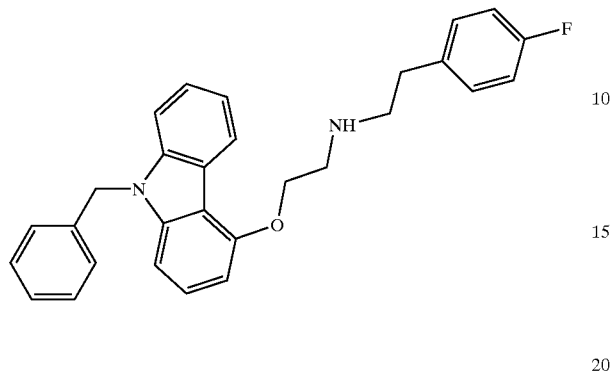

Example 23

2-[2-({2-[(9-benzyl-9H-carbazol-4-yl)oxy]ethyl}amino)ethoxy]-1-ethanol ms (m+H) at 405

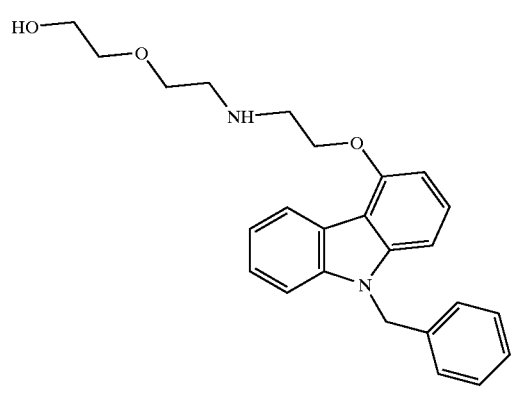

Example 24

(1S,2S)-2-({2-[(9-benzyl-9H-carbazol-4-yl)oxy]ethyl}amino)cyclohexanol ms (m+H) at 415

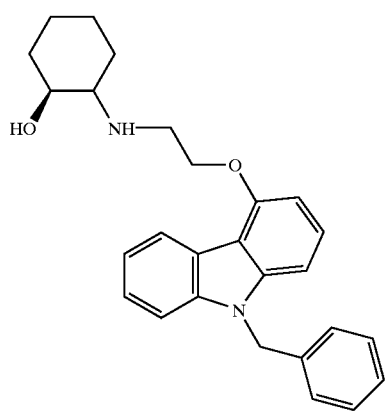

Example 25 ethyl 3-({2-[(9-benzyl-9H-carbazol-4-yl)oxy]ethyl}amino)propanoate ms (m+H) at 417

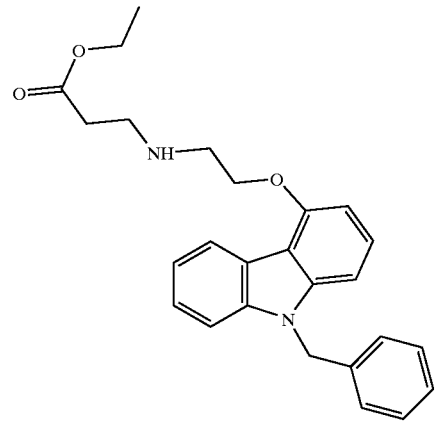

Example 26

N-{2-[(9-benzyl-9H-carbazol-4-yl)oxy]ethyl}cyclobutanamine ms (m+H) at 371

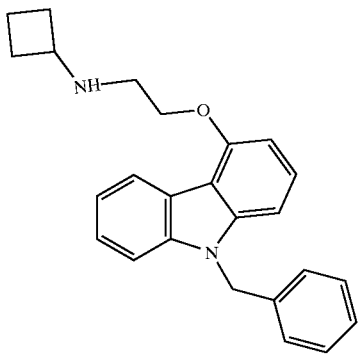

Example 27

2-(4-{2-[(9-benzyl-9H-carbazol-4-yl)oxy]ethyl}-1-piperazinyl)ethylformamide ms (m+H) at 457

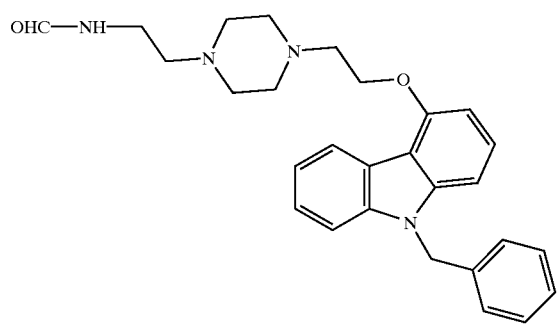

Example 28

N-(1H-benzimidazol-2-ylmethyl)-2-[(9-benzyl-9H-carbazol-4-yl)oxy]-1-ethanamine ms (m+H) at 447

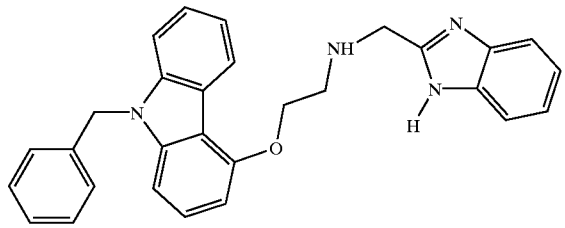

Example 29

1-{2-[(9-benzyl-9H-carbazol-4-yl)oxy]ethyl}-4-piperidinol ms (m+H) at 401

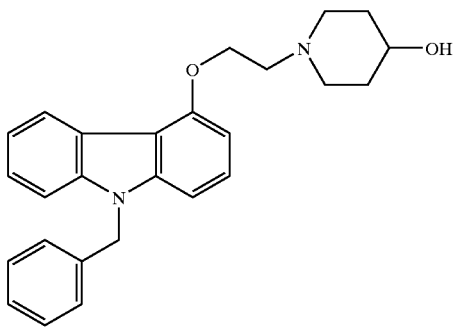

Example 30

9-benzyl-4-[2-(4-methyl-1-piperazinyl)ethoxy]-9H-carbazole ms (m+H) at 400

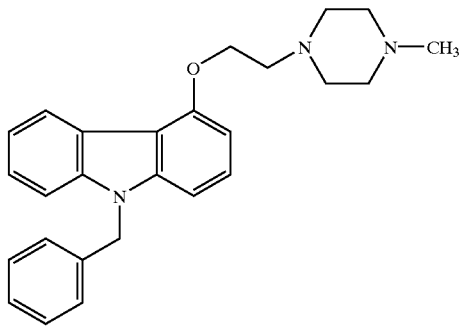

Example 31

N-{2-[(9-benzyl-9H-carbazol-4-yl)oxy]ethyl}-N-cyclopropylamine ms (m+H) at 357

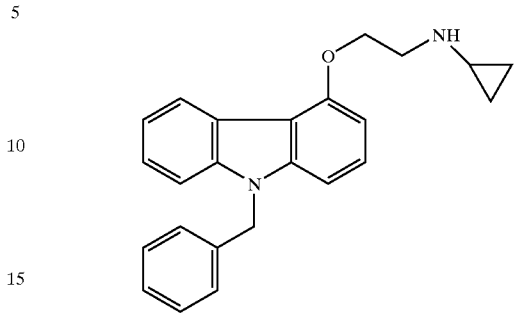

Example 32

N-{2-[(9-benzyl-9H-carbazol-4-yl)oxy]ethyl}-N,N-dimethylamine ms (m+H) at 345

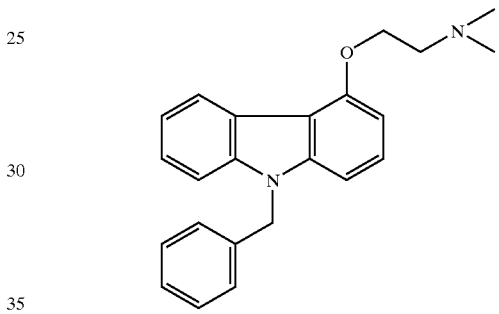

Example 33

N-{2-[(9-benzyl-9H-carbazol-4-yl)oxy]ethyl}formamide

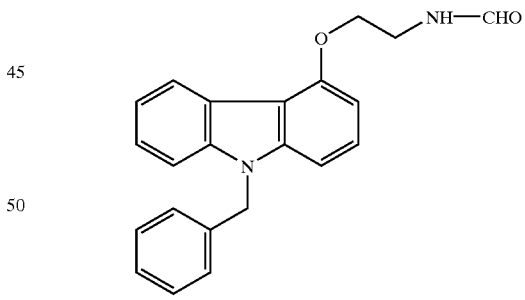

A mixture of 2-[(9-benzyl-9H-carbazol-4-yl)oxy]ethylamine (0.0714 g, 0.226 mmol) and ethyl formate (3 mL) is stirred at 65–70° C. for 45 min. After cooling, excess ethyl formate is removed in vacuo and the residue is partitioned between $CH_2Cl_2$ and aq. sodium sulfate. The organic layers are dried over sodium sulfate and concentrated; the residue is crystallized from $CH_2Cl_2$-EtOAc-hexane to give 0.0585 g (75%) of the title compound as a white, crystalline solid; mp 161–162° C.; MS (ESI+) for m/z 345 (M+H)$^+$, 367 (M+Na); $^1$H NMR (CDCl$_3$) δ3.95, 4.38, 5.52, 6.13, 6.68, 7.03, 7.10, 7.2–7.4, 8.27, 8.29; IR (drift) 3297, 1659, 1459, 1385, 1341, 1332, 1269, 1255, 1145, 1116, 780, 747, 737, 717, 700 cm$^{-1}$. Anal. Calcd for C$_{22}$H$_{20}$N$_2$O$_2$: C, 76.72; H, 5.85; N, 8.13. Found: C, 76.53; H, 5.99; N, 8.09.

Example 34

N-{2-[(9-Benzyl-9H-carbazol-4-yl)oxy]ethyl}-N-methylamine, maleic acid salt

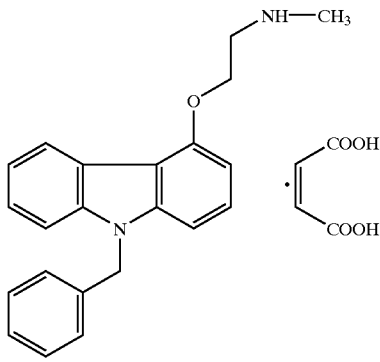

A mixture of 9-benzyl-4-(2-bromoethoxy)-9H-carbazole (0.165 g, 0.434 mmol) and methylamine (40% in H$_2$O; 0.4 mL) in acetonitrile (3 mL) is stirred in a glass pressure vessel with a screw top cap at 95° C. for 3.5 h, after which it is allowed to cool and stir at room temperature overnight. The solvent is then removed and the residue is chromatographed on silica gel using CH$_3$OH—CH$_2$Cl$_2$ (4/96 to 8/92) to give 0.125 g (87%) of product as the free base. The free base and maleic acid (0.0439 g) are dissolved in CH$_2$Cl$_2$ and CH$_3$OH, concentrated, and crystallized from CH$_2$Cl$_2$/hexane to give 0.119 g of the title compound; mp 182.5–184.5° C.; $^1$H NMR (free base) (CDCl$_3$) δ2.61, 3.21, 4.40, 5.51, 6.71, 6.99, 7.12, 7.2–7.4, 8.30. Anal. Calcd for C$_{22}$H$_{22}$N$_2$O.C$_4$H$_4$O$_4$: C, 69.94; H, 5.87; N, 6.27. Found: C, 69.7.1; H, 5.79; N, 6.21.

Example 35

2-[(9-Benzyl-9H-carbazol-4-yl)oxy]ethylamine

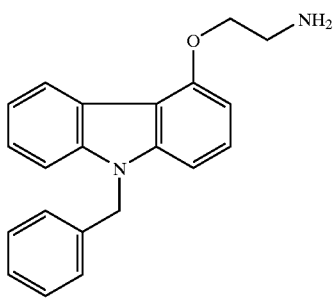

Sodium hydride (60% in oil; 0.934 g, 23.36 mmol) is washed three times with pentane. DMF (5 mL) is added, followed by 9-benzyl-9H-Carbazol-4-ol (1.52 g, 5.56 mmol) dissolved in DMF (10 mL) added over 10 min. The mixture is stirred an additional 5 min and then cooled in an ice-water bath. A solution of 2-chloroethylamine hydrochloride (1.29 g, 11.12 mmol) dissolved in DMF (5 mL) is added dropwise over about 5 min. The cooling bath is removed and the mixture is allowed to stir at room temperature over the weekend. Aq. sodium bicarbonate is added and the mixture partitioned between EtOAc, brine, and aq. sodium bicarbonate. The organic layers are dried over MgSO$_4$ and taken to dryness. The residue is chromatographed on silica gel (120 mL) using CH$_3$OH—CH$_2$Cl$_2$ (4/96) to give 1.26 g (72%) of the title compound as a white solid. An aliquot is crystallized from CH$_2$Cl$_2$-EtOAc-hexane; IR (drift) 1597, 1587, 1458, 1441, 1342, 1329, 1269, 1156, 1145, 1110, 1045, 860, 785, 749, 726 cm$^{-1}$; $^1$H NMR (CDCl$_3$) δ3.30, 4.29, 5.51, 6.70, 7.00, 7.12, 7.2–7.4, 8.34. Anal. Calcd for C$_{21}$H$_{20}$N$_2$O: C, 79.72; H, 6.37; N, 8.85. Found: C, 78.70; H, 6.41; N, 8.70.

Example 36

N-{2-[(9-Benzyl-9H-carbazol-4-yl)oxy]ethyl}-N-(2-methoxyethyl)amine

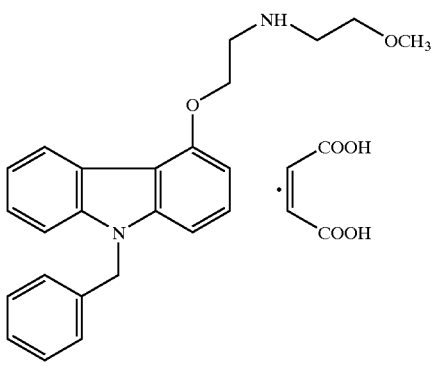

A mixture of 2-[(9-benzyl-9H-carbazol-4-yl)oxy] ethylamine (0.103 g, 0.327 mmol), 2-bromoethylmethyl ether (0.050 g, 0.359 mmol), diisopropylethylamine (0.0464 g, 0.359 mmol), acetonitrile (1 mL), and THF (1 mL) is stirred at room temperature for 40 min and then at 70° C. for 43 h. After cooling, the solvents are removed and the residue is chromatographed on silica gel (15 mL) using CH$_3$OH/ CH$_2$Cl$_2$ (4/96). The pure product fractions are concentrated to dryness to give 0.044 g (36%) of an oil. Maleic acid (0.013 g) is added and the salt is crystallized from CH$_2$Cl$_2$/ CH$_3$OH/hexane to give the title compound; mp 175.0–175.5° C.; $^1$H NMR (CDCl$_3$) δ2.98, 3.26, 3.39, 3.57, 4.38, 5.51, 6.70, 6.99, 7.12, 7.2–7.4, 8.33. Anal. Calcd for C$_{24}$H$_{26}$N$_2$O$_2$.C$_4$H$_4$O$_4$: C, 68.56; H, 6.16; N, 5.71. Found: C, 68.54; H, 6.22; N, 5.81.

Example 37

2-[(9-benzyl-9H-carbazol-4-yl)oxy]-N-ethyl-1-ethanamine, maleic acid salt

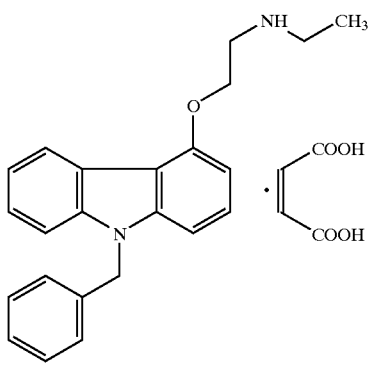

To a mixture of N-{2-[(9-benzyl-9H-carbazol-4-yl)oxy]ethyl}acetamide (0.3043 g, 0.849 mmol) and dry THF (7 ml) is added borane-methylsulfide complex (0.24 ml, 2.55 mmol) while under argon atmosphere. The mixture is refluxed at 85° C. for 18 h. Methanol is slowly added to consume unreacted borane complex. The mixture is stripped of solvent, then MeOH (5.0 ml) is added then stripped. The oil is dissolved in methanol/$CH_2Cl_2$ (10/1), to which is added concentrated hydrochloric acid (1.0 ml). The mixture is heated at 65° C. for 0.5 h. Water (5.0 ml) is added and the mixture neutralized with potassium carbonate, then partitioned between $CH_2Cl_2$ and water. The organic layer is washed with water and dried over magnesium sulfate. Column chromatography (50 g silica gel) using methanol/$CH_2Cl_2$ (5/95) gave an oil, which is converted to the maleic acid salt to give 0.1445 g (60%) of the title compound: $^1$H NMR (300 MHz, DMSO-d6) δ1.24, 3.16, 3.55, 4.47, 5.64, 5.99, 6.78, 7.09, 7.24, 7.37, 7.57, 8.30, 8.61. Anal. Calcd for $C_{23}H_{24}N_2O·C_4H_4O_4$: C, 70.42; H, 6.13; N, 6.08. Found: C, 70.27; H, 6.22; N, 6.03.

Example 38

9-Benzyl-4-[2-(1-pyrrolidinyl)ethoxy]-9H-carbazole

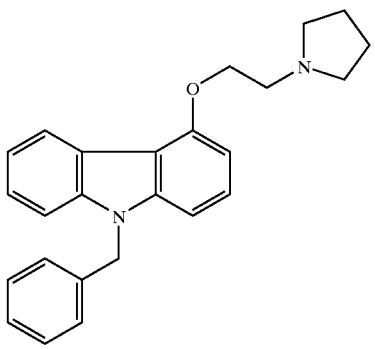

A mixture of 9-benzyl-4-(2-bromoethoxy)-9H-carbazole (0.020 g, 0.0526 mmol), pyrrolidine (0.040 g, 0.562 mmol), and acetonitrile (1.0 mL) is stirred over the weekend at room temperature; much starting material remained so the mixture is heated at 75° C. in a capped vial for 24 h. After cooling and removal of the solvent, the residue is partitioned between $CH_2Cl_2$ and aq. sodium bicarbonate. The organic layers are dried over sodium sulfate; chromatography on silica gel eluting with $CH_3OH$—$CH_2Cl_2$ (4/96) gave 0.0165 g (85%) of the title compound as a waxy solid; $^1$H NMR (CDCl$_3$) δ1.97, 3.04, 3.36, 4.59, 5.30, 6.71, 7.02, 7.12, 7.2–7.4, 8.32. Anal. Calcd for $C_{25}H_{26}N_2O$: C, 81.05; H, 7.07; N, 7.56. Found: C, 79.84; H, 7.02; N, 7.44.

Example 39

9-Benzyl-4-[2-(1-piperidinyl)ethoxy]-9H-carbazole

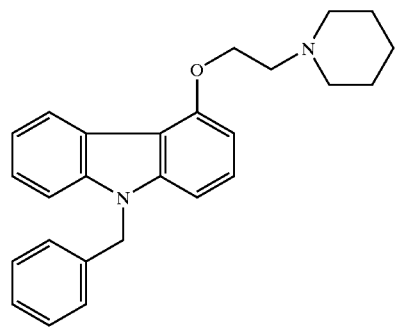

In the same manner as for 9-Benzyl-4-[2-(1-pyrrolidinyl)ethoxy]-9H-carbazole, 80 (0.020 g) and piperidine (0.040 g) gave 0.0196 g (97%) of the title compound; mp 113.5–114.5° C.; $^1$H NMR (CDCl$_3$) δ1.52, 1.73, 2.78, 3.14, 4.50, 5.51, 6.70, 7.00, 7.12, 7.2–7.4, 8.35. Anal. Calcd for $C_{26}H_{28}N_2O$: C, 81.21; H, 7.34; N, 7.28. Found: C, 80.59; H, 7.31; N, 7.22. CH CH Preparation 19 tert-Butyl 4-{2-[(9-Benzyl-9H-carbazol-4-yl)oxy]ethyl}-1-piperazinecarboxylate A mixture of 9-benzyl-4-(2-bromoethoxy)-9H-carbazole (0.0647 g, 0.170 mmol), Boc-piperazine (0.0380 g, 0.204 mmol), triethylamine (0.0206 g, 0.204 mmol), and acetonitrile (2 mL) is heated at reflux for 24 h. After cooling, the mixture is partitioned between $CH_2Cl_2$ and aq. sodium bicarbonate. The organic layers are dried over sodium sulfate; chromatography on silica gel eluting with $CH_3OH$—$CH_2Cl_2$ (2/98) gave poor separation of product and impurities. Re-chromatography (silica gel, 20 mL) using acetone-hexane (10/90 to 20/80) gave 0.0650 g (83%) of the title compound; IR (drift) 1693, 1457, 1420, 1365, 1341, 1332, 1291, 1266, 1243, 1174, 1154, 1145, 1129, 1112, 752 cm$^{-1}$; $^1$H NMR (CDCl$_3$) δ1.46, 2.65, 3.06, 3.48, 4.41, 5.51, 6.69, 6.99, 7.12, 7.2–7.4, 8.37. Anal. Calcd for $C_{30}H_{35}N_3O_3$: C, 74.20; H, 7.26; N, 8.65. Found: C, 73.82; H, 7.41; N, 8.52.

Example 40

9-Benzyl-4-[2-(1-piperazinyl)ethoxy]-9H-carbazole

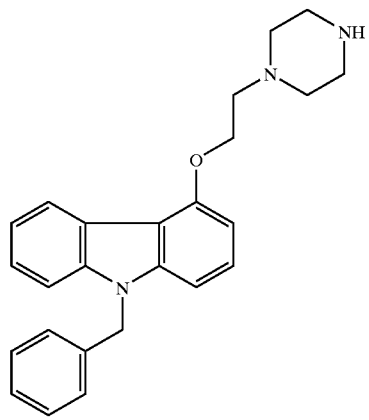

A mixture of tert-Butyl 4-{2-[(9-Benzyl-9H-carbazol-4-yl)oxy]ethyl}-1-piperazinecarboxylate (0.0450 g, 0.0927 mmol), trifluoroacetic acid (2.5 mL), and CH$_2$Cl$_2$ (2.5 mL) is stirred at room temperature for 1 h. Trifluoroacetic acid and CH$_2$Cl$_2$ are then removed in vacuo and the residue is partitioned between CH$_2$Cl$_2$ and aq. sodium bicarbonate. The organic layers are dried over sodium sulfate and taken to dryness to give 0.0326 g (91%) of the title compound; IR (drift) 2935, 2821, 1584, 1456, 1353, 1342, 1332, 1271, 1245, 1154, 1145, 1112, 783, 750, 715 cm$^{-1}$; $^1$H NMR (CDCl$_3$) δ2.70, 2.95, 3.04, 4.41, 5.50, 6.69, 6.99, 7.12, 7.2–7.4, 8.39. Anal. Calcd for C$_{25}$H$_{27}$N$_3$O: C, 77.89; H, 7.06; N, 10.90. Found: C, 76.35; H, 7.20; N, 10.30.

Example 41

2-[(9-Benzyl-8-fluoro-9H-carbazol-4-yl)oxy]ethylamine

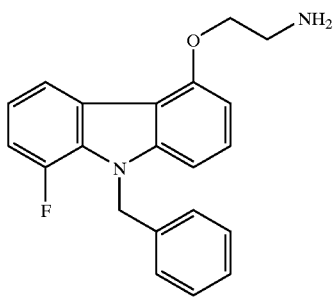

A mixture of 2-[(9-benzyl-8-fluoro-9H-carbazol-4-yl)oxy]acetonitrile (0.7685 g, 0.0023 mol), dry THF (20 mL) and borane-methyl sulfide (0.71 mL, 0.0075 mol) is stirred at room temperature for 3.5 h. Additional borane-methyl sulfide (0.20 mL, 0.0021 mol) is added and the mixture is stirred overnight. The excess borane is cautiously quenched with methanol and the mixture is concentrated under reduced pressure. Methanol and dichloromethane are added to the residue and the solution is again concentrated under reduced pressure (repeated twice). The solids are then dissolved in methanol/dichloromethane and conc. HCl (3 mL) is added. After the mixture stirred for 50 min, the solvent is removed under reduced pressure and the residue is partitioned between dichloromethane and aq. sodium bicarbonate. The combined organic layers are dried over sodium sulfate and concentrated to dryness. The residue is chromatographed on silica gel (100 mL) using methanol/dichloromethane (2/98 and 4/96) and recrystallized from ethyl acetate/dichloromethane/heptane to give 0.333 g (43%) of the title compound; mp 122.25–123° C.; MS (ESI+) for C$_{21}$H$_{19}$FN$_2$O m/z 335.2 (M+H)$^+$; IR (drift) 1602, 1577, 1498, 1456, 1443, 1352, 1337, 1325, 1269, 1254, 1242, 1228, 1141, 792, 736 cm$^{-1}$; $^1$H NMR (CDCl$_3$) δ3.30, 4.28, 5.30, 6.70, 7.01, 7.11, 7.22, 7.36, 8.10, NH$_2$ not seen. Anal. Calcd for C$_{21}$H$_{19}$FN$_2$O: C, 75.43; H, 5.73; N, 8.38. Found: C, 75.25; H, 5.79; N, 8.28.

Preparation 20 8-Fluoro-9-(4-fluorobenzyl)-1,2,3,9-tetrahydro-4H-carbazol-4-one 8-Fluoro-1,2,3,9-tetrahydro-4H-carbazol-4-one (0.1416 g, 0.70 mmol) is added to a slurry of pentane-washed NaH (0.0400 g, 0.0010 mol) in DMF (2 mL) and after stirring for 30 min, p-fluorobenzyl bromide (0.11 mL, 0.88 mmol) is added. After the mixture had stirred for 2.3 h, it is partitioned between aq. sodium bicarbonate and ethyl acetate. The organic layer is dried over sodium sulfate and concentrated to dryness. The resulting solids are chromatographed on silica gel (100 mL) using first dichloromethane (100%) and then methanol/dichloromethane (2/98). The product fractions are combined and rechromatographed on silica gel (50 mL) using acetone/heptane/NH$_4$OH (15/85/0.25) and then recrystallized using ethyl acetate/hexane to give 0.0932 g (43%) of the title compound; mp 177–178° C.; MS (ESI−) for C$_{19}$H$_{15}$F$_2$NO m/z 310.1 (M−H)$^−$; IR (drift) 1638, 1630, 1509, 1496, 1459, 1436, 1413, 1361, 1249, 1222, 1194, 1158, 1125, 830, 790 cm$^{-1}$; $^1$H NMR (CDCl$_3$) δ2.24, 2.58, 2.86, 5.47, 6.89–7.02, 7.16, 8.06. Anal. Calcd for C$_{19}$H$_{15}$F$_2$NO: C, 73.30; H, 4.86; N, 4.50. Found: C, 73.40; H, 4.83; N, 4.50.

Preparation 21 8-Fluoro-9-(4-fluorobenzyl)-9H-carbazol-4-ol

Pyridinium bromide perbromide (0.0.860 g, 0.27 mmol) is added to a solution of 8-fluoro-9-(4-fluorobenzyl)-1,2,3,9-tetrahydro-4H-carbazol-4-one in THF (0.5 mL) and DMF (0.5 mL) and the mixture is heated to 75° C. After stirring for 4.5 h, THF is removed under reduced pressure and the residue is partitioned between ethyl acetate and dilute brine. The combined organic layers are washed with dilute sodium sulfate/brine and the aqueous layer is backwashed with ethyl acetate. The combined organic layers are dried over magnesium sulfate and concentrated under reduced pressure to give a residue. A mixture of the resulting residue, lithium bromide (0.0428 g, 0.49 mmol), lithium carbonate (0.0311 g, 0.42 mmol) and DMF (1 mL) is heated at 120° C. for two hours. The mixture is partitioned between ethyl acetate and brine. The combined organic layers are dried over sodium sulfate and concentrated to an oil. The oil is chromatographed on silica gel (20 mL) using ethyl acetate/heptane (5/95 and 10/90) to give 0.0460 g (71%) of the title compound; MS (ESI−) for C$_{19}$H$_{13}$F$_2$NO m/z 308.1 (M−H)$^−$; IR (drift) 1580, 1508, 1461, 1434, 1329, 1274, 1242, 1235, 1221, 1157, 1129, 907, 788, 755, 732 cm$^{-1}$; $^1$H NMR (CDCl$_3$) δ5.37 5.64, 6.60, 6.94, 7.14, 7.28, 8.10. Anal. Calcd for C$_{19}$H$_{13}$F$_2$NO: C, 73.78; H, 4.24; N, 4.53. Found: C, 72.52; H, 4.18; N, 4.37.

Example 42

N,N-Diethyl-N-(2-{[8-fluoro-9-(4-fluorobenzyl)-9H-carbazol-4-yl]oxy}ethyl)amine

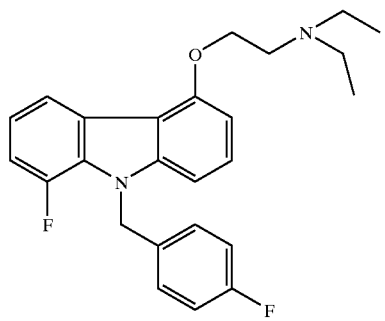

8-Fluoro-9-(4-fluorobenzyl)-9H-carbazol-4-ol (0.0226 g, 0.073 mmol), 2-diethylaminoethylchloride hydrochloride (0.0202 g, 0.12 mmol), potassium carbonate (0.0330 g, 0.24 mmol), sodium iodide (0.0018 g, 0.012 mmol) and DMF (1 mL) are heated at 80° C. for 3 h. After the mixture had cooled, it is partitioned between water and ethyl acetate. The organic layer is dried over magnesium sulfate and concentrated to an oil. The oil is chromatographed on silica gel (20 mL) using methanol/dichloromethane (2/98 and 4/96) to give 0.0222 g (74%) of the title compound; mp 59–60° C.; MS (ESI+) for $C_{25}H_{27}F_2N_2O$ m/z 409.3 (M+H)$^+$; $^1$H NMR (CDCl$_3$) δ1.21, 2.87, 3.22, 4.45, 5.67, 6.74, 6.94, 7.02, 7.14, 7.39, 8.11. Anal. Calcd for $C_{25}H_{26}F_2N_2O$: C, 73.51; H, 6.41; N, 6.86. Found: C, 73.05; H, 6.61; N, 6.83.

Preparation 22 6-Chloro-1,2,3,9-tetrahydro-4H-carbazol-4-one

4-Chlorophenylhydrazine hydrochloride (5.3766 g, 0.0300 mol) is added portion-wise to a solution of 1,3-cyclohexanedione (3.29 g, 0.029 mol) in water (58 mL) and the mixture is allowed to stir over night at room temperature. The resulting solids are collected by filtration, washed with water, and vacuum dried at 50° C. overnight to give the hydrazone. The hydrazone (0.5249 g, 0.0022 mol) is then heated at reflux in trifluoroacetic acid (3 mL) for 7 h, at which time the heat is turned off and the mixture is allowed to stir overnight at room temperature. Additional trifluoroacetic acid (1 mL) then is added and the mixture is stirred at reflux another 7 h and stored in the refrigerator overnight. The mixture is partitioned between water and dichloromethane. The organic layer is washed with aq.sodium bicarbonate and the aqueous layer is backwashed with dichloromethane. The combined organic layers are then dried over magnesium sulfate and concentrated to solids. The solids are chromatographed on silica gel (100 mL) using ethyl acetate/dichloromethane and then recrystallized from ethyl acetate/dichloromethane/methanol to give 0.0872 g (15%) of the title compound; MS (ESI–) for $C_{12}H_{10}CLNO$ m/z 218.0 (M–H)$^−$; IR (drift) 3201, 3172, 3137, 3109, 3063, 2954, 2933, 1631, 1578, 1472, 1373, 1013, 879, 811, 623 cm$^{-1}$; $^1$H NMR (CD$_3$OD) δ2.22, 2.54, 3.00, 7.16, 7.32, 7.97, NH not seen. Anal. Calcd for $C_{12}H_{10}ClNO$: C, 65.61; H, 4.59; N, 6.38. Found: C, 65.49; H, 4.51; N, 6.32.

Preparation 23 9-Benzyl-6-chloro-1,2,3,9-tetrahydro-4H-carbazol-4-one

6-Chloro-1,2,3,9-tetrahydro-4H-carbazol-4-one (0.4010 g, 0.0018 mol) is added to a slurry of pentane-washed NaH (0.0902 g, 0.0023 mol) in DMF (2 mL) and after stirring for 27 min, benzyl bromide (0.26 mL, 0.0022 mol) is added. After stirring for 2.5 h at room temperature, the mixture is partitioned between aq. sodium bicarbonate and ethyl acetate. The combined organic layers are dried over sodium sulfate and concentrated to dryness. The resulting solids are chromatographed on silica gel (200 mL) using dichloromethane/heptane (60/40 and 100/0) to give 0.5158 g (91%) of the title compound. An aliquot (0.0625 g) is recrystallized from ethyl acetate/heptane to give 0.0415 g of product; mp 196.5–197° C.; MS (ESI+) for $C_{19}H_{16}ClNO$ m/z 310.1 (M+H)$^+$; $^1$H NMR (CDCl$_3$) δ2.24, 2.58, 2.87, 5.31, 6.99, 7.16, 7.29, 8.28. Anal. Calcd for $C_{19}H_{16}ClNO$: C, 73.66; H, 5.20; N, 4.52. Found: C, 73.18; H, 5.19; N, 4.58.

Preparation 24 9-Benzyl-6-chloro-9H-carbazol-4-ol

Pyridinium bromide perbromide (0.5495 g, 0.0017 mol) is added to a solution of 9-benzyl-6-chloro-1,2,3,9-tetrahydro-4H-carbazol-4-one (0.4406 g, 0.0014 mol) in THF (2.8 mL) and DMF (1.5 mL) and the mixture is heated to 75° C. After stirring for 5 h, THF is removed under reduced pressure and the residue is partitioned between dichloromethane and brine. The combined organic layers are washed with dilute sodium thiosulfate/brine and the aqueous layer is back-washed with dichloromethane. The combined organic layers are dried over magnesium sulfate and concentrated under reduced pressure to give a residue. A mixture of the resulting residue, lithium bromide (0.2799 g, 0.0032 mol), lithium carbonate (0.2286 g, 0.0031 mol) and DMF (6 mL) is heated at 120° C. for two hours. The DMF is removed under high vacuum and the residue is partitioned between dichloromethane and water. The combined organic layers are dried over sodium sulfate and concentrated to an oil. The oil is chromatographed on silica gel (100 mL) using dichloromethane (100%) to give 0.3139 g (72%) of the title compound. An aliquot (0.0391) is recrystallized from dichloromethane/methanol/hexane to give 0.0272 g of product; MS (ESI–) for $C_{19}H_{14}ClNO$ m/z 306.0 (M–H)$^−$; IR (drift) 1470, 1452, 1334, 1293, 1284, 1266, 1231, 1146, 1112, 885, 796, 777, 746, 717, 702 cm$^{-1}$; $^1$H NMR (CDCl$_3$) δ5.41, 5.49, 6.60, 6.97, 7.13, 7.28, 7.35, 8.33. Anal. Calcd for $C_{19}H_{14}ClNO$: C, 74.15; H, 4.59; N, 4.55; Cl, 11.52. Found: C, 73.07; H, 4.63; N, 4.59.

Example 43

N-{2-[(9-Benzyl-6-chloro-9H-carbazol-4-yl)oxy]ethyl}-N,N-diethylamine

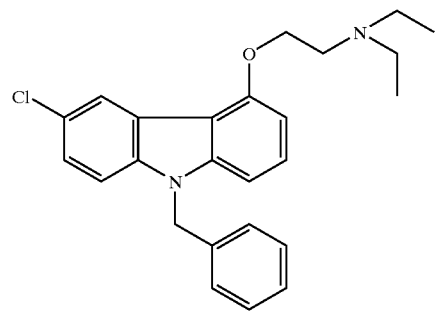

9-Benzyl-6-chloro-9H-carbazol-4-ol (0.0616 g, 0.20 mmol), 2-diethylaminoethylchloride hydrochloride (0.0517 g, 0.30 mmol), potassium carbonate (0.0863 g, 0.62 mmol), sodium iodide (0.0027 g, 0.018 mmol) and DMF (1 mL) are heated at 85° C. for 3.5 h. After the mixture had cooled, it is partitioned between water and ether. The combined organic layers are dried over magnesium sulfate and concentrated to an oil. The oil is chromatographed on silica gel (60 mL) using methanol/dichloromethane (1/99 to 2/98 to 4/96) to give 0.0665 g (82%) of the title compound; mp 96–97.5° C.; MS (ESI+) for $C_{25}H_{27}ClN_2O$ m/z 407.3 (M+H)$^+$; IR (drift) 2966, 1583, 1466, 1453, 1340, 1268, 1242, 1149, 1124, 1069, 795, 780, 745, 718, 708 cm$^{-1}$; $^1$H NMR (CDCl$_3$) δ1.16, 2.75, 3.12, 4.34, 5.47, 6.69, 6.97, 7.08, 7.21–7.38, 8.34. Anal. Calcd for $C_{25}H_{27}ClN_2O$: C, 73.79; H, 6.69; N, 6.88. Found: C, 73.39; H, 6.73; N, 6.78.

Preparation 25 6-Chloro-9-(4-fluorobenzyl)-1,2,3,9-tetrahydro-4H-carbazol-4-one

6-Chloro-1,2,3,9-tetrahydro-4H-carbazol-4-one (0.4042 g, 0.0018 mol) is added to a slurry of pentane-washed NaH (0.091 g, 0.0023 mol) in DMF (2 mL) and after stirring for 20 min, p-fluorobenzyl bromide (0.28 mL, 0.0023 mol) is added. Additional DMF (1 mL) is added and the mixture is stirred for 4 h, at which time the mixture is partitioned between aq. sodium bicarbonate and ethyl acetate. The combined organic layers are washed with water, dried over sodium sulfate and concentrated to dryness. The resulting solids are chromatographed on silica gel (200 mL) using dichloromethane/heptane (60/40 and 80/20) to give 0.5519 g (92%) of the title compound; mp 207–207.75° C.; MS (ESI+) for $C_{19}H_{15}ClFNO$ m/z 328.1 (M+H)$^+$; IR (drift) 1628, 1511, 1467, 1448, 1360, 1226, 1218, 1145, 1096, 878, 849, 840, 804, 764, 649 cm$^{-1}$; $^1$H NMR (CDCl$_3$) δ2.23, 2.58, 2.86, 5.27, 6.99, 7.16, 8.27. Anal. Calcd for $C_{19}H_{15}ClFNO$: C, 69.62; H, 4.61; N, 4.27. Found (av): C, 69.08; H, 4.50; N, 4.26.

Preparation 26 6-Chloro-9-(4-fluorobenzyl)-9H-carbazol-4-ol

Pyridinium bromide perbromide (0.6155 g, 0.0019 mol) is added to a solution of 6-chloro-9-(4-fluorobenzyl)-1,2,3,9-tetrahydro-4H-carbazol-4-one in THF (2.2 mL) and DMF (1.5 mL) and the mixture is heated to 75° C. After stirring for 3.5 h, the THF is removed under reduced pressure and the residue is partitioned between dichloromethane and brine. The combined organic layers are washed with dilute sodium thiosulfate/brine and the aqueous layer is back-washed with dichloromethane. The combined organic layers are dried over magnesium sulfate and concentrated under reduced pressure to give a residue. A mixture of the resulting residue, lithium bromide (0.3077 g, 0.0036 mol), lithium carbonate (0.2376 g, 0.0032 mol) and DMF (6 mL) is heated at 120° C. for two hours. The DMF is removed under high vacuum and the residue is partitioned between dichloromethane and water. The combined organic layers are dried over sodium sulfate and concentrated to dryness. The residue is chromatographed on silica gel (125 mL) using dichloromethane (100%) to give 0.3773 g (73%) of the title compound. An aliquot is recrystallized from dichloromethane/hexane; MS (ESI–) for $C_{19}H_{13}ClFNO$ m/z 324.1 (M–H)$^-$; IR (drift) 1510, 1468, 1444, 1335, 1297, 1263, 1232, 1218, 1147, 1116, 832, 822, 791, 778, 745 cm$^{-1}$; $^1$H NMR (CDCl$_3$) δ5.37, 5.43, 6.59, 6.94, 7.07, 7.23, 7.33, 8.31. Anal. Calcd for $C_{19}H_{13}ClFNO$: C, 70.05; H, 4.02; N, 4.30; Cl, 10.88. Found: C, 68.51; H, 3.96; N, 4.27.

Preparation 27 N-(2-{[6-Chloro-9-(4-fluorobenzyl)-9H-carbazol-4-yl]oxy}ethyl)-N,N-diethylamine 6-Chloro-9-(4-fluorobenzyl)-9H-carbazol-4-ol (0.0619 g, 0.19 mmol), 2-diethylaminoethylchloride hydrochloride (0.0494 g, 0.29 mmol), potassium carbonate (0.0750 g, 0.54 mmol), sodium iodide (0.0021 g, 0.014 mmol) and DMF (1 mL) are heated at 85° C. for 4 h. After the mixture had cooled, it is partitioned between water and ether. The aqueous layer is also extracted with ethyl acetate several times. The combined organic layers are dried over magnesium sulfate and concentrated to an oil. The oil is chromatographed on silica gel (75 mL) using methanol/dichloromethane (1/99 to 2/98 to 4/96) to give 0.0591 g (73%) of the title compound; mp 99–99.5° C.; MS (ESI+) for $C_{25}H_{26}ClFN_2O$ m/z 425.2 (M+H)$^+$; IR (drift) 2972, 1588, 1507, 1467, 1454, 1342, 1270, 1221, 1151, 1123, 817, 799, 778, 740, 714 cm$^{-1}$; $^1$H NMR (CDCl$_3$) δ1.15, 2.75, 3.12, 4.33, 5.44, 6.71, 6.93, 7.04, 7.20, 7.34, 8.33. Anal. Calcd for $C_{25}H_{26}ClFN_2O$: C, 70.66; H, 6.17; N, 6.59. Found: C, 70.23; H, 6.05; N, 6.61.

Preparation 28 6-Fluoro-1,2,3,9-tetrahydro-4H-carbazol-4-one

4-Fluorophenylhydrazine hydrochloride (4.5697 g, 0.0281 mol) is added in portions to a solution of 1,3-cyclohexanedione (3.11 g, 0.0277 mol) in water (55 mL). The mixture is allowed to shake overnight at room temperature. Additional 4-fluorophenylhydrazine hydrochloride (0.1052 g, 0.65 mmol) is added and the mixture is shaken another 6 h. After sitting at room temperature overnight the mixture is extracted with ethyl acetate. The organic layer is washed with water and the aqueous layer is backwashed with ethyl acetate. The combined organic layers are dried over sodium sulfate and concentrated to give the hydrazone. The hydrazone and trifluoroacetic acid (37 mL) are heated at 85° C. for 3.5 h. After cooling, the mixture is partitioned between water and dichloromethane. The combined organic layers are washed with aq. sodium bicarbonate and the aqueous layer is washed with dichloromethane. The combined organic layers are dried over magnesium sulfate and concentrated to a foam. The foam is chromatographed on silica gel (200 mL) using ethyl acetate/dichloromethane (5/95 to 10/90 to 20/80) and recrystallized from ethyl acetate/methanol/hexane to give 0.6197 g (11%) for a first crop and 0.3281 g (6%) for a second crop of the title compound; MS (ESI–) for $C_{12}H_{10}FNO$ m/z 202.0 (M–H)$^-$; IR (drift) 3231, 3183, 2942, 1708, 1623, 1482, 1468, 1377, 1203, 1173, 1131, 914, 856, 804, 793 cm$^{-1}$; $^1$H NMR (CD$_3$OD) δ2.22, 2.54, 3.00, 6.95, 7.32, 7.66, NH not seen. Anal. Calcd for $C_{12}H_{10}FNO$: C, 70.93; H, 4.96; N, 6.89. Found: C, 70.76; H, 5.05; N, 6.85.

Preparation 29 9-Benzyl-6-fluoro-1,2,3,9-tetrahydro-4H-carbazol-4-one

6-Fluoro-1,2,3,9-tetrahydro-4H-carbazol-4-one (0.3938 g, 0.0019 mol) is added to a slurry of pentane-washed NaH (0.0970 g, 0.0024 mol) in DMF (3 mL) and after stirring for 10 min, benzyl bromide (0.28 mL, 0.0024 mol) is added. After stirring for 4 h at room temperature, the mixture is partitioned between water and ethyl acetate. The combined organic layers are dried over sodium sulfate and concentrated to dryness. The resulting solids are chromatographed on silica gel (200 mL) using dichloromethane/heptane (60/40 to 80/20 to 100/0) to give 0.3681 g (65%) of the title compound. An aliquot is recrystallized from ethyl acetate/heptane; MS (ESI+) for $C_{19}H_{16}FNO$ m/z 294.2 (M+H)$^+$; IR (drift) 1634, 1523, 1483, 1466, 1447, 1357, 1254, 1138, 900, 868, 803, 799, 759, 729, 700 cm$^{-1}$; $^1$H NMR (CDCl3) δ2.22, 2.59, 2.88, 5.32, 6.95, 7.01, 7.15, 7.30, 7.96. Anal. Calcd for $C_{19}H_{16}FNO$: C, 77.80; H, 5.50; N, 4.78. Found: C, 77.65; H, 5.39; N, 4.69.

Preparation 30 9-Benzyl-6-fluoro-9H-carbazol-4-ol

Pyridinium bromide perbromide (0.4620 g, 0.0014 mol) is added to a mixture of 9-benzyl-6-fluoro-1,2,3,9-tetrahydro-4H-carbazol-4-one (0.3271 g, 0.0011 mol) in THF (3.4 mL) and DMF (2.4 mL) and the mixture is heated to 75° C. After stirring for 6.5 h, the mixture is stored in the freezer overnight. Heating is resumed for an additional 2.5 h, at which time THF is removed under reduced pressure and the residue is partitioned between dichloromethane and brine. The combined organic layers are washed with dilute sodium thiosulfate/brine and the aqueous layer is backwashed with dichloromethane. The combined organic layers are dried over sodium sulfate and concentrated under reduced pressure to give a residue. The residue is heated to 120° C. in DMF (5 mL) with lithium bromide (0.2348 g, 0.0027 mol) and lithium carbonate (0.1813 g, 0.0025 mol). After 2 h, DMF is removed under high vacuum and the mixture is partitioned between dichloromethane and water. The combined organic layers are washed with water and the aqueous layer is backwashed with dichloromethane. The combined organic layers are dried over sodium sulfate and concentrated to an oil. The oil is chromatographed on silica gel (100 mL) using dichloromethane/hexane (30/70 and 50/50) to give 0.1893 g (58%) of the title compound. An aliquot is precipitated from hexane/ ether; MS (ESI+) for $C_{19}H_{14}FNO$ m/z 292.2 (M+H)+; IR (drift) 1483, 1466, 1451, 1337, 1304, 1174, 1157, 1138, 884, 859, 794, 777, 745, 713, 700 cm$^{-1}$; $^1$H NMR (CDCl3) δ5.34, 5.47, 6.56, 6.95, 7.13, 7.20–7.30, 8.01. Anal. Calcd for $C_{19}H_{14}FNO$: C, 78.33; H, 4.84; N, 4.81. Found: C, 78.17; H, 4.83; N, 4.78.

Example 44

N-{2-[(9-Benzyl-6-fluoro-9H-carbazol-4-yl)oxy]ethyl}-N,N-diethylamine

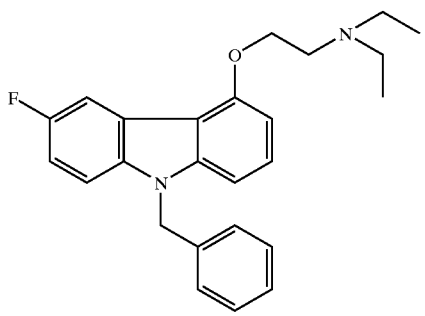

9-Benzyl-6-fluoro-9H-carbazol-4-ol (0.0587 g, 0.20 mmol), 2-diethylaminoethylchloride hydrochloride (0.0524 g, 0.30 mmol), potassium carbonate (0.0872 g, 0.63 mmol), sodium iodide (0.0062 g, 0.041 mmol) and DMF (2 mL) are heated at 85° C. for 3 h. After the mixture had cooled, it is partitioned between water and ethyl acetate. The combined organic layers are dried over magnesium sulfate and concentrated to an oil. The oil is chromatographed on silica gel (50 mL) using methanol/dichloromethane (1/99 to 3/97) to give 0.0485 g (62%) of the title compound; mp 68–69° C.; MS (ESI+) for $C_{25}H_{27}FN_2O$ m/z 391.3 (M+H)+; IR (drift) 2966, 1584, 1483, 1463, 1345, 1268, 1185, 1162, 1145, 1052, 799, 778, 741, 726, 713 cm$^{-1}$; $^1$H NMR (CDCl$_3$) δ1.14, 2.73, 3.10, 4.33, 5.48, 6.68, 6.97, 7.11, 7.21, 7.35, 8.03. Anal. Calcd for $C_{25}H_{27}FN_2O$: C, 76.89; H, 6.97; N, 7.17. Found: C, 77.16; H, 7.28; N, 7.16.

Preparation 31 6-Fluoro-9-(4-fluorobenzyl)-1,2,3,9-tetrahydro-4H-carbazol-4-one

6-Fluoro-1,2,3,9-tetrahydro-4H-carbazol-4-one (0.3940 g, 0.0019 mol) is added to a slurry of pentane-washed NaH (0.0966 g, 0.0024 mol) in DMF (3 mL) and after stirring for 10 min, p-fluorobenzyl bromide (0.29 mL, 0.0023 mol) is added. After stirring for 4 h at room temperature, the mixture is partitioned between water and ethyl acetate. The combined organic layers are dried over sodium sulfate and concentrated to dryness. The resulting solids are chromatographed on silica gel (100 mL) using methanol/dichloromethane (0.5/99.5) to give 0.5678 g (94%) of the title compound. An aliquot is recrystallized from ethyl acetate/heptane; mp 182.5–183° C.; MS (ESI+) for $C_{19}H_{15}F_2NO$ m/z 312.2 (M+H)+; IR (drift) 1631, 1511, 1483, 1466, 1449, 1256, 1228, 1218, 1137, 1094, 867, 836, 813, 808, 802 cm$^{-1}$; $^1$H NMR (CDCl$_3$) δ2.24, 2.58, 2.86, 5.28, 6.94, 7.13, 7.96. Anal. Calcd for $C_{19}H_{15}F_2NO$: C, 73.30; H, 4.86; N, 4.50. Found: C, 73.27; H, 4.92; N, 4.54.

Preparation 32 6-Fluoro-9-(4-fluorobenzyl)-9H-carbazol-4-ol

Pyridinium bromide perbromide (0.7068 g, 0.0022 mol) is added to a mixture of 6-fluoro-9-(4-fluorobenzyl)-1,2,3,9-tetrahydro-4H-carbazol-4-one (0.5245 g, 0.0017 mol) in THF (4 mL) and DMF (4 mL) and the mixture is heated to 75° C. After stirring for 6.5 h, the mixture is stored in the freezer overnight. Heating is resumed for an additional 2.5 h, at which time THF is removed under reduced pressure and the residue is partitioned between dichloromethane and brine. The combined organic layers are washed with dilute sodium thiosulfate/brine and the aqueous layer is back-washed with dichloromethane. The combined organic layers are dried over sodium sulfate and concentrated under reduced pressure to give a residue. The residue is heated to 120° C. in DMF (8 mL) with lithium bromide (0.3412 g, 0.0039 mol) and lithium carbonate (0.2548 g, 0.0035 mol). After 2 h, DMF is removed under high vacuum and the mixture is partitioned between dichloromethane and water. The combined organic layers are washed with water, dried over sodium sulfate and concentrated to an oil. The oil is chromatographed on silica gel (100 mL) using dichloromethane/hexane (30/70 to 50/50) to give 0.2706 g (52%) of the title compound; MS (ESI–) for $C_{19}H_{13}F_2NO$ m/z 308.0 (M–H)–; IR (drift) 1511, 1483, 1465, 1450, 1336, 1222, 1215, 1172, 1157, 1138, 883, 858, 791, 777, 744 cm$^{-1}$; $^1$H NMR (CDCl$_3$) δ5.35, 5.44, 6.57, 6.95, 7.06–7.30, 8.01. Anal. Calcd for $C_{19}H_{13}F_2NO$: C, 73.78; H, 4.24; N, 4.53. Found: C, 72.65; H, 4.20; N, 4.45.

Preparation 33 N,N-Diethyl-N-(2-{[6-fluoro-9-(4-fluorobenzyl)-9H-carbazol-4-yl]oxy}ethyl)amine 6-Fluoro-9-(4-fluorobenzyl)-9H-carbazol-4-ol (0.0584 g, 0.19 mmol), 2-diethylaminoethylchloride hydrochloride (0.0593 g, 0.35 mmol), potassium carbonate (0.0926 g, 0.63 mmol), sodium iodide (0.0061 g, 0.041 mmol) and DMF (2 mL) are heated at 85° C. for 3 h. After the mixture had cooled, it is partitioned between water and ethyl acetate. The combined organic layers are dried over magnesium sulfate and concentrated to an oil. The oil is chromatographed on silica gel (50 mL) using methanol/dichloromethane (1/99) to give 0.0471 g (61%) of the title compound; mp 75–76° C.; MS (ESI+) for $C_{25}H_{26}F_2N_2O$ m/z 409.3 (M+H)+; IR (drift) 1585, 1507, 1481, 1461, 1343, 1269, 1221, 1159, 1145, 871, 820, 799, 776, 739, 712 cm$^{-1}$; $^1$H NMR (CDCl$_3$) δ1.14, 2.73, 3.10, 4.33, 5.44, 6.69, 6.93, 7.04–7.18, 7.36, 8.03. Anal. Calcd for $C_{25}H_{26}F_2N_2O$: C, 73.51; H, 6.41; N, 6.86. Found: C, 73.30; H, 6.59; N, 6.77.

Preparation 34 6-Methyl-1,2,3,9-tetrahydro-4H-carbazol-4-one p-Tolylhydrazine hydrochloride (8.6693 g, 0.0547 mol) is added in portions to a solution of 1,3-cyclohexanedione (6.00 g, 0.053 mol) in water (100 mL). The mixture is allowed to stir for three days at room temperature. The resulting solids are collected by filtration, washed with water and vacuum dried at 56° C. for 30 min and then overnight at room temperature to give the hydrazone. The hydrazone, p-toluene sulfonic acid monohydrate (8.31 g, 0,044 mol) and toluene (350 mL) are heated at 120° C. for 2.5 h. After cooling, the toluene layer is decanted and washed with water and aq. sodium bicarbonate, then dried over sodium sulfate and concentrated to dryness. The residue left behind in the round bottom flask is dissolved in dichloromethane and washed with water and aq. sodium bicarbonate (emulsion observed) and the organic layer is dried over sodium sulfate and concentrated to dryness. The solids in the emulsion are collected and washed with water, followed by ether and vacuum dried at room temperature to give 3.2168 g (39%) of the title compound. The solids obtained from the extractions are combined and chromatographed on silica gel (250 mL) using methanol/dichloromethane (0/100 to 2/98 to 4/96) and then triturated in ethyl acetate/dichloromethane/methanol/ heptane to give 0.4377 g (5%) of the title compound. An aliquot is chromatographed on silica gel (15 mL) using dichloromethane (100%) and then precipitated from dichloromethane/methanol/hexane; mp>255° C.; MS (ESI–) for $C_{13}H_{13}NO$ m/z 198.0 (M–H)$^-$; IR (drift) 3182, 3155, 3121, 3079, 3062, 3027, 2936, 1615, 1586, 1471, 1377, 1215, 1185, 1123, 798 cm$^{-1}$; $^1$H NMR (CD$_3$OD) δ2.21, 2.41, 2.53, 2.98, 7.02, 7.23, 7.83, NH not seen. Anal. Calcd for $C_{13}H_{13}NO$: C, 78.36; H, 6.58; N, 7.03. Found (av): C, 77.70; H, 6.55; N, 6.96.

Preparation 35 9-Benzyl-6-methyl-1,2,3,9-tetrahydro-4H-carbazol-4-one

6-Methyl-1,2,3,9-tetrahydro-4H-carbazol-4-one (7.6342 g, 0.038 mol) is added to a slurry of pentane-washed NaH (1.9563 g, 0.049 mol) in DMF (43 mL) and, after stirring for 20 min, benzyl bromide (0.58 mL, 0.0011 mol) is added. The mixture is cooled with a cold water bath and additional DMF (9 mL) is added to thin the slurry. After the slurry is stirred for 34 min, it is partitioned between water and ethyl acetate. The combined organic layers are dried over magnesium sulfate and concentrated to dryness. The resulting solids are recrystallized from ethyl acetate/dichloromethane/heptane to give 9.23 g (83%) of the title compound. The filtrate from the recrystallization is chromatographed on silica gel (225 mL) using methanol/dichloromethane (1/99) to give 1.14 g (10%) of the title compound; mp 179–179.5° C.; MS (ESI+) for $C_{20}H_{19}NO$ m/z 290.1 (M+H)$^+$; IR (drift) 2938, 1631, 1521, 1468, 1447, 1386, 1360, 1189, 1105, 953, 795, 757, 731, 702, 654 cm$^{-1}$; $^1$H NMR (CDCl$_3$) δ2.21, 2.46, 2.58, 2.86, 5.30, 7.03, 7.14, 7.28, 8.11. Anal. Calcd for $C_{20}H_{19}NO$: C, 83.01; H, 6.62; N, 4.84. Found: C, 82.61; H, 6.75; N, 4.76.

Preparation 36 9-Benzyl-6-methyl-9H-carbazol-4-ol

Pyridinium bromide perbromide (11.9436 g, 0.0373 mol) is added to a mixture of 9-benzyl-6-methyl-1,2,3,9-tetrahydro-4H-carbazol-4-one (8.93 g, 0.0309 mol) in dry THF (42 mL) and dry DMF (30 mL) and the mixture is heated to 75° C. After stirring for 6 h, THF is removed under reduced pressure and the residue is partitioned between dichloromethane and brine. The combined organic layers are washed with dilute sodium thiosulfate/brine and the combined organic layers are dried over magnesium sulfate and concentrated under high vacuum to give an oil. Hexane is added to the oil and solids precipitated. These solids are upgraded by precipitation from dichloromethane/ethyl acetate/hexane and vacuum dried at room temperature. The soilds are combined with lithium bromide (3.5386 g, 0.041 mol), lithium carbonate (2.7427 g, 0.037 mol) and dry DMF (72 mL) and heated at 120° C. for 1.5 h. DMF then is removed under high vacuum and the mixture is partitioned between dichloromethane and water. The combined organic layers are washed with water and the aqueous layer is backwashed with dichloromethane. The combined organic layers are dried over sodium sulfate and concentrated to an oil. The oil is chromatographed on silica gel (300 mL) using ethyl acetate/heptane (30/70). The product fractions are rechromatographed on silica gel (200 mL) using ethyl acetate/heptane (10/90) to give 3.75 g (42%) of 9-benzyl-6-methyl-9H-carbazol-4-ol containing a significant amount of 9-benzyl-3-bromo-6-methyl-9H-carbazol-4-ol as an impurity. The material is purified by reduction of the bromide. 9-Benzyl-6-methyl-9H-carbazol-4-ol. The mixture (2.25 g, 0.0078 mol) is dissolved in dry THF (8 mL) is added to a slurry of lithium aluminum hydride (0.7604 g, 0.020 mol) in dry THF (42 mL). The mixture is stirred overnight at 75–80° C. The mixture then is cooled and water (0.8 mL) is added followed by 15% NaOH (0.8 mL) and then water (2.4 mL). The solids are removed by filtration and washed with THF. The filtrate is concentrated to dryness and the residue is chromatographed on silica gel (50 mL) using dichloromethane (100%). Recrystallization from dichloromethane/hexane give 1.48 g (52%) of the title compound; mp 160–161° C.; MS (ESI+) for $C_{20}H_{17}NO$ m/z 288.2 (M+H)$^+$; IR (drift) 3294, 1468, 1450, 1338, 1302, 1281, 1238, 1147, 1117, 790, 779, 746, 720, 714, 703 cm$^{-1}$; $^1$H NMR (CDCl$_3$) δ2.54, 5.29, 5.47, 6.57, 6.93, 7.12, 7.23, 8.12. Anal. Calcd for $C_{20}H_{17}NO$: C, 83.59; H, 5.96; N, 4.87. Found: C, 83.51; H, 6.03; N, 4.94.

Example 45

N-{2-[(9-Benzyl-6-methyl-9H-carbazol-4-yl)oxy] ethyl}-N,N-diethylamine

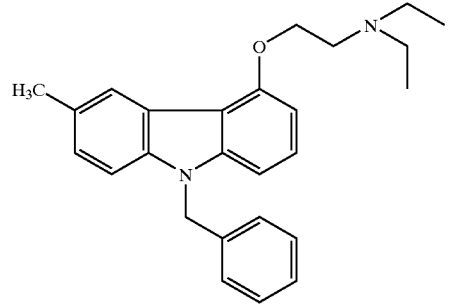

9-Benzyl-6-methyl-9H-carbazol-4-ol (0.0597 g, 0.21 mmol), 2-diethylaminoethylchloride hydrochloride (0.0565 g, 0.33 mmol), potassium carbonate (0.1007 g, 0.73 mmol), sodium iodide (0.0054 g, 0.036 mmol) and DMF (1 mL) are heated at 85° C. for 4.5 h. After the mixture had cooled, it is partitioned between water and ether. The aqueous layer is also washed twice with ethyl acetate. The combined organic layers are dried over magnesium sulfate and concentrated to dryness. The residue is chromatographed on silica gel (60 mL) using methanol/dichloromethane (1/99 to 3/97 to 5/95) to give 0.0605 g (75%) of the title compound containing N-{2-[(9-benzyl-3-bromo-6-methyl-9H-carbazol-4-yl)oxy] ethyl}-N,N-diethylamine as an impurity. Attempts at purifying this material through recrystallization are unsuccessfull; MS (ESI+) for $C_{26}H_{30}N_2O$ m/z 387.3 (M+H)$^+$. $^1$H NMR (CDCl$_3$) δ1.17 2.53, 2.78, 3.17, 4.37, 5.47, 6.68, 6.96, 7.11, 7.21–7.34, 8.17.

Preparation 37 2-[(9-Benzyl-6-methyl-9H-carbazol-4-yl)oxy]acetonitrile

A mixture 9-benzyl-6-methyl-9H-carbazol-4-ol (1.4172 g, 0.0049 mol), potassium carbonate (0.8184 g, 0.0059 mol), bromoacetonitrile (0.75mL, 0.011 mol) and DMF (18 mL) is stirred at room temperature for 3 h. The mixture is then partitioned between water and dichloromethane and the combined organic layers are dried over sodium sulfate and concentrated to a residue. Water is added to the residue and solids precipitated. The solids are collected by filtration and washed with water, followed by a little hexane, and then vacuum dried at room temperature. The solids are chromatographed on silica gel (150 mL) using dichloromethane (100%) to give 1.4723 g (91%) of the title compound. An aliquot is recrystallized from ethyl acetate/hexane, chromatographed on silica gel (50 mL) using ethyl acetate/hexane (20/80) and then recrystallized again from ethyl acetate/dichloromethane/hexane; mp 188–188.25° C.; MS (ESI+) for $C_{22}H_{18}N_2O$ m/z 327.2 (M+H)$^+$; IR (drift) 1497, 1467, 1447, 1365, 1340, 1305, 1264, 1237, 1152, 1126, 1053, 799, 781, 754, 711 cm$^-$; $^1$H NMR (CDCl$_3$) δ2.54, 5.06, 5.49, 6.73, 7.10, 7.25, 7.36, 8.10. Anal. Calcd for $C_{22}H_{18}N_2O$: C, 80.96; H, 5.56; N, 8.58. Found: C, 80.62; H, 5.68; N, 8.55.

Example 46

2-[(9-Benzyl-6-methyl-9H-carbazol-4-yl)oxy]ethylamine

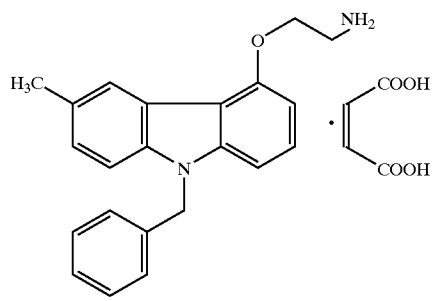

Borane-methyl sulfide (1.2 mL, 0.013 mol) is added to a mixture of 2-[(9-benzyl-6-methyl-9H-carbazol-4-yl)oxy]acetonitrile (1.3337 g, 0.0041 mol) in dry THF (35 mL) and the mixture is allowed to stir at room temperature for 5.5 h. The excess borane then is cautiously quenched with methanol and the mixture is concentrated under reduced pressure. Methanol and dichloromethane are added to the residue and the solution is again concentrated under reduced pressure (repeated twice). The solids are then dissolved in methanol/dichloromethane with heating and 4N HCl (10 mL) is added. The mixture is stirred for 15 min while being warmed slightly. The solvent is then removed under reduced pressure and the residue is partitioned between dichloromethane and aq. sodium bicarbonate. The combined organic layers are dried over sodium sulfate and concentrated to dryness. The residue is chromatographed on silica gel (300 mL) using methanol/dichloromethane (2/98 and 6/94) to give 0.89 g (66%) of the title compound. The salt of 2-[(9-benzyl-6-methyl-9H-carbazol-4-yl)oxy]ethylamine (0.2310 g, 0.70 mmol) is formed with maleic acid in dichloromethane and recrystallized from methanol/dichloromethane/hexane to give 0.2051 g (66%) of the maleic acid salt; mp 187.5–188° C.; MS (ESI+) for $C_{22}H_{22}N_2O$ m/z 331.3 (M+H)$^+$; IR (drift) 3027, 2984, 2926, 2887, 1601, 1579, 1497, 1483, 1465, 1364, 1344, 1267, 1150, 865, 747 cm$^{-1}$; $^1$H NMR (CD$_3$OD) δ2.52, 3.59, 4.52, 5.54, 6.23, 6.77, 7.09, 7.22, 7.33, 8.16, NH$_2$ not seen. Anal. Calcd for $C_{22}H_{22}N_2O\cdot C_4H_4O_4$: C, 69.94; H, 5.87; N, 6.27. Found: C, 69.93; H, 5.90; N, 6.29.

Preparation 38 2-[(9-Benzyl-6-methyl-9H-carbazol-4-yl)oxy]ethylformamide

A mixture of 2-[(9-benzyl-6-methyl-9H-carbazol-4-yl)oxy]ethylamine (0.2974 g, 0.90 mmol), dichloromethane (4 mL) and ethyl formate (4 mL) is heated at 62° C. Additional dichloromethane (6 mL) and ethyl formate (6 mL) are added. After 4 h, the mixture is concentrated to dryness and the residue is chromatographed on silica gel (100 mL) using methanol/dichloromethane (4/96). The resulting solids are recrystallized from ethyl acetate/dichloromethane/hexane to give 0.2716 g (84%) of the title compound; $^1$H NMR (CDCl$_3$) δ2.55, 3.94, 4.36, 5.48, 6.11, 6.64, 6.99, 7.11, 7.24, 7.32, 8.06, 8.28.

Example 47

N-{2-[(9-Benzyl-6-methyl-9H-carbazol-4-yl)oxy]ethyl}-N-methylamine

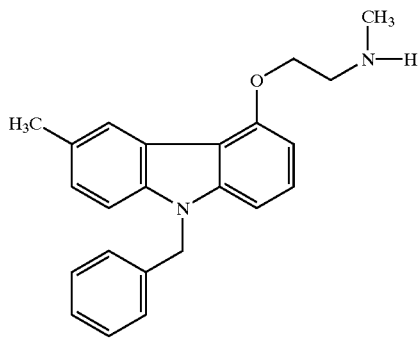

Borane-methyl sulfide (0.12 mL, 0.0013 mol) is added to a mixture of 2-[(9-benzyl-6-methyl-9H-carbazol-4-yl)oxy]ethylformamide (0.1565 g, 0.0013 mol) in dry THF (3 mL) and the mixture is stirred overnight at room temperature. The excess borane is cautiously quenched with methanol and the mixture is concentrated under reduced pressure. Methanol and dichloromethane are added to the residue and the solution is again concentrated under reduced pressure (repeated twice). The solids are then dissolved in methanol/dichloromethane and conc. HCl (27 drops) is added. After the mixture had stirred for 1.3 h, the solvent is removed under reduced pressure and the residue is partitioned between dichloromethane and aq. sodium bicarbonate. The combined organic layers are dried over sodium sulfate and concentrated to an oil. The oil is chromatographed on silica gel (40 mL) using acetone/dichloromethane/0.25% NH$_4$OH (10/90, 20/80 and 50/50) to give 0.1300 g (86%) of the title compound; mp 96–96.75° C.; MS (ESI+) for $C_{23}H_{24}N_2O$ m/z 345.2 (M+H)$^+$; IR (drift) 1600, 1580, 1467, 1449, 1341, 1307, 1268, 1242, 1151, 1128, 794, 779, 744, 718, 708 cm$^{-1}$; $^1$H NMR (CDCl$_3$) δ2.54, 2.61, 3.22, 4.39, 5.48, 6.68, 6.96, 7.11, 7.24, 7.31, 8.09. Anal. Calcd for $C_{23}H_{24}N_2O$: C, 80.20; H, 7.02; N, 8.13. Found: C, 79.88; H, 7.15; N, 8.12.

Preparation 39 9-(4-Fluorobenzyl)-6-methyl-1,2,3,9-tetrahydro-4H-carbazol-4-one

6-Methyl-1,2,3,9-tetrahydro-4H-carbazol-4-one (0.5457 g, 0.027 mol) is added to a slurry of pentane-washed NaH (0.1369 g, 0.0034 mol) in DMF (3 mL) and after stirring for 20 min, p-fluorobenzyl bromide (0.42 mL, 0.0034 mol) is added, followed by additional DMF (2 mL). After the slurry had stirred for 2.5 h, it is partitioned between water and ethyl acetate. The combined organic layers are washed with water, dried over sodium sulfate and concentrated to dryness. The resulting solids are chromatographed on silica gel (200 mL) using dichloromethane (100%) to give 0.6929 g (82%) of the title compound. An aliquot is recrystallized from ethyl acetate/heptane; mp 209.5–210° C.; MS (ESI+) for $C_{20}H_{18}FNO$ m/z 308.2 (M+H)$^+$; IR (drift) 2939, 1629, 1510, 1467, 1449, 1413, 1362, 1225, 1219, 1190, 1158, 1107, 1094, 832, 797 cm$^{-1}$; $^1$H NMR (CDCl$_3$) δ2.23, 2.47, 2.59, 2.85, 5.27, 6.99, 7.05, 7.12, 8.11. Anal. Calcd for C$_{20}$H$_{18}$FNO: C, 78.15; H, 5.90; N, 4.56. Found: C, 77.64; H, 5.87; N, 4.44.

Preparation 40 9-(4-Fluorobenzyl)-6-methyl-9H-carbazol-4-ol

Pyridinium bromide perbromide (0.8153 g, 0.0026 mol) is added to a mixture of 9-(4-fluorobenzyl)-6-methyl-1,2,3,9-tetrahydro-4H-carbazol-4-one (0.6351 g, 0.0021 mol) in dry THF (4.2 mL) and dry DMF (3 mL) and the mixture is heated to 75° C. After stirring for 6 h, additional pyridinium bromide perbromide (0.0951 g, 0.30 mmol) is added and the mixture is stirred another hour. After storing in the freezer overnight, the mixture is again heated for another 40 min. THF is removed under reduced pressure and the residue is partitioned between dichloromethane and brine. The combined organic layers are washed with dilute sodium thiosulfate/brine and the aqueous layer is backwashed with dichloromethane. The combined organic layers are dried over magnesium sulfate and concentrated to dryness. The residue is combined with lithium bromide (0.4092 g, 0.0047 mol), lithium carbonate (0.3652 g, 0.0049 mol) and dry DMF (12 mL) and heated at 120° C. for 1.5 h. DMF is removed under high vacuum and the mixture is partitioned between dichloromethane and water. The combined organic layers are dried over sodium sulfate and concentrated to dryness. The residue is chromatographed on silica gel (100 mL) using hexane (100%, to remove oil from sample) followed by ethyl acetate (100%). The residue is chromatographed again on silica gel (125 mL) using ethyl acetate/heptane (10/90) to give 0.0505 g (8%) of the title compound; MS (ESI−) for C$_{20}$H$_{16}$FNO m/z 304.1 (M−H)$^−$; $^1$H NMR (CDCl$_3$) δ2.54, 5.33, 5.43, 6.57, 6.93, 7.08, 7.24, 8.12.

Example 48

N,N-Diethyl-N-(2-{[9-(4-fluorobenzyl)-6-methyl-9H-carbazol-4-yl]oxy}ethyl)amine

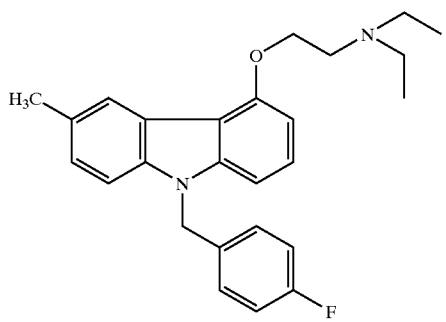

9-(4-Fluorobenzyl)-6-methyl-9H-carbazol-4-ol (0.0505 g, 0.17 mmol), 2-diethylaminoethylchloride hydrochloride (0.0411 g, 0.24 mmol), potassium carbonate (0.1018 g, 0.74 mmol), sodium iodide (0.0046 g, 0.031 mmol) and DMF (3 mL) are heated at 85° C. for 3 h. After the mixture had cooled, it is partitioned between water and ethyl acetate. The combined organic layers are dried over magnesium sulfate and concentrated to dryness. The residue is chromatographed on silica gel (60 mL) using methanol/dichloromethane (1/99 to 2/98 to 4/96) to give 0.0332 g (50%) of the title compound; MS (ESI+) for C$_{26}$H$_{29}$FN$_2$O m/z 405.3 (M+H)$^+$; IR (drift) 2966, 1601, 1506, 1460, 1339, 1269, 1242, 1218, 1150, 1127, 1054, 790, 781, 746, 717 cm$^{-}$; $^1$H NMR (CDCl$_3$) δ1.90, 2.55, 2.80, 3.18, 4.39, 5.46, 6.71, 6.94, 7.07, 7.22, 7.33, 8.19. Anal. Calcd for C$_{26}$H$_{29}$FN$_2$O: C, 77.20; H, 7.22; N, 6.93. Found: C, 75.79; H, 7.61; N, 6.55.

Example 49

2-({2-[(9-benzyl-9H-carbazol-4-yl)oxy]ethyl}amino)-1-ethanol and its maleic acid salt

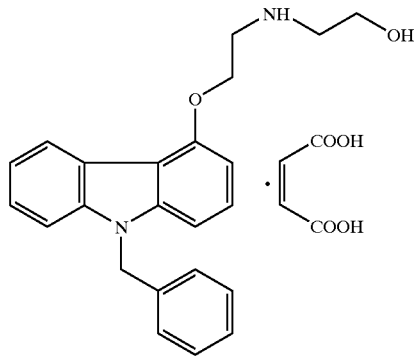

To a mixture of 9-benzyl-4-(2-bromoethoxy)-9H-carbazole (0.2350 g, 0.618 mmol), ethanolamine (0.41 ml, 0.68 mmol) and acetonitrile (10 ml) is added diisopropylethylamine (0.118 ml, 0.68 mmol). The mixture is refluxed at 85° C. for 24 h. The mixture is then concentrated, partitioned between CH$_2$Cl$_2$ and brine. The organic layer is washed with water and dried over magnesium sulfate. Column chromatography (30 ml silica gel) using methanol/CH$_2$Cl$_2$ (5/95) gave an oil, which is converted to the maleic acid salt to give 0.108 g (37%) of the title compound: mp 160° C.; IR (drift) 1580, 1532, 1499, 1487, 1458, 1380, 1356, 1343, 1334, 1268, 1146, 1113, 748, 714, 705 cm$^{-1}$; $^1$H NMR (300 MHz, DMSO-d6) δ3.18, 3.30, 3.69, 4.50, 5.27, 5.64, 5.99, 6.78, 7.09, 7.19, 7.36, 7.57, 8.30, 8.66. Anal. Calcd for C$_{23}$H$_{24}$N$_2$O$_2$.C$_4$H$_4$O$_4$.0.5 H$_2$O: C, 66.79; H, 6.02; N, 5.77. Found: C, 66.58; H, 5.89; N, 5.69.

Preparation 41 9H-Carbazol-4-ol 1,2,3,9-Tetrahydro-4H-carbazol-4-one (11.59, 0.063 mol), anhydrous lithium chloride (10.76 g, 0.255 mol), anhydrous copper (II) chloride (17.73 g, 0.132 mol) and DMF (70 mL) are combined and heated at 62° C. for 28 h. The mixture is cooled and the resulting solids are collected and washed with water followed by hexane. The solids are triturated four times in ethyl acetate at 80° C. Each time the filtrate is washed with water and the organic layer is dried over sodium sulfate and concentrated to dryness. The solids collected by filtration are then dissolved in dichloromethane/methanol, dried over sodium sulfate and concentrated to dryness. The combined solids gave 12.29 g of the chloro intermediate. A mixture of the chloro intermediate (6.52 g, 0.030 mol), lithium bromide (5.464 g, 0.063), lithium carbonate (4.530, 0.061 mol) and dry DMF (80 mL) is heated at 120° C. for 7.5 h and then stirred for two days at room temperature. The mixture is partitioned between water and dichloromethane and the combined organic layers are washed with brine, dried over sodium sulfate and concentrated to dryness. The resulting residue is chromatographed on silica gel (300 mL) using ethyl acetate/hexane (20/80) to give 2.543 g (42%) of the title compound; MS (ESI+) for C$_{12}$H$_9$NO m/z 184.1 (M+H)$^+$; $^1$H NMR (CDCl$_3$) δ5.32, 6.60, 7.04, 7.27, 7.43, 8.07, 8.29.

Preparation 42 2-(9H-Carbazol-4-yloxy)acetonitrile

A mixture of 9H-carbazol-4-ol (2.543 g, 0.014 mol), potassium carbonate (0.2.386 g, 0.017 mol), bromoacetonitrile (2.5 mL, 0.036 mol) and DMF (42 mL) is stirred at room temperature for 4 h. The mixture is then partitioned between water and ethyl acetate. The combined organic layers are dried over sodium sulfate and concentrated to a residue. The resulting residue is chromatographed on silica gel (200 mL) using ethyl acetate/hexane (20/80) to give 0.703 g (23%) of the title compound; mp 120–120.5° C.; MS (ESI−) for $C_{14}H_{10}N_2O$ m/z 221.0 (M−H)−; IR (drift) 3399, 1605, 1585, 1508, 1452, 1346, 1336, 1269, 1242, 1212, 1106, 785, 757, 750, 723 cm$^{-1}$; $^1$H NMR (CDCl$_3$) δ5.07, 6.76, 7.21, 7.29, 7.38–7.47, 8.18, 8.28. Anal. Calcd for $C_{14}H_{10}N_2O$: C, 75.66; H, 4.53; N, 12.60. Found: C, 75.41; H, 4.52; N, 12.48.

Preparation 43 2-({9-[(5-Chloro-1-benzothiophen-3-yl)methyl]-9H-carbazol-4-yl}oxy)acetonitrile 2-(9H-Carbazol-4-yloxy)acetonitrile (0.146 g, 0.66 mmol)) is added to a slurry of pentane-washed NaH (0.0441 g, 0.0011 mol) in DMF (1 mL) and allowed to stir for 20 min at room temperature. 3-(Bromomethyl)-5-chlorobenzothiophene (0.229 g, 0.88 mmol) is added and after stirring for 1 h the mixture is partitioned between ethyl acetate and water. The combined organic layers are dried over magnesium sulfate and concentrated to an oil. The oil is chromatographed on silica gel (75 mL) using ethyl acetate/hexane (20/80) and solids are precipitated using dichloromethane/hexane to give 0.148 g (56%) of the title compound; MS (ESI+) for $C_{23}H_{15}ClN_2OS$ m/z 425.2 (M+Na); IR (drift) 1581, 1460, 1439, 1332, 1279, 1232, 1221, 1155, 1148, 1115, 1079, 833, 780, 752, 717 cm$^{-1}$; $^1$H NMR (CDCl$_3$) δ5.10, 5.70, 6.72, 6.80, 7.12, 7.28–7.47, 7.80, 7.87, 8.36. Anal. Calcd for $C_{23}H_{15}ClN_2OS$: C, 68.57; H, 3.75; N, 6.95. Found: C, 68.87; H, 4.22; N, 6.56.

Example 50

2-({9-[(5-Chloro-1-benzothiophen-3-yl)methyl]-9H-carbazol-4-yl}oxy)ethylamine, methane sulfonate salt

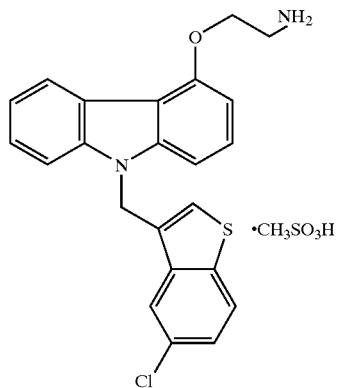

A mixture of 2-({9-[(5-chloro-1-benzothiophen-3-yl)methyl]-9H-carbazol-4-yl}oxy)acetonitrile (0.0915 g, 0.23 mmol), dry THF (2 mL) and borane-methyl sulfide (0.07 mL, 0.77 mmol) is stirred at 83° C. for 1.5 h. The mixture is then cooled, the excess borane is cautiously quenched with methanol and the mixture is concentrated under reduced pressure. Twice more methanol and dichloromethane are added to the residue and the solution is again concentrated under reduced pressure. The solids are slurried in methanol/dichloromethane and conc. HCl (approx. 1.5 mL) is added and the mixture is heated at 64° C. for 40 min. After cooling, the mixture is concentrated to dryness under reduced pressure and the residue is partitioned between dichloromethane and aq. sodium bicarbonate. The combined organic layers are dried over sodium sulfate and concentrated to dryness. The residue is chromatographed on silica gel (50 mL) using methanol/dichloromethane (2/98 and 4/96 and 6/94) to give the desired free base. The methane sulfonate salt is formed by dissolving the free base (0.0547 g, 0.13 mmol) in dichloromethane/methanol and adding methanesulfonic acid (0.0.013 g, 0.14 mmol) to the solution. Solids crystallized and are collected, washed with dichloromethane and vacuum dried at room temperature to give 0.0481 g (42%) of the title compound; mp>256° C.; MS (ESI+) for $C_{23}H_{19}ClN_2OS$ m/z 407.2 (M+H)$^+$. IR (drift) 1585, 1457, 1328, 1269, 1240, 1221, 1197, 1180, 1165, 1149, 1044, 783, 772, 750, 717 cm$^{-1}$; $^1$H NMR (CD$_3$OD) δ2.71, 3.61, 4.55, 5.82, 6.85, 7.00, 7.20–7.53, 7.86, 8.43. Anal. Calcd for $C_{23}H_{19}ClN_2OS \cdot CH_4O_3S$: C, 57.30; H, 4.61; N, 5.57. Found: C, 56.9; H, 4.68; N, 5.49.

Preparation 44 2-({9-[(2-methyl-1,3-thiazol-4-yl)methyl]-9H-carbazol-4-yl}oxy)acetonitrile 2-(9H-Carbazol-4-yloxy)acetonitrile (0.143 g, 0.64 mmol)) is added to a slurry of pentane-washed NaH (0.0825 g, 0.0021 mol) in DMF (1 mL) and allowed to stir for 20 min at room temperature. 4-Chloromethyl-2-methylthiazole hydrochloride (0163 g, 0.89 mmol) is added and after stirring for 2 h the mixture is partitioned between ethyl acetate and water. The combined organic layers are dried over magnesium sulfate and concentrated to an oil. The oil is chromatographed on silica gel (75 mL) using ethyl acetate/hexane (20/80 and 40/60) and solids are crystallized from dichloromethane/ether to give 0.162 g (76%) of the title compound; MS (ESI+) for $C_{19}H_{15}N_3OS$ m/z 334.2 (M+H)$^+$; IR (drift) 1581, 1459, 1440, 1341, 1333, 1275, 1228, 1215, 1182, 1157, 1151, 1113, 782, 754, 718 cm$^{-1}$; $^1$H NMR (CDCl$_3$) δ2.74, 5.09, 5.62, 6.38, 6.78, 7.19, 7.31, 7.44, 8.32. Anal. Calcd for $C_{19}H_{15}N_3OS$: C, 68.45; H, 4.53; N, 12.60. Found: C, 68.27; H, 4.53; N, 12.33.

Example 51

2-({9-[(2-Methyl-1,3-thiazol-4-yl)methyl]-9H-carbazol-4-yl}oxy)ethylamine, methane sulfonate salt

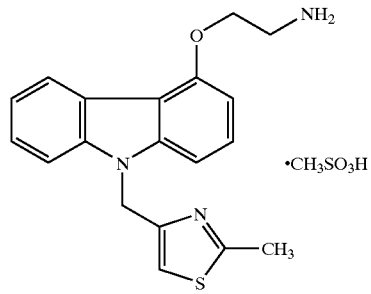

A mixture of 2-({9-[(2-methyl-1,3-thiazol-4-yl)methyl]-9H-carbazol-4-yl}oxy)acetonitrile (0.1229 g, 0.37 mmol), dry THF (3 mL) and borane-methyl sulfide (0.11 mL, 0.0012 mol) is stirred at 83° C. for 3 h. The mixture is then cooled, the excess borane is cautiously quenched with methanol and the mixture is concentrated under reduced pressure. Methanol and dichloromethane are added to the residue and the solution is again concentrated under reduced pressure (repeated twice). The solids are heated at 60° C. in methanol/ dichloromethane and conc. HCl (2 mL) for 1 h. After cooling, the mixture is concentrated to dryness under reduced pressure and partitioned between dichloromethane and aq. sodium bicarbonate. The combined organic layers are dried over sodium sulfate and concentrated to dryness. The oil is chromatographed on silica gel (30 mL) using methanol/dichloromethane (2/98 and 4/96) to give 0.0754 g (61%) of the desired free base. The methane sulfonate salt is formed by dissolving the free base (0.0696 g, 0.21 mmol) in dichloromethane and adding methanesulfonic acid (0.0.0201 g, 0.21 mmol) to the solution. The solution is concentrated and the solids are recrystallized from ethyl acetate/ dichloromethane/methanol to give 0.0400 g (45%) of the title compound; mp 228.5–229.0° C.; MS (ESI+) for $C_{19}H_{19}N_3OS$ m/z 338.2 $(M+H)^+$; IR (drift) 1458, 1343, 1335, 1269, 1239, 1223, 1182, 1165, 1155, 1119, 1043, 782, 770, 751, 713 cm$^{-1}$; $^1$H NMR (CD$_3$OD) $\delta$2.65, 2.69, 3.58, 4.52, 5.60, 6.75, 6.81, 7.23, 7.39, 7.51, 8.38. Anal. Calcd for $C_{19}H_{19}N_3OS.CH_4O_3S$: C, 55.41; H, 5.35; N, 9.69. Found: C, 55.08; H, 5.39; N, 9.54.

Preparation 45 9-Benzyl-3,3-dichloro-1,2,3,9-tetrahydro-4H-carbazol-4-one

A mixture of 9-benzyl-1,2,3,9-tetrahydro-4H-carbazol-4-one (0.491 g, 1.78 mmol), copper (II) chloride (1.60 g, 8.92 mmol), LiCl (0.225 g, 5.34 mmol), and DMF (5 mL) is stirred at 105° C. for 2.5 h and then at 140° C. for an additional 1 h. After cooling, the mixture is stored overnight in the refrigerator and then partitioned between ethyl acetate and brine/aq. sodium bicarbonate and brine. The organic layer is dried over magnesium sulfate and concentrated to dryness. The resulting solid is used without further purification in the next step (to prepare 9-benzyl-3-chloro-9H-carbazol-4-ol. $^1$H NMR (CDCl$_3$) $\delta$3.03–3.10, 5.35, 7.03, 7.30, 8.31.

Preparation 46 9-Benzyl-3-chloro-9H-carbazol-4-ol

A mixture of 9-benzyl-3,3-dichloro-1,2,3,9-tetrahydro-4H-carbazol-4-one (0.225 g, 1.78 mmol), LiCl (0.225 g, 5.34 mmol), Li$_2$CO$_3$ (0.395 g, 5.34 mmol), and DMF (6 mL) is heated at 135° C. for 45 min. After cooling, the mixture is partitioned between ethyl ether and aq. ammonium chloride/brine and brine. The organic layer is dried over magnesium sulfate and concentrated to dryness. Chromatography on silica gel (40 mL) using ethyl acetate/hexane (10/90) gave 0.382 g of 9-benzyl-3-chloro-9H-carbazol-4-ol. $^1$H NMR (CDCl$_3$) $\delta$5.48, 6.14, 6.88, 7.11, 7.12, 7.24–7.36, 7.43, 8.37.

Preparation 47 [(9-Benzyl-3-chloro-9H-carbazol-4-yl)oxy]acetonitrile

A mixture of 9-benzyl-3-chloro-9H-carbazol-4-ol (0.227 g, 0.739 mmol), bromoacetonitrile (0.177 g, 1.48 mmol), potassium carbonate (0.204 g, 1.48 mmol), and DMF (2 mL) is heated at 85° C. for 4 h, then allowed to cool and stir at room temperature for 12 h. Additional bromoacetonitrile (0.177 g) and potassium carbonate (0.204 g) are added and the mixture is heated again at 85° C. for 2 h. After cooling, the mixture is combined with that from another experiment run in the same manner (starting with 0.15 g of 9-benzyl-3-chloro-9H-carbazol-4-ol) and the combined mixtures are partitioned between ethyl acetate-aq. ammonium chloride/ brine and brine. The organic layer is dried over magnesium sulfate and concentrated to dryness. Chromatography on silica gel (55 mL) using ethyl acetate-hexane (10/90) gave 0.292 g of [(9-benzyl-3-chloro-9H-carbazol-4-yl)oxy] acetonitrile as a clear liquid. $^1$H NMR (CDCl$_3$) $\delta$5.07, 5.50, 7.11, 7.15, 7.25–7.47, 7.50, 8.34.

Example 52

2-[(9-Benzyl-3-chloro-9H-carbazol-4-yl)oxy] ethylamine, methanesulfonate salt

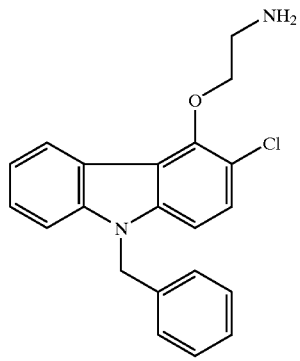

To [(9-benzyl-3-chloro-9H-carbazol-4-yl)oxy] acetonitrile (0.292 g, 0.842 mmol) in THF (6 mL) is added borane-methyl sulfide complex (0.24 mL, 2.53 mmol). The mixture is stirred at 80° C. for 2.5 h and then allowed to cool. MeOH is carefully added to the residue until gas evolution ceased and then the mixture is concentrated under vacuum. MeOH addition/removal is repeated two more times and then MeOH-dichloromethane (about 2 mL each) is added, followed by several drops of conc. HCl. The mixture is stirred for about 15 min and then taken to dryness under vacuum. After partitioning with dichloromethane and aq. sodium bicarbonate and drying, the residue is chromatographed on silica gel (50 mL) using MeOH-dichloromethane (2/98 to 4/96) to give 0.206 g (70%) of 2-[(9-benzyl-3-chloro-9H-carbazol-4-yl)oxy]ethylamine. The methanesulfonate salt is prepared by dissolving 2-[(9-benzyl-3-chloro-9H-carbazol-4-yl)oxy]ethylamine in MeOH and dichloromethane and adding methanesulfonic acid (0.0581 g). The mixture is concentrated to dryness under vacuum and the residue is crystallized from dichloromethane-hexane to give 0.206 g of 2-[(9-benzyl-3-chloro-9H-carbazol-4-yl) oxy]ethylamine, methanesulfonate salt as a white crystalline solid. $^1$H NMR (CDCl$_3$) $\delta$1.9, 3.29, 4.31, 5.49, 7.07, 7.12, 7.27, 7.35–7.49, 8.32.

Preparation 48 9H-Carbazol-4-ol

To a mixture of 1,2,3,9-tetrahydro-4H-carbazol-4-one (6.02 g, 32.5 mmol) in 1:1 ethylene glycol: p-dioxane (100 mL) at 80° C. is added copper (II) chloride (21 g, 156.2 mmol). The mixture is heated for 20 minutes. The mixture is then partitioned between water and ethyl acetate. The layers are separated and the organic layer is washed three times with water (200 mL). The organic layer is dried over anhydrous sodium sulfate, filtered, and concentrated. The residue is dissolved in DMF (100 mL) to which is added lithium bromide (7.04 g, 81.25 mmol) and lithium carbonate (6.0 g, 81.25 mmol). The mixture is heated at 120° C. for 4.5 hours. The mixture is then partitioned between water and ether. The ether layer is washed three times with water (200 mL). The ether layer is dried over anhydrous sodium sulfate, filtered and concentrated. Column chromatography, silica gel (800 mL), using $CH_2Cl_2$ as eluent gave 1.1 g (18%) of the title compound; $^1$H NMR (CDCl$_3$) δ5.26, 6.57, 7.01, 7.26, 7.41, 8.05, 8.26; Anal. Calcd for $C_{12}H_9NO$: C, 78.67; H, 4.95; N, 7.64. Found: C, 78.04; H, 4.94; N, 7.58.

Preparation 49 (9H-Carbazol-4-yloxy)acetonitrile

To a mixture of 9H-carbazol-4-ol (1.1 g, 6.0 mmol) in acetonitrile (100 mL) is added potassium carbonate (1.66 g, 12 mmol) and bromoacetonitrile (0.42 mL, 6.0 mmol). The mixture is stirred at room temperature for 20 h. The mixture is partitioned between water and $CH_2Cl_2$. The layers are separated and the organic layer dried over anhydrous sodium sulfate, filtered and concentrated. Column chromatography, silica gel (100 mL), using $CH_2Cl_2$ as eluent gave 1.13 g (85%) of the title compound; $^1$H NMR (DMSO-d$_6$) δ5.4, 6.81, 7.18, 7.36, 7.46, 8.09; Anal. Calcd for $C_{14}H_{10}N_2O$: C, 75.66; H, 4.53; N, 12.60. Found: C, 75.18; H, 4.56; N, 12.54.

Preparation 50 2-(9H-Carbazol-4-yloxy)ethylamine

To a mixture of (9H-carbazol-4-yloxy)acetonitrile (1.13 g, 5.1 mmol) in dry THF (50 mL) is added borane-methyl sulfide complex (1.4 mL, 15.3 mmol). The mixture is heated at 85° C. for 6 h. Methanol is added slowly until gas evolution ceased. The solvents are removed under reduced pressure. Methanol (20 mL) is added then removed under reduced pressure. Methanol (50 mL) and concentrated hydrochloric acid are added and the mixture heated at 65° C. overnight. The mixture is neutralized with saturated potassium carbonate and partitioned between water and $CH_2Cl_2$. The layers are separated and the organic layer washed twice with water (100 mL), dried over anhydrous sodium sulfate, filtered and concentrated. Column chromatography, silica gel (200 mL), using $CH_3OH/CH_2Cl_2$ (4/96) gave 0.61 g (53%) of the title compound; IR (drift) 3082, 1608, 1585, 1456, 1443, 1346, 1336, 1303, 1252, 1222, 1098, 911, 782, 750, 719 cm$^{-1}$. 1H NMR (DMSO-d6) δ3.05, 4.13, 6.65, 7.03, 7.12, 7.24, 7.31, 7.41, 8.12; Anal. Calcd for $C_{14}H_{14}N_2O$: C, 74.31; H, 6.24; N, 12.38. Found: C, 73.90; H, 6.32; N, 12.14.

Preparation 51 tert-Butyl 2-(9H-carbazol-4-yloxy)ethylcarbamate

To a mixture of sodium hydroxide (0.1 g, 2.6 mmol) in water (60 mL) is added 2-(9H-carbazol-4-yloxy)ethylamine (0.59 g, 2.6 mmol) in THF (10 mL). Boc anydride (0.567 g, 2.6 mmol) is slowly added and the mixture stirred at room temperature for 2 h. The mixture is partitioned between water and $CH_2Cl_2$. The layers are separated and the organic layer washed with water (50 mL). The organic layer is dried over anhydrous sodium sulfate, filtered and concentrated to give 0.84 g (100%) of the title compound; $^1$H NMR (CDCl$_3$) δ1.46, 3.75, 4.3, 5.1, 6.6, 7.05, 7.3, 7.32, 7.4, 8.12, 8.25; Anal. Calcd for $C_{19}H_{22}N_2O_3$: C, 69.92; H, 6.79; N, 8.58. Found: C, 66.47; H, 6.60; N, 7.94.

Example 53

2-{[9-(3-Bromobenzyl)-9H-carbazol-4-yl]oxy}ethylamine, maleic acid salt

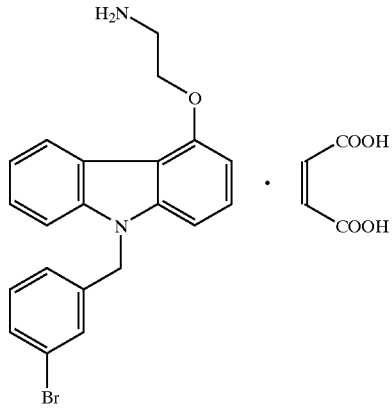

To a solution of sodium hydride (0.0059 g, 0.375 mmol) in dry DMF (2 mL) is added tert-butyl 2-(9H-carbazol-4-yloxy)ethylcarbamate (0.08 g, 0.245 mmol). The mixture is stirred for ½ h at room temperature. 1-Bromo-3-(bromomethyl)benzene (0.062 g, 0.248 mmol) is added and the mixture stirred at room temperature for 2 h. The mixture is partitioned between water and $CH_2Cl_2$. The layers are separated and the organic layer washed three times with water (5 mL). The organic layer is dried over anhydrous sodium sulfate, filtered and TFA (2 mL) is added. The mixture is stirred at room temperature for 30 minutes. The mixture is neutralized with saturated potassium carbonate. The layers are separated and the organic layer washed twice with water (5 mL). Column chromatography, silica gel (100 mL), using $CH_2Cl_2$: $CH_3OH$: NH$^4$OH (95:4:1) gave an oil. The oil is converted to the maleic acid salt to give 0.0731 g (58%) of the title compound; IR (drift) 1623, 1581, 1499, 1482, 1460, 1353, 1332, 1273, 1113, 1019, 999, 861, 782, 749, 717 cm$^-$. $^1$H NMR (DMSO-d$_6$) δ3.4, 4.4, 5.7, 6.0, 6.8, 7.04, 7.25, 7.37, 8.0, 8.36; Anal. Calcd for $C_{21}H_{19}BrN_2O \cdot C_4H_4O_4$: C, 58.72; H, 4.53; N, 5.48; Br, 15.63. Found: C, 58.37; H, 4.66; N, 5.37.

Example 54

2-{[9-(3-Fluorobenzyl)-9H-carbazol-4-yl]oxy}ethylamine, maleic acid salt

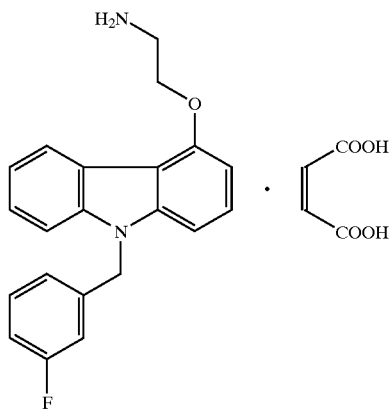

Following the procedure of Example 53, the title compound is prepared. IR (drift) 3051, 2938, 1618, 1586, 1500, 1485, 1460, 1360, 1335, 1271, 1247, 862, 781, 750, 715 cm$^{-1}$. MS (ESI+) for c21 h19 n2 o1 f$_{11}$ m/z 335.3 (M+H)$^+$. $^1$H NMR (DMSO-d$_6$) δ3.43, 4.4, 5.7, 6.0, 6.8, 6.9, 7.0, 7.3, 7.4, 7.6, 8.0, 8.4; Anal. Calcd for $C_{21}H_{19}FN_2O \cdot C_4H_4O_4$: C, 66.66; H, 5.15; N, 6.22. Found: C, 65.62; H, 5.21; N, 6.01.

Example 55

2-{[9-(4-Methylbenzyl)-9H-carbazol-4-yl]oxy}ethylamine, maleic acid salt

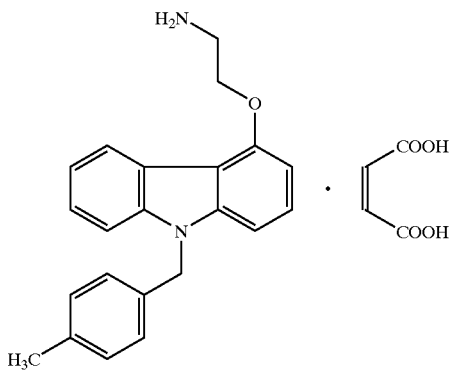

Following the procedure of Example 53, the title compound is prepared. IR (drift) 1581, 1531, 1499, 1483, 1461, 1353, 1343, 1333, 1112, 1019, 998, 861, 782, 750, 715 cm$^{-1}$. MS (ESI+) for c22 h22 n2 o$_1$ m/z 331.3 (M+H)$^+$. $^1$H NMR (DMSO-d$_6$) δ2.19, 3.4, 4.4, 5.6, 6.0, 6.7, 7.0, 7.18, 7.24, 7.4, 8.0, 8.3; Anal. Calcd for $C_{22}H_{22}N_2O \cdot C_4H_4O_4$: C, 69.94; H, 5.87; N, 6.27. Found: C, 68.73; H, 5.95; N, 5.93.

Example 56

2-{[9-(2-Fluorobenzyl)-9H-carbazol-4-yl]oxy}ethylamine, maleic acid salt

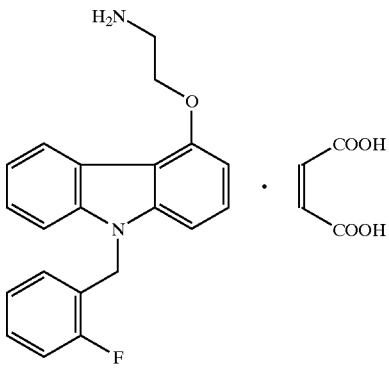

Following the procedure of Example 53, the title compound is prepared. IR (drift) 3046, 1623, 1585, 1488, 1460, 1352, 1334, 1275, 1177, 1145, 1113, 861, 782, 749, 714 cm$^{-1}$. MS (ESI+) for c21 h19 n2 f1 o$_1$ Anal m/z 335.3 (M+H)$^+$. $^1$H NMR (DMSO-d$_6$) δ3.4, 4.4, 5.69, 6.02, 6.7, 6.78, 6.98, 7.26, 7.37, 7.56, 8.04, 8.35; Calcd for $C_{21}H_{19}FN_2O \cdot C_4H_4O_4$: C, 66.66; H, 5.15; N, 6.22. Found: C, 66.10; H, 5.20; N, 6.06.

Example 57

2-{[9-(3-Methoxybenzyl)-9H-carbazol-4-yl]oxy}ethylamine, maleic acid salt

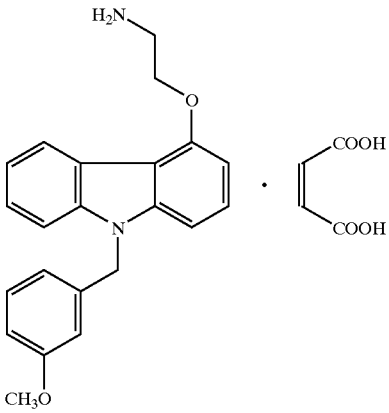

Following the procedure of Example 53, the title compound is prepared. IR (drift) 3045, 3005, 2947, 1622, 1598, 1531, 1488, 1459, 1353, 1336, 1271, 864, 752, 748, 718 cm$^{-1}$. MS (ESI+) for c22 h22 n2 o$_2$ Anal m/z 346.5 (M+H)$^+$. $^1$H NMR (DMSO-d$_6$) δ3.43, 3.63, 4.41, 5.6, 6.0, 6.5, 6.69, 6.78, 7.2, 7.4, 7.6, 8.0, 8.34; Calcd for $C_{22}H_{22}N_2O_2 \cdot C_4H_4O_4$: C, 67.52; H, 5.67; N, 6.06. Found: C, 66.81; H, 5.73; N, 5.87.

Example 58

2-{[9-(3,5-Dimethoxybenzyl)-9H-carbazol-4-yl]oxy}ethylamine, maleic acid salt

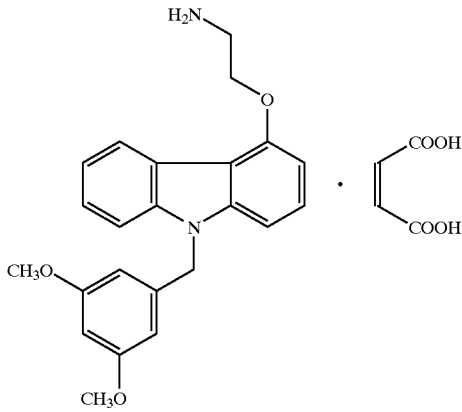

Following the procedure of Example 53, the title compound is prepared. IR (drift) 3046, 3001, 2958, 2837, 1596, 1551, 1532, 1499, 1482, 1459, 1351, 1205, 1157, 748, 711 cm$^{-1}$. MS (ESI+) for c23 h24 n2 o$_3$ m/z 377.4 (M+H)$^+$. $^1$H NMR (DMSO-d$_6$) δ3.42, 3.61, 4.41, 5.6, 6.0, 6.2, 6.3, 6.8, 7.2, 7.4, 7.6, 8.0, 8.3; Anal Calcd for $C_{23}H_{24}N_2O_3 \cdot C_4H_4O_4$: C, 65.84; H, 5.73; N, 5.69. Found: C, 65.21; H, 5.89; N, 5.42.

Example 59

2-{[9-(3-Methylbenzyl)-9H-carbazol-4-yl]oxy}ethylamine, maleic acid salt

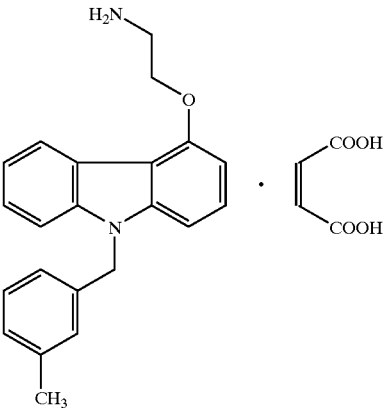

Following the procedure of Example 53, the title compound is prepared. IR (drift) 3053, 3026, 2958, 1579, 1535, 1525, 1517, 1499, 1483, 1460, 1355, 1334, 1271, 751, 716 cm$^{-1}$. MS (ESI+) for c22 h22 n2 o$_1$ m/z 331.34 (M+H)$^+$. $^1$H NMR (DMSO-d$_6$) δ3.43, 4.41, 5.59, 6.04, 6.77, 7.02, 6.99, 7.2, 7.37, 7.55, 8.0, 8.34; Anal Calcd for $C_{22}H_{22}N_2O \cdot C_4H_4O_4$: C, 69.94; H, 5.87; N, 6.27. Found: C, 67.42; H, 5.80; N, 5.75.

Example 60

2-{[9-(2-Methylbenzyl)-9H-carbazol-4-yl]oxy}ethylamine, maleic acid salt

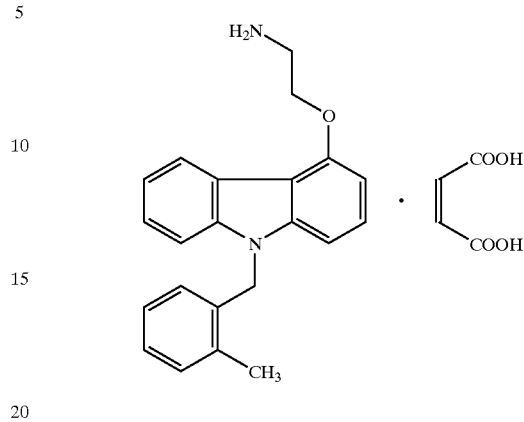

Following the procedure of Example 53, the title compound is prepared. IR (drift) 1627, 1595, 1580, 1531, 1517, 1498, 1483, 1460, 1352, 1343, 1272, 861, 749, 739, 716 cm$^{-1}$. MS (ESI+) for c22 h22 n2 o$_1$ m/z 331.35 (M+H)$^+$. $^1$H NMR (DMSO-d$_6$) δ2.4, 3.5, 4.4, 5.6, 6.0, 6.04, 6.78, 6.86, 7.1, 7.23, 7.33, 7.42, 8.06, 8.38; Anal Calcd for $C_{22}H_{22}N_2O \cdot C_4H_4O_4$: C, 69.94; H, 5.87; N, 6.27. Found: C, 69.08; H, 6.04; N, 5.97.

Preparation 52 6-Methoxy-1,2,3,9-tetrahydro-4H-carbazol-4-one

To a mixture of 4-methoxyphenyl hydrazine (0.359 g, 2.06 mmol) in toluene (30 mL) is added 1,3 cyclohexanedione (0.231 g, 2.06 mmol). The mixture is refluxed for 30 minutes. The toluene is removed under reduced pressure and the residue triturated in CH$_2$Cl$_2$: CH$_3$OH (95:5). A white solid is filtered to give 0.2903 g (65%) of the title compound; IR (drift) 3160, 3141, 3114, 3064, 1619, 1588, 1474, 1434, 1277, 1215, 1140, 1015, 844, 802, 791 cm$^{-1}$. MS (ESI+) for C13H13N1O2 m/z 216 (M+H)$^+$. $^1$H NMR (DMSO-d$_6$) δ2.08, 2.39, 2., 3.74, 6.74, 7.25, 7.43; Anal Calcd for $C_{13}H_{13}NO_2$: C, 72.54; H, 6.09; N, 6.51. Found: C, 71.48; H, 6.06; N, 6.45.

Preparation 53 9-Benzyl-6-methoxy-1,2,3,9-tetrahydro-4H-carbazol-4-one

To a slurry of 60% sodium hydride (0.76 g, 19.6 mmol) in DMF (20 mL) is added 6-methoxy-1,2,3,9-tetrahydro-4H-carbazol-4-one (3.84 g, 17.8 mmol) over a period of 5 minutes and benzyl bromide (2.4 mL, 19.6 mmol). The mixture is heated to 50° C. for 1 hour then room temperature overnight. The mixture is partitioned between water and CH$_2$Cl$_2$. The layers are separated and the organic layer washed with water (200 mL) and concentrated. The residue is triturated in hexanes and filtered to give 4.45 g (80%) of the title compound; mp 174–175° C., IR (drift) 2939, 1633, 1484, 1467, 1448, 1349, 1276, 1242, 1159, 1130, 1099, 854, 791, 762, 710 cm$^{-1}$. $^1$H NMR (DMSO-d$_6$) δ2.1, 2., 2.93, 3.75, 5.44, 6.77, 7.09, 7.28, 7.39, 7.51; Anal. Calcd for $C_{20}H_{19}NO_2$: C, 78.66; H, 6.27; N, 4.59. Found: C, 78.45; H, 6.31; N, 4.58.

Preparation 54 9-Benzyl-6-methoxy-9H-carbazol-4-ol

To a mixture of 9-benzyl-6-methoxy-1,2,3,9-tetrahydro-4H-carbazol-4-one (4.23 g, 13.85 mmol) in ethylene glycol:

p-dioxane ((1:1) 150 mL) is added copper (II) chloride (9.31 g, 69.26 mmol). The mixture is heated at 80° C. for 30 minutes. The mixture is partitioned between water and $Et_2O$. The layers are separated and the organic layer washed with water (100 mL). The ether layer is dried over anhydrous sodium sulfate, filtered and concentrated. The residue is dissolved in DMF (50 mL) to which is added lithium bromide (2.45 g, 28.3 mmol) and lithium carbonate (2.09 g, 28.3 mnmol). The mixture is heated at 120° C. for 5 h. The mixture is partitioned between water and ethyl acetate. The layers are separated and the organic layer washed twice with water (200 mL). Column chromatography (250 mL) silica gel using ethyl acetate/ hexanes (20/80) gave 2.5 g (73%) of the title compound; IR (drift) 3471, 1482, 1469, 1450, 1328, 1198, 1171, 1144, 805, 799, 780, 745, 724, 717, 701 $cm^{-1}$. $^1H$ NMR (DMSO-$d_6$) δ3.82, 5.54, 6.56, 6.97), 7.14, 7.23, 7.43, 7.72; Anal. Calcd for $C_{20}H_{17}NO_2$: C, 79.18; H, 5.65; N, 4.62. Found: C, 78.99; H, 5.75; N, 4.63.

Preparation 55 [(9-Benzyl-6-methoxy-9H-carbazol-4-yl)oxy]acetonitrile

To a mixture of 9-benzyl-6-methoxy-9H-carbazol-4-ol (1.21 g, 4.0 mmol) in DMF (25 mL) is added potassium carbonate (2.07 g, 15 mmol) and bromoacetonitrile (0.7 mL) 10 mmol). The mixture is heated at 120° C. overnight. The mixture is partitioned between water and $Et_2O$. The organic layer is washed twice with water (100 mL) and dried over anhydrous sodium sulfate. The residue is dissolved in $CH_2Cl_2$ and passed through a silica gel plug. The filtrates are concentrated to dryness to give 0.43 g (31%) of the title compound; IR (drift) 1487, 1469, 1449, 1439, 1291, 1275, 1211, 1181, 1170, 1147, 1120, 775, 745, 705, 697 $cm^{-1}$. $^1H$ NMR ($CDCl_3$) δ3.94, 5.06, 5.48, 6.7, 7.09, 7.24, 7.36, 7.81; Anal. Calcd for $C_{22}H_{18}N_2O_2$: C, 77.17; H, 5.30; N, 8.18. Found: C, 76.68; H, 5.31; N, 8.08.

Example 61

2-[(9-Benzyl-6-methoxy-9H-carbazol-4-yl)oxy]ethylamine

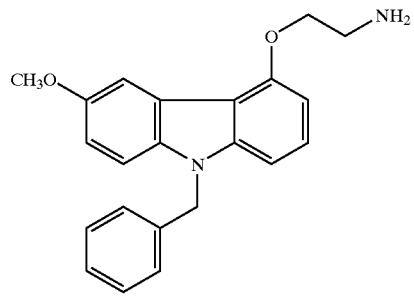

To a mixture of [(9-benzyl-6-methoxy-9H-carbazol-4-yl) oxy]acetonitrile (0.43 g, 1.26 mmol) in dry THF (20 mL) is added borane-methylsulfide complex (0.36 mL, 3.8 mmol). The mixture is heated at 85° C. overnight. Methanol is slowly added to the mixture until gas evolution ceased. The solvents are removed under reduced pressure. Methanol (20 mL) is added then removed under reduced pressure. Methanol (50 mL) and concentrated hydrochloric acid (10 mL) is added to the mixture and heated at 65° C. overnight. The mixture is neutralized with saturated potassium carbonate and partitioned between water and $CH_2Cl_2$. The layers are separated and the organic layer washed twice with water (100 mL). The $CH_2Cl_2$ is dried over anhydrous sodium sulfate and concentrated. Column chromatography with silica gel (60 mL) using 4% $CH_3OH$ in $CH_2Cl_2$ gave 0.371 g (85%) of the title compound; IR (drift) 1581, 1488, 1467, 1452, 1440, 1343, 1323, 1289, 1271, 1211, 1167, 1150, 1031, 742, 727 $cm^{-1}$. HRMS (FAB) calcd for $C_{22}H_{22}N_2O_2$+ $H_1$ 347.1759, found 347.1761. % Water (KF): 0.17. $^1H$ NMR ($CDCl_3$) δ3.28, 3.92, 4.28, 5.47, 6.65, 6.95, 7.02, 7.09, 7.21, 7.32, 7.87; Anal. Calcd for $C_{22}H_{22}N_2O_2$: C, 76.15; H, 6.41; N, 8.07. Found: C, 75.90; H, 6.38; N, 7.99.

Preparation 56 7-Methoxy-1,2,3,9-tetrahydro-4H-carbazol-4-one

To a chilled mixture of m-anisidine (10 g, 81 mmol) in water (200 mL) and concentrated hydrochloric acid (25 mL) is added sodium nitrite (5.6 g, 81 mmol) dissolved in water (30 mL). The mixture is stirred at 5° C. for one h. To this is added tin (II) chloride dihydrate (36.6 g, 162 mmol) dissolved in concentrated hydrochloric acid (75 mL). The mixture is allowed to warm to room temperature and stirred for 1 h. 1,3 cyclohexanedione (9.1 g, 81 mmol) is added and the mixture stirred for 2 h. The mixture is slowly neutralized with 10% NaOH. Filtered solids and washed with water (500 mL). The solids are then slurried in acetonitrile (600 mL), filtered and washed with acetonitrile (200 mL). The filtrates are dried over anhydrous sodium sulfate, filtered and concentrated. The residue is refluxed in TFA (70 mL) for 18 h. The mixture is partitioned between water and $CH_2Cl_2$. The organic layer is separated and washed twice with water (200 mL). The organic layer is dried over anhydrous sodium sulfate, filtered, and concentrated. Ethyl acetate (100 mL) is added to the residue and the solids filtered to give 2.29 g (13%) of the title compound; IR (drift) 3156, 3118, 3073, 1620, 1583, 1501, 1470, 1451, 1288, 1196, 1178, 1153, 1142, 1107, 830 $cm^{-1}$. $^1H$ NMR (DMSO-$d_6$) δ2.08, 2.7, 2.9, 3.8, 6.7, 6.9, 7.8; Anal. Calcd for $C_{13}H_{13}NO_2$: C, 72.54; H, 6.09; N, 6.51. Found: C, 60.95; H, 5.18; N, 5.61.

Preparation 57 9-Benzyl-7-methoxy-1,2,3,9-tetrahydro-4H-carbazol-4-one

To a slurry of sodium hydride (0.26 g, 11 mmol) in dry DMF (50 mL) is added 7-methoxy-1,2,3,9-tetrahydro-4H-carbazol-4-one (2.2 g, 10.2 mmol). The mixture is stirred at room temperature for 30 min. To this is added benzyl bromide (1.3 mL, 11 mmol). The mixture is stirred at room temperature overnight. The mixture is partitioned between water and $Et_2O$. The layers are separated and the organic layer washed twice with water (200 mL). The organic layer is dried over anhydrous sodium sulfate, filtered and concentrated. Column chromatography (200 mL) silica gel using $CH_3OH/CH_2Cl_2$ (2/98) gave 1.7 g (55%) of the title compound; IR (drift) 1638, 1628, 1578, 1535, 1497, 1461, 1449, 1357, 1266, 1200, 1149, 1105, 834, 807, 700 $cm^{-1}$. $^1H$ NMR ($CDCl_3$) δ2.2, 2.6, 2.8, 3.8, 6.7, 6.9, 7.0, 7.3, 8.1; Anal. Calcd for $C_{20}H_{19}NO_2$: C, 78.66; H, 6.27; N, 4.59. Found: C, 78.29; H, 6.39; N, 4.53.

Preparation 58 9-Benzyl-7-methoxy-9H-carbazol-4-ol

To a mixture of 9-benzyl-7-methoxy-1,2,3,9-tetrahydro-4H-carbazol-4-one (1.65 g, 5.4 mmol) in 1:1 p-dioxane:ethylene glycol (50 mL) at 80° C. is added copper (II) chloride (3.6 g, 27 mmol). The mixture is heated for 17 minutes. The mixture is partitioned between water and ethyl acetate. The layers are separated and the ethyl acetate layer washed twice with water (200 mL). The ethyl acetate is dried over anhydrous sodium sulfate, filtered, and concentrated.

The residue is dissolved in DMF (50 mL). Lithium bromide (0.94 g, 10.8 mmol) and lithium carbonate (0.8 g, 10.8 mmol) is added and the mixture heated to 120° C. for 6 hours. The mixture is partitioned between water and ethyl acetate. The layers are separated and the ethyl acetate layer washed twice with water (200 mL). The ethyl acetate is dried over anhydrous sodium sulfate, filtered and concentrated. Column chromatography, silica gel (100 mL), using $CH_2Cl_2/CH_3OH$ (96/4) gave 1.0 gm (61%) of the title compound; IR (drift) 1607, 1465, 1334, 1330, 1320, 1276, 1251, 1207, 1102, 809, 745, 740, 722, 711, 696 $cm^{-1}$. 1H NMR (CDCl3) δ3.9, 5.4, 6.6, 6.8, 6.9, 7.2, 7.2, 8.2); Anal. Calcd for $C_{20}H_{17}NO_2$: C, 79.18; H, 5.65; N, 4.62. Found: C, 78.35; H, 5.66; N, 4.55.

Preparation 59 [(9-Benzyl-7-methoxy-9H-carbazol-4-yl)oxy]acetonitrile

To a mixture of 9-benzyl-7-methoxy-9H-carbazol-4-ol (0.86 g, 2.8 mmol) in DMF (30 mL) is added potassium carbonate (1.17 g, 8.5 mmol) and bromoacetonitrile (0.56 mL, 8.0 mmol). The mixture is stirred at room temperature for 18 h. The mixture is partitioned between water and $CH_2Cl_2$. The layers are separated and the organic layer washed twice with water (100 mL). The organic layer is dried over anhydrous sodium sulfate, filtered, and concentrated. Column chromatography (100 mL) silica gel using $CH_2Cl_2$ as eluent gave 0.9 g (94%) of the title compound; $^1H$ NMR (CDCl₃) δ3.86, 5.04, 5.46, 6.73, 6.82, 6.87, 7.05, 7.14, 7.28, 8.15; Anal. Calcd for $C_{22}H_{18}N_2O_2$: C, 77.17; H, 5.30; N, 8.18. Found: C, 76.00; H, 5.32; N, 8.43.

Example 62
2-[(9-Benzyl-7-methoxy-9H-carbazol-4-yl)oxy]ethylamine

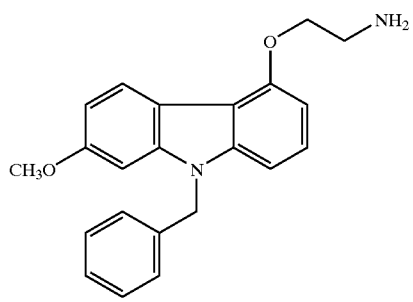

To a mixture of [(9-benzyl-7-methoxy-9H-carbazol-4-yl)oxy]acetonitrile (0.9 g, 2.6 mmol) in dry THF (50 mL) is added borane-methylsulfide complex (0.75 mL, 7.9 mmol). The mixture is heated at 40° C. overnight. Methanol is slowly added to mixture until addition of methanol did not evolve gas. The solvents are removed under reduced pressure. Methanol (50 mL) is added to the residue then removed under reduced pressure. Methanol (100 mL) and concentrated hydrochloric acid (3 mL) is added to the residue. The mixture is heated at 75° C. for 2.5 h. The mixture is neutralized with saturated potassium carbonate and partitioned between water and ethyl acetate. The layers are separated and the organic layer washed twice with brine. The organic layer is dried over anhydrous sodium sulfate, filtered, and concentrated. Column chromatography, silica gel (100 mL) using $CH_2Cl_2$: $CH_3OH$ (95:5) as eluent gave 0.52 g (58%) of the title compound; $^1H$ NMR (DMSO-d₆) δ2.48, 3.8, 4.12, 5.59, 6.69, 6.8, 7.14, 7.2, 8.03; Anal. Calcd for $C_{22}H_{22}N_2O_2$: C, 76.28; H, 6.40; N, 8.09. Found: C, 76.00; H, 6.54; N, 7.92.

CHART A

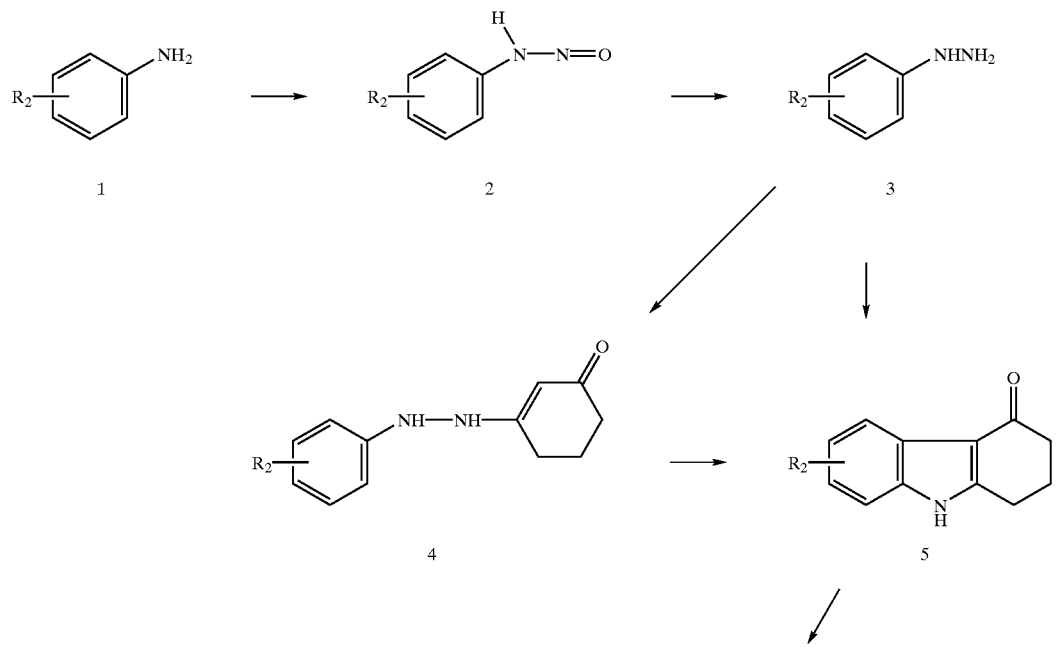

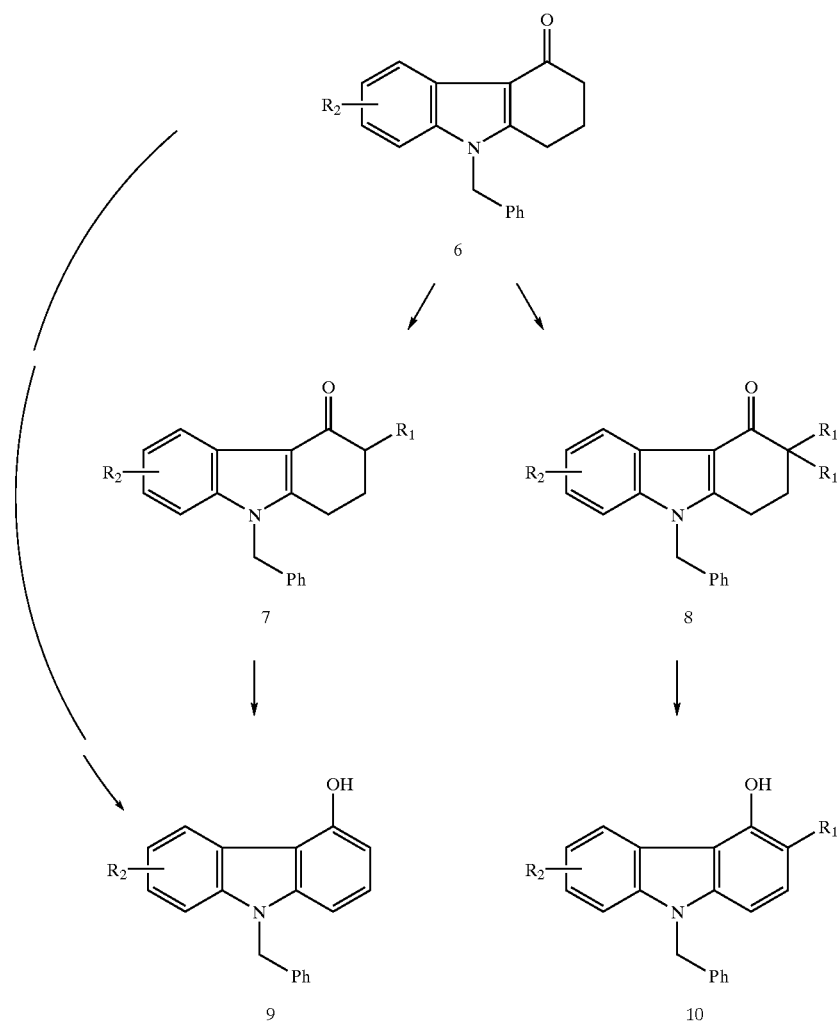
CHART B
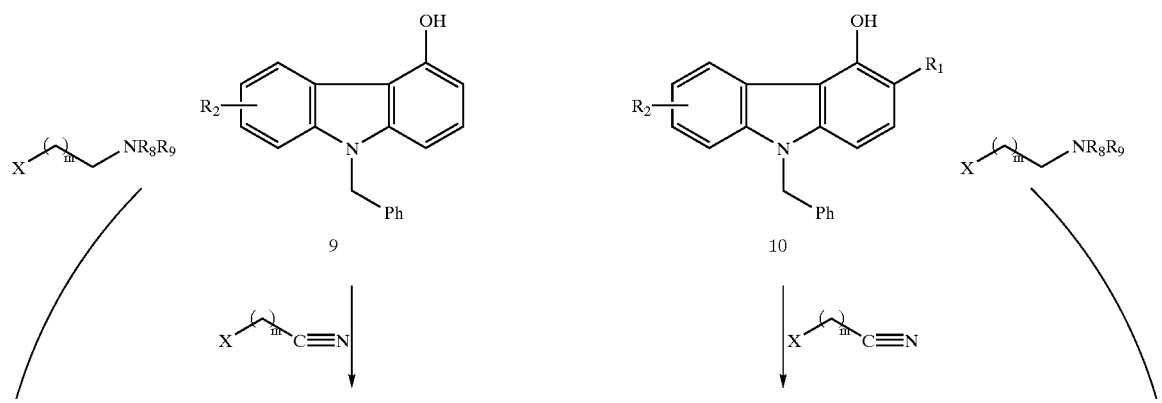

-continued
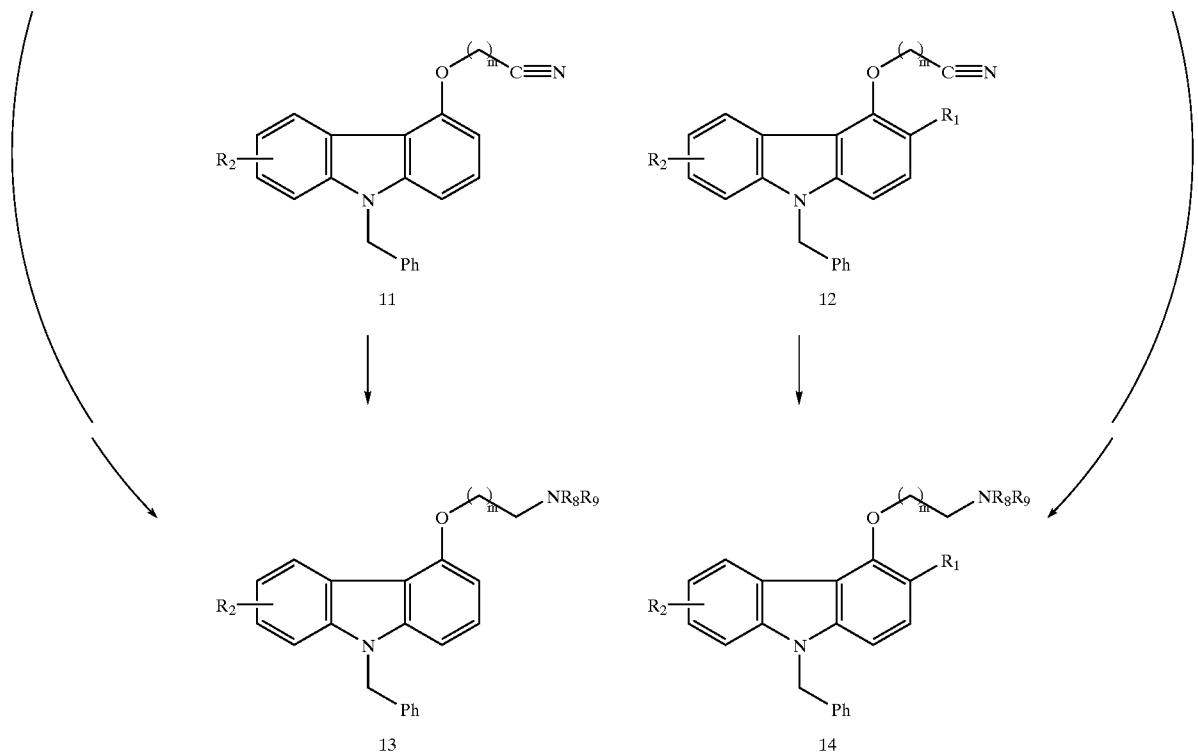
CHART C
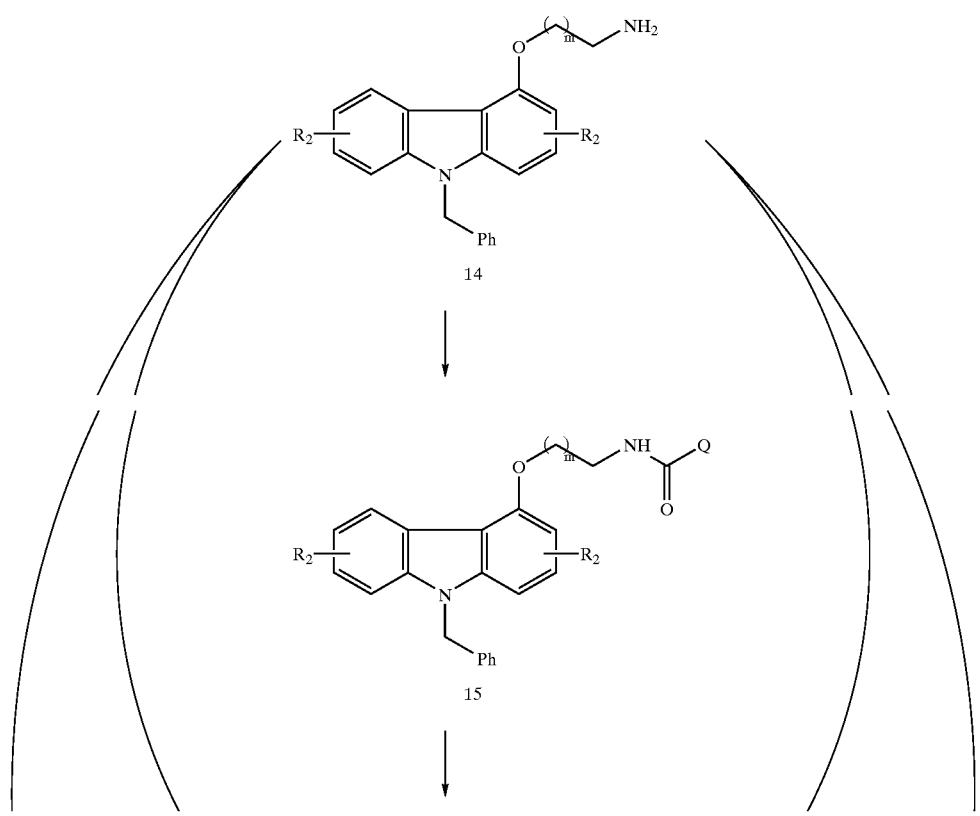

-continued
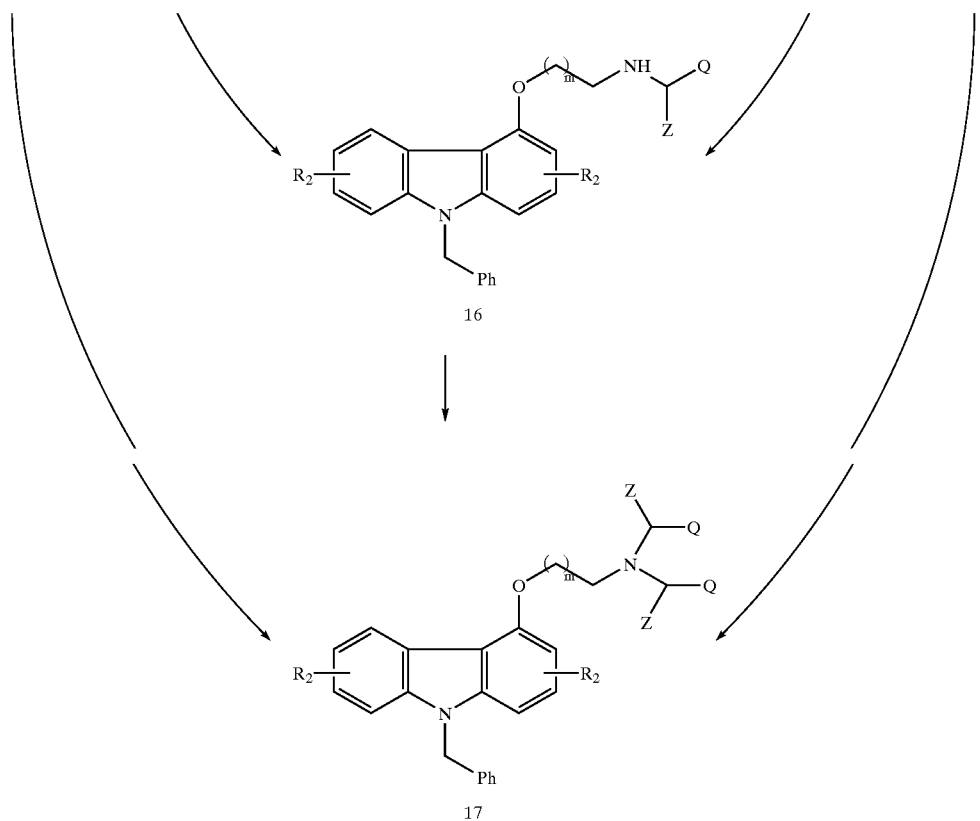
CHART D
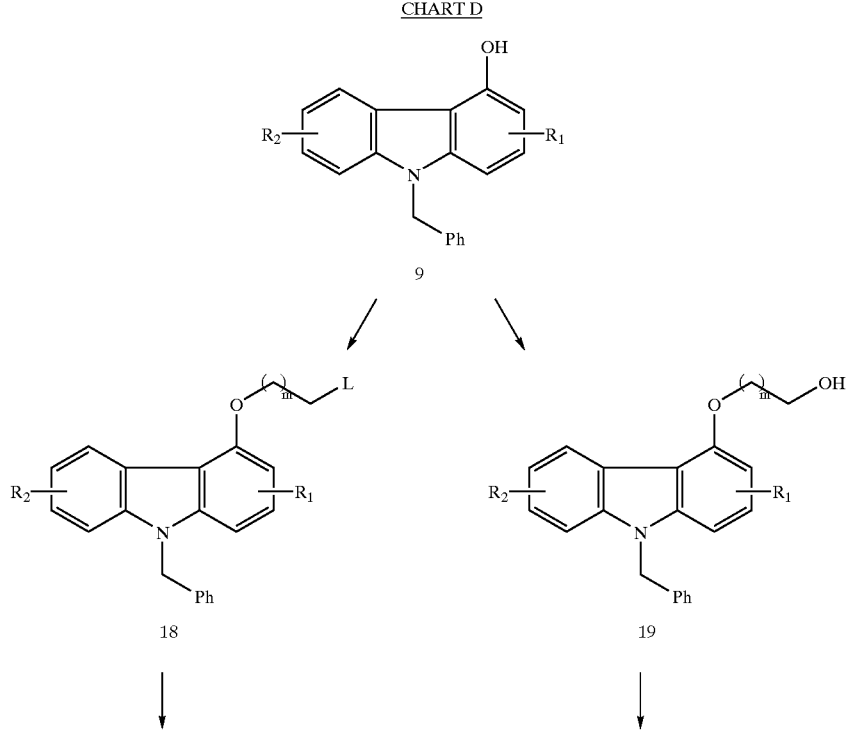

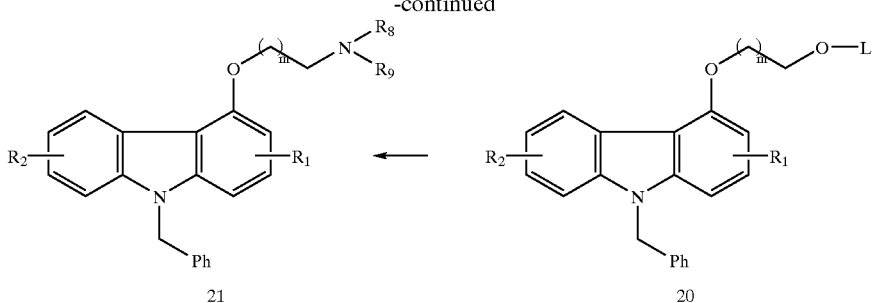

21 ← 20

What is claimed is:

1. A compound of formula I

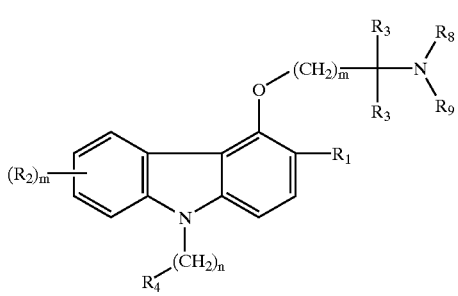

I or a pharmaceutically acceptable salt, racemate, solvate, tautomer, or optical isomer thereof;
wherein $R_1$ is
(a) H,
(b) halo, or
(c) $C_{1-6}$ alkyl;

each $R_2$ is independently
(a) H,
(b) halo,
(c) —OH,
(d) —CN,
(e) —$CF_3$,
(f) —O($C_{1-6}$)alkyl,
(g) $C_{1-6}$ alkyl,
(h) $C_{3-6}$ cycloallyl,
(i) —$NR_5R_6$,
(j) —$CONR_5R_6$,
(k) —$SO_2NR_5R_6$,
(l) —$COOR_7$,
(m) —$OCF_3$, or
(n) phenyl, optionally substituted with halo, OH, O($C_{1-4}$) alkyl, or $C_{1-6}$ alkyl;

each $R_3$ is independently
(a) H,
(b) $C_{1-6}$ alkyl, or
(c) $C_{3-6}$ cycloalkyl;

$R_4$ is
(a) aryl, or
(b) heteroaryl;

$R_5$ and $R_6$ are independently
(a) H,
(b) $C_{1-6}$ alkyl, or
(c) $C_{3-6}$ cycloalkyl;

$R_7$ is
(a) H,
(b) $C_{1-6}$ alkyl, or
(c) ($C_{1-3}$ alkyl)-phenyl wherein phenyl may be substituted with $R_3$;

$R_8$ and $R_9$ are independently
(a) H,
(b) $C_{1-6}$ alkyl, optionally substituted with aryl, hetroaryl, or $C_{3-6}$ cycloalkyl,
(c) $C_{2-6}$ alkenyl,
(d) $C_{3-6}$ cycloalkyl,
(e) $C_{2-6}$ alkyl substituted with $R_{10}$,
(f) —CHO, provided that only one of the $R_8$ and $R_9$ is CHO, the other one is H,
(g) aryl,
(h) heterocyclic, wherein heterocyclic is bonded via carbon atom to the nitrogen to which it is attached, or
(i) $R_8$ and $R_9$ taken together with the nitrogen to which they are attached form a heterocyclic ring wherein the heterocyclic ring may have one to two additional heteroatoms selected from the group consisting of oxygen, sulfur and N(Y) and wherein the carbon atoms of the heterocyclic ring is optionally substituted with one or two $R_{14}$;

$R_{10}$ is
(c) —OH,
(d) —O($C_{1-4}$ alkyl), optionally alkyl is substituted with OH,
(c) —O($C_{1-4}$ alkyl)-$NR_{11}R_{12}$,
(d) heterocyclic, or
(e) —$CO_2R_5$, $R_{11}$ and $R_{12}$ are independently,
(c) H, or
(d) $C_{1-4}$alkyl;

aryl is phenyl or naphthyl, optionally substituted with one or more $R_{13}$;

heteroaryl is a radical of a five- or six-membered monocyclic aromatic ring having one or two heteroatoms each selected from the group consisting of oxygen, sulfur, and N(X), or a radical of a nine- or ten-membered ortho-fused bicyclic aromatic ring having one, two or three heteroatoms each selected from the group consisting of oxygen, sulfur, and N(X); wherein carbon atoms of heteroaryl may be substituted with $R_{13}$;

heterocyclic is a radical of a five-, six-, or seven-membered partially-saturated or unsaturated heterocyclic ring having one, two or three heteroatoms selected from the group consisting of oxygen, sulfur and N(Y) wherein the carbon atoms of the heterocyclic ring may be substituted with $R_{14}$;

X is absent, H or $C_{1-4}$ alkyl;

Y is
  (a) H,
  (b) $C_{1-6}$ alkyl, optionally substituted with aryl or heteroaryl,
  (c) $C_{3-6}$ cycloalkyl, or
  (d) $C_{2-6}$ alkyl substituted with —OH, —O($C_{1-4}$ alkyl), —O($C_{1-4}$ alkyl)-$NR_{11}R_{12}$, —$CO_2R_5$, or NHCHO, or
  (e) —OH;

$R_{13}$ is
  (a) halo,
  (b) —OH,
  (c) —CN,
  (d) —$CF_3$,
  (e) —O($C_{1-6}$)alkyl,
  (f) $C_{1-6}$ alkyl,
  (g) $C_{3-6}$ cycloalkyl,
  (h) —$NR_5R_6$,
  (i) —$CONR_5R_6$,
  (j) —$SO_2NR_5R_6$,
  (k) —$COOR_7$,
  (l) —$OCF_3$, or
  (m) phenyl, optionally substituted with halo, OH, O($C_{1-4}$) alkyl, or $C_{1-6}$ alkyl;

$R_{14}$ is
  (a) $C_{1-6}$ alkyl,
  (b) $C_{3-6}$ cycloalkyl,
  (c) $C_{2-6}$ alkyl substituted with —OH, —O($C_{1-4}$ alkyl), —O($C_{1-4}$ alkyl)-$NR_{11}R_{12}$, or —$CO_2R_5$,
  (d) —OH, or
  (e) oxo (=O);

m is 1, 2, 3 or 4;

n is 1, 2, 3, or 4; $C_{3-6}$ cycloalkyl in each of the above definitions, may be each and independently substituted with —OH, $C_{1-4}$ alkyl, or oxo (=O), and with the following provisos:
  (a) when $R_4$ is 4-fluorophenyl, n is 1, m is 1, each $R_3$ is independently hydrogen, $R_8$ and $R_9$ is independently —$CH_2CH_3$, then $R_2$ cannot be fluoro or chloro at the C-6 position of formula I;
  (b) when n is 1, m is 1, $R_2$, $R_3$, $R_8$ or $R_9$ is hydrogen, $R_4$ is 4-thiazolyl, then said 4-thiazolyl cannot be substituted with 4-chlorophenyl;
  (c) when n is 1, m is 1, $R_2$, $R_3$, $R_8$ or $R_9$ is hydrogen, then $R_4$ is not 4-pyridyl;
  (d) when n is 1, m is 1, $R_2$, $R_3$, $R_8$ or $R_9$ is hydrogen, then $R_4$ is not 2-bromophenyl or 4-bromophenyl.

2. A compound of claim 1 wherein $R_1$ is H, $CH_3$, fluoro or chloro.

3. A compound of claim 1 wherein $R_1$ is H.

4. A compound of claim 1, 2, 3 wherein $R_2$ is H, halo, —OH, —CN, —$CF_3$, —O($C_{1-6}$)alkyl, $C_{1-6}$ alkyl, $C_{3-6}$ cycloalkyl, —$NR_5R_6$, —$CONR_5R_6$, —$SO_2NR_5R_6$, —$COOR_7$, or phenyl, optionally substituted with halo, OH, O($C_{1-4}$) alkyl, or $C_{1-6}$ alkyl, wherein $R_5$, $R_6$ and $R_7$ are the same as defined in claim 1.

5. A compound of claim 1, 2 or 3 wherein $R_2$ is halo, or $C_{1-6}$ alkyl.

6. A compound of claim 1, 2 or 3 wherein $R_2$ is H.

7. A compound of claim 1, 2 or 3 wherein $R_2$ chloro or fluoro.

8. A compound of claim 1, 2 or 3 wherein $R_2$ is methyl.

9. A compound of claim 5 wherein m is 1.

10. A compound of claim 4 wherein $R_4$ is heteroaryl.

11. A compound of claim 4 wherein $R_4$ is phenyl, optionally substituted with fluoro or chloro.

12. A compound of claim 10 wherein $R_4$ is pyridyl, thiophene, benzothiophene, benzofuran, benzimidazole, imidazole or thiazole.

13. A compound of claim 10 wherein $R_4$ is 2-methyl-1,3-thiazol-4-yl or 5-chloro-1-benzothiophene-3-yl.

14. A compound of claim 4 wherein each $R_3$ is independently H, $C_{1-6}$ alkyl, or $C_{3-6}$ cycloalkyl.

15. A compound of claim 4 wherein each $R_3$ is independently H.

16. A compound of claim 4 wherein $R_8$ and $R_9$ are independently
  (a) H,
  (b) $C_{1-6}$ alkyl, optionally substituted with aryl, heteroaryl, or $C_{3-6}$ cycloalkyl,
  (c) $C_{2-6}$ alkene,
  (d) $C_{3-6}$ cycloalkyl,
  (e) $C_{2-6}$ alkyl substituted with $R_{10}$,
  (f) —CHO,
  (g) aryl,
  (h) heterocyclic, wherein heterocyclic is bonded via carbon atom to the nitrogen to which it is attached, or
  (i) $R_8$ and $R_9$ taken together with the nitrogen to which they are attached form a heterocyclic ring wherein the heterocyclic ring may have one to two additional heteroatoms selected from the group consisting of oxygen, sulfur and N(Y) and wherein the carbon atoms of the heterocyclic ring are optionally substituted with one or two $R_{14}$; wherein $R_{10}$ and Y are the same as defined in claim 1.

17. A compound of claim 16 wherein $R_8$ is H, $R_9$ is H.

18. A compound of claim 16 wherein $R_8$ is H, $R_9$ is $C_{1-6}$ alkyl, $C_{2-4}$ alkenyl, or —CHO.

19. A compound of claim 16 wherein $R_8$ is H, $R_9$ is methyl.

20. A compound of claim 16 wherein $R_8$ is H, $R_9$ is $C_{1-6}$ alkyl substituted with $C_{3-6}$ cycloalkyl, wherein cycloalkyl is optionally substituted with —OH, $C_{1-4}$ alkyl or oxo.

21. A compound of claim 16 wherein cycloalkyl is cyclopropyl, cyclobutyl, cyclopentyl, or cyclohexyl.

22. A compound of claim 16 wherein $R_8$ is H, $R_9$ is $C_{2-6}$ alkyl substituted with —OH, —O($C_{1-4}$ alkyl), —O($C_{1-4}$ alkyl-OH), or —$CO_2C_{1-4}$ alkyl.

23. A compound of claim 16 wherein $R_8$ is H, $R_9$ is is cyclopropyl, cyclobutyl, cyclopently, or cyclohexyl, optionally substituted with —OH, $C_{1-4}$ alkyl or oxo.

24. A compound of claim 16 wherein $R_8$ is H, $R_9$ is $C_{1-6}$ alkyl substituted with
  (a) phenyl, optionally substituted with fluoro or chloro,
  (b) pyridyl, thiophene, benzothiophene, benzofuran, benzimidazole, imidazole or thiazole, or
  (c) heterocyclic, which is bonded via carbon atom to the nitrogen to which it is attached.

25. A compound of claim 16 wherein $R_8$ is H, $R_9$ is $C_{1-4}$ alkyl substituted with fluorophenyl, chlorophenyl, pyridyl, benzimidazole, or 1-benzyl-piperidinyl.

26. A compound of claim 16 wherein $R_8$ is H, $R_9$ is $C_{2-6}$ alkyl substituted with azetidyl, pyrrolidinyl, piperidinyl, piperazinyl, morpholinyl, thiomorpholinyl, 1-benzyl-piperidinyl, 1-methyl-piperidinyl, dioxolane, imidazolidine, oxazolidinyl, oxathiolane, 4-hydroxyl-1-piperidinyl, 4-ethanol-1-piperazinyl-, 4-ethylformamide-1-piperazinyl-, or 4-methyl-1-piperazinyl.

27. A compound of claim 16 wherein $R_8$ and $R_9$ taken together with the nitrogen to which they are attached form a heterocyclic ring wherein the heterocyclic ring may have one to two additional heteroatoms selected from the group consisting of oxygen, sulfur and N(Y), wherein Y is the same as defined in claim 1.

28. A compound of claim 27 wherein $R_8$ and $R_9$ taken together with the nitrogen to which they are attached form 4-morpholinyl, 1-pyrrolidinyl, 1-piperidinyl, 1-piperazinyl, 4-hydroxyl-1-piperidinyl, 4-ethanol-1-piperazinyl-, 4-ethylformamide-1-piperazinyl-, or 4-methyl-1-piperazinyl.

29. A compound of claim 16 wherein $R_8$ and $R_9$ are independently H, methyl, ethyl, propyl, 1-propanol, 2-propenyl, 1-pentanol, 2-methyl-1-propanol, 2-butanol, 1-ethanol, ethoxyl-1-thanol, —CH$_2$CH$_2$CO$_2$ethyl, 2-methoxyethyl, 4-chlorophenethyl, or 4-fluorophenethyl.

30. A compound of claim 16 wherein $R_8$ and $R_9$ taken together with the nitrogen to which they are attached form 4-methyl-1-piperazinyl.

31. A compound of claim 1 which is a) N-{2-[(9-benzyl-9H-carbazol-4-yl)oxy]ethyl}-N,N-diethylamine,
b) N-{2-[(9-benzyl-8-chloro-9H-carbazol-4-yl)oxy]ethyl}-N,N-diethylamine,
c) N-(2-{[8-chloro-9-(4-fluorobenzyl)-9H-carbazol-4-yl]oxy}ethyl)-N,N-diethylamine,
d) N-{2-[(9-benzyl-8-methyl-9H-carbazol-4-yl)oxy]ethyl}-N,N-diethylamine,
e) N,N-diethyl-N-(2-{[9-(4-fluorobenzyl)-8-methyl-9H-carbazol-4-yl]oxy}ethyl)amine,
f) N-{2-[(9-benzyl-9H-carbazol-4-yl)oxy]ethyl}-N-(2-pyridinylmethyl)amine,
g) N-{2-[(9-benzyl-8-fluoro-9H-carbazol-4-yl)oxy]ethyl}-N,N-diethylamine,
h) 9-benzyl-4-[2-(4-morpholinyl)ethoxy]-9H-carbazole,
i) 2-(4-{2-[(9-benzyl-9H-carbazol-4-yl)oxy]ethyl}-1-piperazinyl)-1-ethanol,
j) 3-({2-[(9-benzyl-9H-carbazol-4-yl)oxy]ethyl}amino)-1-propanol,
k) N-{2-[(9-benzyl-9H-carbazol-4-yl)oxy]ethyl}-2-propen-1-amine
l) N-{2-[(9-benzyl-9H-carbazol-4-yl)oxy]ethyl}-3-(4-morpholinyl)-1-propanamine,
m) 5-({2-[(9-benzyl-9H-carbazol-4-yl)oxy]ethyl}amino)-1-pentanol,
n) N-{2-[(9-benzyl-9H-carbazol-4-yl)oxy]ethyl}-1-propanamine,
o) N-{2-[(9-benzyl-9H-carbazol-4-yl)oxy]ethyl}-N-propyl-1-propanamine,
p) 1-benzyl-N-{2-[(9-benzyl-9H-carbazol-4-yl)oxy]ethyl}-4-piperidinamine,
q) 2-({2-[(9-benzyl-9H-carbazol-4-yl)oxy]ethyl}amino)-2-methyl-1-propanol,
r) 2-[(9-benzyl-9H-carbazol-4-yl)oxy]-N-(4-chlorophenethyl)-1-ethanamine,
s) 2-[(9-benzyl-9H-carbazol-4-yl)oxy]-N-(cyclohexylmethyl)-1-ethanamine,
t) 2-[(9-benzyl-9H-carbazol-4-yl)oxy]-N-[2-(4-morpholinyl)ethyl]-1-ethanamine,
u) 1-({2-[(9-benzyl-9H-carbazol-4-yl)oxy]ethyl}amino)-2-butanol,
v) 2-[(9-benzyl-9H-carbazol-4-yl)oxy]-N-(4-fluorophenethyl)-1-ethanamine,
w) 2-[2-({2-[(9-benzyl-9H-carbazol-4-yl)oxy]ethyl}amino)ethoxy]-1-ethanol,
x) (1S,2S)-2-({2-[(9-benzyl-9H-carbazol-4-yl)oxy]ethyl}amino)cyclohexanol,
y) ethyl 3-({2-[(9-benzyl-9H-carbazol-4-yl)oxy]ethyl}amino)propanoate,
z) N-{2-[(9-benzyl-9H-carbazol-4-yl)oxy]ethyl}cyclobutanamine,
aa) 2-(4-{2-[(9-benzyl-9H-carbazol-4-yl)oxy]ethyl}-1-piperazinyl) ethylformamide,
bb) N-(1H-benzimidazol-2-ylmethyl)-2-[(9-benzyl-9H-carbazol-4-yl)oxy]-1-ethanamine,
cc) 1-{2-[(9-benzyl-9H-carbazol-4-yl)oxy]ethyl}-4-piperidinol,
dd) 9-benzyl-4-[2-(4-methyl-1-piperazinyl)ethoxy]-9H-carbazole,
ee) N-{2-[(9-benzyl-9H-carbazol-4-yl)oxy]ethyl}-N-cyclopropylamine,
ff) N-{2-[(9-benzyl-9H-carbazol-4-yl)oxy]ethyl}-N,N-dimethylamine,
gg) N-{2-[(9-benzyl-9H-carbazol-4-yl)oxy]ethyl}formamide,
hh) N-{2-[(9-benzyl-9H-carbazol-4-yl)oxy]ethyl}-N-methylamine, or its maleic acid salt,
ii) 2-[(9-benzyl-9H-carbazol-4-yl)oxy]ethylamine,
jj) N-{2-[(9-benzyl-9H-carbazol-4-yl)oxy]ethyl}-N-(2-methoxyethyl)amine,
kk) 2-[(9-benzyl-9H-carbazol-4-yl)oxy]-N-ethyl-1-ethanamine, or its maleic acid salt,
ll) 9-benzyl-4-[2-(1-pyrrolidinyl)ethoxy]-9H-carbazole,
mm) 9-benzyl-4-[2-(1-piperidinyl)ethoxy]-9H-carbazole,
nn) 9-benzyl-4-[2-(1-piperazinyl)ethoxy]-9H-carbazole,
oo) 2-[(9-benzyl-8-fluoro-9H-carbazol-4-yl)oxy]ethylamine,
pp) N,N-diethyl-N-(2-{[8-fluoro-9-(4-fluorobenzyl)-9H-carbazol-4-yl]oxy}ethyl)amine,
qq) N-{2-[(9-benzyl-6-chloro-9H-carbazol-4-yl)oxy]ethyl}-N,N-diethylamine,
rr) N-{2-[(9-benzyl-6-fluoro-9H-carbazol-4-yl)oxy]ethyl}-N,N-diethylamine,
ss) N-{2-[(9-benzyl-6-methyl-9H-carbazol-4-yl)oxy]ethyl}-N,N-diethylamine,
tt) 2-[(9-benzyl-6-methyl-9H-carbazol-4-yl)oxy]ethylamine,
uu) N-{2-[(9-benzyl-6-methyl-9H-carbazol-4-yl)oxy]ethyl}-N-methylamine,
vv) N,N-diethyl-N-(2-{[9-(4-fluorobenzyl)-6-methyl-9H-carbazol-4-yl]oxy}ethyl)amine,
ww) 2-({2-[(9-benzyl-9H-carbazol-4-yl)oxy]ethyl}amino)-1-ethanol or its maleic acid salt,
xx) 2-({9-[(5-chloro-1-benzothiophen-3-yl)methyl]-9H-carbazol-4-yl}oxy)ethylamine or its methane sulfonate salt,
yy) 2-({9-[(2-methyl-1,3-thiazol-4-yl)methyl]-9H-carbazol-4-yl}oxy)ethylamine or its methane sulfonate salt,
zz) 2-[(9-benzyl-3-chloro-9H-carbazol-4-yl)oxy]ethylamine, methanesulfonate salt,
aaa) 2-{[9-(3-bromobenzyl)-9H-carbazol-4-yl]oxy}ethylamine, maleic acid salt,
bbb) 2-{[9-(3-fluorobenzyl)-9H-carbazol-4-yl]oxy}ethylamine, maleic acid salt,
ccc) 2-{[9-(4-methylbenzyl)-9H-carbazol-4-yl]oxy}ethylamine, maleic acid salt,
ddd) 2-{[9-(2-fluorobenzyl)-9H-carbazol-4-yl]oxy}ethylamine, maleic acid salt,
eee) 2-{[9-(3-methoxybenzyl)-9H-carbazol-4-yl]oxy}ethylamine, maleic acid salt,
fff) 2-{[9-(3,5-dimethoxybenzyl)-9H-carbazol-4-yl]oxy}ethylamine, maleic acid salt,
ggg) 2-{[9-(3-methylbenzyl)-9H-carbazol-4-yl]oxy}ethylamine, maleic acid salt,
hhh) 2-{[9-(2-methylbenzyl)-9H-carbazol-4-yl]oxy}ethylamine, maleic acid salt, iii) 2-[(9-benzyl-6-methoxy-9H-carbazol-4-yl)oxy]ethylamine, or jjj) 2-[(9-benzyl-7-methoxy-9H-carbazol-4-yl)oxy]ethylamine.

32. A compound of claim 1 which is a) 2-[(9-benzyl-8-fluoro-9H-carbazol-4-yl)oxy]ethylamine, or
b) 2-[(9-benzyl-8-fluoro-9H-carbazol-4-yl)oxy]ethylamine.

33. A compound of claim 1 which is a) N-{2-[(9-benzyl-9H-carbazol-4-yl)oxy]ethyl}-N-methylamine or its maleic acid salt,
b) 9-benzyl-4-[2-(4-methyl-1-piperazinyl)ethoxy]-9H-carbazole, or
c) N-{2-[(9-benzyl-6-methyl-9H-carbazol-4-yl)oxy]ethyl}-N-methylamine.

34. A method for treating psychosis, paraphrenia, psychotic depression, mania, schizophrenia, schizophreniform disorders, schizoaffective disorder, delusional disorder, panic disorder, a phobia, obsessive compulsive disorder, post-traumatic-stress syndrome, immune system depression, a stress induced problem with the urinary, a stress related disease, migraine headache, drug addiction, convulsive disorders, personality disorders, post-traumatic stress syndrome, alcoholism, panic attacks, obsessive-compulsive disorders, sleep disorders, disorders of the gastrointestinal system or disorders of the cardiovascular system, stress incontinence, neurodegenerative disorders, autism, chemotherapy-induced vomiting, hypertension, cluster headaches, sexual dysfunction in a mammal, addictive disorder and withdrawal syndrome, an adjustment disorder, an age-associated learning and mental disorder, anorexia nervosa, apathy, an attention-deficit disorder due to general medical conditions, attention-deficit hyperactivity disorder, behavioral disturbance, agitation in conditions associated with diminished cognition due to dementia, mental retardation or delirium, bipolar disorder, bulimia nervosa, chronic fatigue syndrome, conduct disorder, cyclothymic disorder, dysthymic disorder, fibromyalgia and other somatoform disorders, an inhalation disorder, an intoxication disorder, movement disorder, Huntington's Disease, Tardive Dyskinesia, oppositional defiant disorder, peripheral neuropathy, post-traumatic stress disorder, premenstrual dysphoric disorder, a psychotic disorder, major depressive mood disorder, bipolar disorder with psychotic features, seasonal affective disorder, a specific developmental disorder, agitation disorder, selective serotonin reuptake inhibition (SSRI) "poop out" syndrome or a Tic disorder, Tourette's syndrome, comprising administering to a mammal in need of such treatment, a therapeutically effective amount of a compound of formula (I)

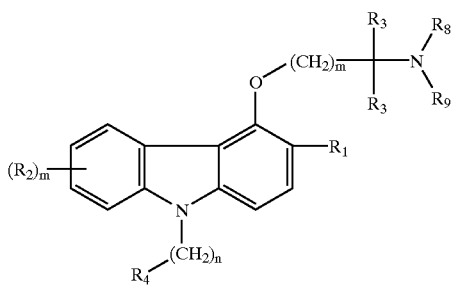

or a pharmaceutically acceptable salt thereof, wherein $R_1$ is
(a) H,
(b) halo, or
(c) $C_{1-6}$ alkyl;

each $R_2$ is independently
(a) H,
(b) halo,
(c) —OH,
(d) —CN,
(e) —$CF_3$,
(f) —$O(C_{1-6})$alkyl,
(g) $C_{1-6}$ alkyl,
(h) $C_{3-6}$ cycloalkyl,
(i) —$NR_5R_6$,
(j) —$CONR_5R_6$,
(k) —$SO_2NR_5R_6$,
(l) —$COOR_7$,
(m) —$OCF_3$, or
(n) phenyl, optionally substituted with halo, OH, $O(C_{1-4})$ alkyl, or $C_{1-6}$ alkyl;

each $R_3$ is independently
(a) H,
(b) $C_{1-6}$ alkyl, or
(c) $C_{3-6}$ cycloalkyl;

$R_4$ is
(a) aryl, or
(b) heteroaryl;

$R_5$ and $R_6$ are independently
(a) H,
(b) $C_{1-6}$ alkyl, or
(c) $C_{3-6}$ cycloalkyl;

$R_7$ is
(a) H,
(b) $C_{1-6}$ alkyl, or
(c) ($C_{1-3}$ alkyl)-phenyl wherein phenyl may be substituted with $R_3$;

$R_8$ and $R_9$ are independently
(a) H,
(b) $C_{1-6}$ alkyl, optionally substituted with aryl, hetroaryl, or $C_{3-6}$ cycloalkyl,
(c) $C_{2-6}$ alkenyl,
(d) $C_{3-6}$ cycloalkyl,
(e) $C_{2-6}$ alkyl substituted with $R_{10}$,
(f) —CHO, provided that only one of the $R_8$ and $R_9$ is CHO, the other one is H,
(g) aryl,
(h) heterocyclic, wherein heterocyclic is bonded via carbon atom to the nitrogen to which it is attached, or
(i) $R_8$ and $R_9$ taken together with the nitrogen to which they are attached form a heterocyclic ring wherein the heterocyclic ring may have one to two additional heteroatoms selected from the group consisting of oxygen, sulfur and N(Y) and wherein the carbon atoms of the heterocyclic ring is optionally substituted with one or two $R_{14}$;

$R_{10}$ is
(c) —OH,
(d) —$O(C_{1-4}$ alkyl), optionally alkyl is substituted with OH,
(c) —$O(C_{1-4}$ alkyl)-$NR_{11}R_{12}$,
(d) heterocyclic, or
(e) —$CO_2R_5$, $R_{11}$ and $R_{12}$ are independently,
(c) H, or
(d) $C_{1-4}$ alkyl;

aryl is phenyl or naphthyl, optionally substituted with one or more $R_{13}$;

heteroaryl is a radical of a five- or six-membered monocyclic aromatic ring having one or two heteroatoms each selected from the group consisting of oxygen, sulfur, and N(X), or a radical of a nine- or ten-membered ortho-fused bicyclic aromatic ring having one, two or three heteroatoms each selected from the group consisting of oxygen, sulfur, and N(X); wherein carbon atoms of heteroaryl may be substituted with $R_{13}$;

heterocyclic is a radical of a five-, six-, or seven-membered partially-saturated or unsaturated heterocyclic ring having one, two or three heteroatoms selected from the group consisting of oxygen, sulfur and N(Y) wherein the carbon atoms of the heterocyclic ring may be substituted with $R_{14}$;

X is absent, H or $C_{1-4}$ alkyl;

Y is
- (a) H,
- (b) $C_{1-6}$ alkyl, optionally substituted with aryl or heteroaryl,
- (c) $C_{3-6}$ cycloalkyl, or
- (d) $C_{2-6}$ alkyl substituted with —OH, —O($C_{1-4}$ alkyl), —O($C_{1-4}$ alkyl)-$NR_{11}R_{12}$, —$CO_2R_5$, or NHCHO, or
- (e) —OH;

$R_{13}$ is
- (a) halo,
- (b) —OH,
- (c) —CN,
- (d) —$CF_3$,
- (e) —O($C_{1-6}$)alkyl,
- (f) $C_{1-6}$ alkyl,
- (g) $C_{3-6}$ cycloalkyl,
- (h) —$NR_5R_6$,
- (i) —$CONR_5R_6$,
- (j) —$SO_2NR_5R_6$,
- (k) —$COOR_7$,
- (l) —$OCF_3$, or
- (m) phenyl, optionally substituted with halo, OH, O($C_{1-4}$) alkyl, or $C_{1-6}$ alkyl;

$R_{14}$ is
- (a) $C_{1-6}$ alkyl,
- (b) $C_{3-6}$ cycloalkyl,
- (c) $C_{2-6}$ alkyl substituted with —OH, —O($C_{1-4}$ alkyl), —O($C_{1-4}$ alkyl)-$NR_{11}R_{12}$, or —$CO_2R_5$,
- (d) —OH, or
- (e) oxo (=O);

m is 1, 2, 3 or 4;

n is 1, 2, 3, or 4;

$C_{3-6}$ cycloalkyl in each of the above definitions, may be each and independently substituted with —OH, $C_{1-4}$ alkyl, or oxo (=O), and with the following provisos:
- (a) when $R_4$ is 4-fluorophenyl, n is 1, m is 1, each $R_3$ is independently hydrogen, $R_8$ and $R_9$ is independently —$CH_2CH_3$, then $R_2$ cannot be fluoro or chloro at the C-6 position of formula I;
- (b) when n is 1, m is 1, $R_2$, $R_3$, $R_8$ or $R_9$ is hydrogen, $R_4$ is 4-thiazolyl, then said 4-thiazolyl cannot be substituted with 4-chlorophenyl;
- (c) when n is 1, m is 1, $R_2$, $R_3$, $R_8$ or $R_9$ is hydrogen, then $R_4$ is not 4-pyridyl;
- (d) when n is 1, m is 1, $R_2$, $R_3$, $R_8$ or $R_9$ is hydrogen, then $R_4$ is not 2-bromophenyl or 4-bromophenyl.

35. A method for treating a disease or condition in a mammal wherein the 5-HT receptor is implicated and modulation of 5-HT function is desired comprising administering a therapeutically effective amount of a compound of claim 1 to the mammal.

36. The method of claim 35 wherein the receptor is a $5\text{-HT}_6$ receptor.

37. The method of claim 34 wherein the disease or condition is anxiety, depression, schizophrenia, a stress related disease, panic disorder, a phobia, obsessive compulsive disorder, post-traumatic-stress syndrome, immune system depression, psychosis, paraphrenia, mania, convulsive disorders, personality disorders, migraine headache, drug addiction, alcoholism, obesity, eating disorders, or sleep disorders.

38. The method of claim 34 wherein the disease or condition is psychotic, affective, vegetative, or psychomotor symptoms of schizophrenia and the extrapyramidal motor side effects of other antipsychotic drugs.

39. The method of claim 34 wherein the disease is anxiety, obesity, depression, or a stress related disease.

40. A method for modulating 5-HT receptor function, comprising contacting the receptor with an effective inhibitory amount of a compound of claim 1.

41. The method of claim 40 wherein the receptor is a $5\text{-HT}_6$ receptor.

42. A compound of claim 6 wherein m is 1.

* * * * *